(12) United States Patent
Moss et al.

(10) Patent No.: US 9,662,325 B2
(45) Date of Patent: *May 30, 2017

(54) USE OF OPIOID ANTAGONISTS TO ATTENUATE ENDOTHELIAL CELL PROLIFERATION AND MIGRATION

(71) Applicant: THE UNIVERSITY OF CHICAGO, Chicago, IL (US)

(72) Inventors: Jonathan Moss, Chicago, IL (US); Mark Lingen, Oak Park, IL (US); Patrick A. Singleton, Chicago, IL (US); Joe G. N. Garcia, Chicago, IL (US); Chun-Su Yuan, Chicago, IL (US)

(73) Assignee: THE UNIVERSITY OF CHICAGO, Chicago, IL (US)

( * ) Notice: Subject to any disclaimer, the term of this patent is extended or adjusted under 35 U.S.C. 154(b) by 185 days.

This patent is subject to a terminal disclaimer.

(21) Appl. No.: 14/292,816

(22) Filed: May 30, 2014

(65) Prior Publication Data

US 2014/0323426 A1 Oct. 30, 2014

Related U.S. Application Data

(63) Continuation-in-part of application No. 13/972,122, filed on Aug. 21, 2013, which is a continuation of application No. 11/379,010, filed on Apr. 17, 2006, now Pat. No. 8,524,731, which is a continuation-in-part of application No. PCT/US2006/007892, filed on Mar. 7, 2006.

(60) Provisional application No. 60/760,851, filed on Jan. 20, 2006, provisional application No. 60/731,009, filed on Oct. 28, 2005, provisional application No. 60/725,703, filed on Oct. 12, 2005, provisional application No. 60/659,193, filed on Mar. 7, 2005.

(51) Int. Cl.
| | |
|---|---|
| *A61K 31/451* | (2006.01) |
| *A61K 31/485* | (2006.01) |
| *A61K 31/00* | (2006.01) |
| *A61K 31/517* | (2006.01) |
| *A61K 31/337* | (2006.01) |
| *A61K 31/7068* | (2006.01) |
| *A61K 39/395* | (2006.01) |
| *A61K 45/06* | (2006.01) |
| *A61K 31/475* | (2006.01) |

(52) U.S. Cl.
CPC .......... *A61K 31/485* (2013.01); *A61K 31/337* (2013.01); *A61K 31/475* (2013.01); *A61K 31/517* (2013.01); *A61K 31/7068* (2013.01); *A61K 39/39558* (2013.01); *A61K 45/06* (2013.01)

(58) Field of Classification Search
CPC .............. A61K 2300/00; A61K 31/451; A61K 31/485; A61K 31/00
See application file for complete search history.

(56) References Cited

U.S. PATENT DOCUMENTS

| | | |
|---|---|---|
| 3,723,440 A | 3/1973 | Freter et al. |
| 3,854,480 A | 12/1974 | Zaffaroni |
| 3,937,801 A | 2/1976 | Lippmann |
| 4,115,400 A | 9/1978 | Zimmerman |
| 4,176,186 A | 11/1979 | Goldberg et al. |
| 4,311,833 A | 1/1982 | Namikoshi et al. |
| 4,322,426 A | 3/1982 | Hermann et al. |
| 4,377,568 A | 3/1983 | Chopra et al. |
| 4,385,078 A | 5/1983 | Onda et al. |
| 4,427,676 A | 1/1984 | White et al. |
| 4,452,775 A | 6/1984 | Kent |
| 4,457,907 A | 7/1984 | Porter et al. |
| 4,462,839 A | 7/1984 | McGinley et al. |
| 4,466,968 A | 8/1984 | Bernstein |
| 4,518,433 A | 5/1985 | McGinley et al. |
| 4,556,552 A | 12/1985 | Porter et al. |
| 4,581,456 A | 4/1986 | Barnett |
| 4,606,909 A | 8/1986 | Bechgaard et al. |
| 4,615,885 A | 10/1986 | Nakagame et al. |
| 4,670,287 A | 6/1987 | Tsuji et al. |
| 4,673,679 A | 6/1987 | Aungst et al. |
| 4,675,189 A | 6/1987 | Kent et al. |
| 4,689,332 A | 8/1987 | McLaughlin et al. |
| 4,719,215 A | 1/1988 | Goldberg |
| 4,730,048 A | 3/1988 | Portoghese |
| 4,806,556 A | 2/1989 | Portoghese |
| 4,836,212 A | 6/1989 | Schmitt et al. |

(Continued)

FOREIGN PATENT DOCUMENTS

| | | |
|---|---|---|
| AU | 610561 | 8/1988 |
| AU | 758416 | 7/1999 |

(Continued)

OTHER PUBLICATIONS

United States Patent Office Action for U.S. Appl. No. 13/972,129 dated Jun. 2, 2015 (28 pages).
Tejwani et al., "Facilitation of dimethylbenz[a]anthracene-induced rat mammary tumorigenesis by restraint stress: role of β-endorphin, prolactin and naltrexone," Carcinogenesis, 1991, vol. 12, No. 4, pp. 637-641.
Ruel-Gariepy et al., "A thermosensitive chitosan-based hydrogel for the local delivery of paclitaxel," European Journal of Pharmaceutics and Biopharmaceutics 57, 2004, 53-63.
United States Patent Office Action for U.S. Appl. No. 13/972,122 dated May 5, 2015 (27 pages).

(Continued)

*Primary Examiner* — Kendra D Carter
(74) *Attorney, Agent, or Firm* — Michael Best & Friedrich LLP

(57) ABSTRACT

The invention provides methods of attenuating, e.g., inhibiting or reducing, cellular proliferation and migration, particularly endothelial cell proliferation and migration, including that associated with angiogenesis, using opioid antagonists, including, but not limited to, those that are peripherally restricted antagonists.

9 Claims, 29 Drawing Sheets

(56) References Cited

U.S. PATENT DOCUMENTS

| | | |
|---|---|---|
| 4,857,533 A | 8/1989 | Sherman et al. |
| 4,861,781 A | 8/1989 | Goldberg |
| 4,863,928 A | 9/1989 | Atkinson et al. |
| 4,888,346 A | 12/1989 | Bihari et al. |
| 4,891,379 A | 1/1990 | Zimmerman et al. |
| 4,912,114 A | 3/1990 | Revesz |
| 4,965,269 A | 10/1990 | Brandstrom et al. |
| 4,987,136 A | 1/1991 | Kreek et al. |
| 5,102,887 A | 4/1992 | Goldberg |
| 5,133,974 A | 7/1992 | Paradissis et al. |
| 5,159,081 A | 10/1992 | Cantrell et al. |
| 5,202,159 A | 4/1993 | Chen et al. |
| 5,250,542 A | 10/1993 | Cantrell et al. |
| 5,270,328 A | 12/1993 | Cantrell et al. |
| 5,391,372 A | 2/1995 | Campbell |
| 5,407,686 A | 4/1995 | Patel et al. |
| 5,426,112 A | 6/1995 | Zagon et al. |
| 5,434,171 A | 7/1995 | Frank et al. |
| 5,472,943 A | 12/1995 | Crain et al. |
| 5,512,578 A | 4/1996 | Crain et al. |
| 5,536,507 A | 7/1996 | Abramowitz et al. |
| 5,567,423 A | 10/1996 | Ying et al. |
| 5,591,433 A | 1/1997 | Michael et al. |
| 5,597,564 A | 1/1997 | Ying et al. |
| 5,609,871 A | 3/1997 | Michael et al. |
| 5,614,219 A | 3/1997 | Wunderlich et al. |
| 5,614,222 A | 3/1997 | Kaplan et al. |
| 5,626,875 A | 5/1997 | Ballester Rodes et al. |
| 5,629,001 A | 5/1997 | Michael et al. |
| 5,656,290 A | 8/1997 | Kelm et al. |
| 5,736,152 A | 4/1998 | Dunn |
| 5,767,125 A | 6/1998 | Crain et al. |
| 5,804,595 A | 9/1998 | Portoghese et al. |
| 5,811,451 A | 9/1998 | Minoia et al. |
| 5,821,219 A | 10/1998 | Grandy et al. |
| 5,866,154 A | 2/1999 | Bahal et al. |
| 5,866,164 A | 2/1999 | Kuczynski et al. |
| 5,958,452 A | 9/1999 | Oshlack et al. |
| 5,972,954 A | 10/1999 | Foss et al. |
| 5,981,185 A | 11/1999 | Matson et al. |
| RE36,547 E | 2/2000 | Crain et al. |
| 6,025,154 A | 2/2000 | Li et al. |
| 6,096,756 A | 8/2000 | Crain et al. |
| 6,096,763 A | 8/2000 | Hoffman et al. |
| 6,096,764 A | 8/2000 | Bryant et al. |
| 6,136,780 A | 10/2000 | Zagon et al. |
| 6,153,620 A | 11/2000 | Kornetsky |
| 6,194,382 B1 | 2/2001 | Crain et al. |
| 6,261,599 B1 | 7/2001 | Oshlack et al. |
| 6,274,591 B1 | 8/2001 | Foss et al. |
| 6,277,384 B1 | 8/2001 | Kaiko et al. |
| 6,353,004 B1 | 3/2002 | Farrar et al. |
| 6,359,111 B1 | 3/2002 | Meyer et al. |
| 6,384,044 B1 | 5/2002 | Bihari |
| 6,395,705 B2 | 5/2002 | Crain et al. |
| 6,414,016 B1 | 7/2002 | Ueno |
| 6,419,959 B1 | 7/2002 | Walter et al. |
| 6,426,094 B2 | 7/2002 | Piver et al. |
| 6,451,806 B2 | 9/2002 | Farrar |
| 6,455,537 B1 | 9/2002 | Cooper |
| 6,469,030 B2 | 10/2002 | Farrar et al. |
| 6,479,500 B1 | 11/2002 | Fukushima et al. |
| 6,559,158 B1 | 5/2003 | Foss et al. |
| 6,608,075 B2 | 8/2003 | Foss et al. |
| 6,610,732 B2 | 8/2003 | Ueno |
| 6,693,125 B2 | 2/2004 | Borisy et al. |
| 6,696,066 B2 | 2/2004 | Kaiko et al. |
| 6,720,336 B2 | 4/2004 | Liras |
| 6,723,712 B2 | 4/2004 | Bourhis et al. |
| 6,756,364 B2 | 6/2004 | Barbier et al. |
| 6,765,010 B2 | 7/2004 | Crain et al. |
| 6,774,128 B2 | 8/2004 | Watkins et al. |
| 6,777,534 B1 | 8/2004 | Klagsbrun et al. |
| 6,794,370 B2 | 9/2004 | Achterrath |
| 6,800,639 B2 | 10/2004 | Giles et al. |
| 6,833,349 B2 | 12/2004 | Xia et al. |
| 6,838,469 B2 | 1/2005 | Sumegi |
| 6,884,879 B1 | 4/2005 | Baca et al. |
| 6,900,234 B1 | 5/2005 | Fossa |
| 6,946,556 B1 | 9/2005 | Likhotvorik et al. |
| 6,960,596 B2 | 11/2005 | Bissery |
| 6,967,016 B2 | 11/2005 | van Gemen et al. |
| 6,982,283 B2 | 1/2006 | Ueno |
| 6,984,403 B2 | 1/2006 | Hagen et al. |
| 6,989,383 B1 | 1/2006 | Rosen et al. |
| 6,992,106 B2 | 1/2006 | Morinaga et al. |
| 7,012,100 B1 | 3/2006 | Edwards et al. |
| 7,041,704 B2 | 5/2006 | Burgard et al. |
| 7,056,500 B2 | 6/2006 | Bentley et al. |
| 7,064,148 B2 | 6/2006 | Ueno et al. |
| 7,074,825 B2 | 7/2006 | Mo et al. |
| 7,094,775 B2 | 8/2006 | Strugnell et al. |
| 7,129,265 B2 | 10/2006 | Mason |
| 7,132,554 B2 | 11/2006 | Rose |
| 7,141,554 B2 | 11/2006 | Rochat et al. |
| 7,160,913 B2 | 1/2007 | Schneider |
| 7,183,269 B2 | 2/2007 | Kreutz |
| 7,196,115 B2 | 3/2007 | Khanuja et al. |
| 7,253,295 B2 | 8/2007 | Ueno et al. |
| 7,259,233 B2 | 8/2007 | Dodd et al. |
| 7,384,940 B2 * | 6/2008 | Agus .............. A61K 31/00 514/228.2 |
| 8,518,962 B2 | 8/2013 | Moss et al. |
| 8,524,731 B2 | 9/2013 | Moss et al. |
| 2001/0010919 A1 | 8/2001 | Grandy et al. |
| 2001/0018413 A1 | 8/2001 | Crain et al. |
| 2001/0033865 A1 | 10/2001 | Oshlack et al. |
| 2001/0036469 A1 | 11/2001 | Gooberman |
| 2001/0036476 A1 | 11/2001 | Oshlack et al. |
| 2001/0036951 A1 | 11/2001 | Farrar et al. |
| 2001/0046968 A1 | 11/2001 | Zagon et al. |
| 2001/0047005 A1 | 11/2001 | Farrar et al. |
| 2002/0028825 A1 | 3/2002 | Foss et al. |
| 2002/0064771 A1 | 5/2002 | Zhong et al. |
| 2002/0068712 A1 | 6/2002 | Stevens |
| 2002/0173466 A1 | 11/2002 | Crain et al. |
| 2002/0188005 A1 | 12/2002 | Farrar et al. |
| 2003/0022909 A1 | 1/2003 | Moss et al. |
| 2003/0026801 A1 | 2/2003 | Weiner et al. |
| 2003/0039689 A1 | 2/2003 | Chen et al. |
| 2003/0065003 A1 | 4/2003 | Foss et al. |
| 2003/0068319 A1 | 4/2003 | Bar-Eli |
| 2003/0073746 A1 | 4/2003 | Ueno |
| 2003/0105121 A1 | 6/2003 | Bihari |
| 2003/0119898 A1 | 6/2003 | Ueno et al. |
| 2003/0130352 A1 | 7/2003 | Ueno et al. |
| 2003/0144312 A1 | 7/2003 | Schoenhard |
| 2003/0158220 A1 | 8/2003 | Foss et al. |
| 2003/0166632 A1 | 9/2003 | Ueno |
| 2003/0191147 A1 | 10/2003 | Sherman et al. |
| 2003/0216465 A1 | 11/2003 | Ueno |
| 2003/0219406 A1 | 11/2003 | Schroit et al. |
| 2004/0024006 A1 | 2/2004 | Simon |
| 2004/0162306 A1 | 8/2004 | Foss et al. |
| 2004/0162308 A1 | 8/2004 | Foss et al. |
| 2004/0167148 A1 | 8/2004 | Foss et al. |
| 2004/0242523 A1 | 12/2004 | Weichselbaum et al. |
| 2004/0254156 A1 | 12/2004 | Le Bourdonnec et al. |
| 2004/0254208 A1 | 12/2004 | Weber et al. |
| 2004/0259898 A1 | 12/2004 | Moss |
| 2004/0259899 A1 | 12/2004 | Sanghvi et al. |
| 2004/0266806 A1 | 12/2004 | Sanghvi et al. |
| 2005/0004029 A1 | 1/2005 | Garcia |
| 2005/0004155 A1 | 1/2005 | Boyd et al. |
| 2005/0011468 A1 | 1/2005 | Moss |
| 2005/0048117 A1 | 3/2005 | Foss et al. |
| 2005/0085514 A1 | 4/2005 | Cosford et al. |
| 2005/0112067 A1 | 5/2005 | Kumar |
| 2005/0124885 A1 | 6/2005 | Abend et al. |
| 2005/0187255 A1 | 8/2005 | Lee et al. |
| 2006/0025592 A1 | 2/2006 | Stranix et al. |
| 2006/0063792 A1 | 3/2006 | Dolle et al. |
| 2006/0094658 A1 | 5/2006 | Currie et al. |
| 2006/0115424 A1 | 6/2006 | Gray |

(56) References Cited

U.S. PATENT DOCUMENTS

| | | |
|---|---|---|
| 2006/0128742 A1 | 6/2006 | Edwards et al. |
| 2006/0204512 A1 | 9/2006 | Krasnoperov et al. |
| 2006/0205753 A1 | 9/2006 | Israel |
| 2006/0281682 A1 | 12/2006 | Currie et al. |
| 2007/0010450 A1 | 1/2007 | Currie et al. |
| 2007/0010543 A1 | 1/2007 | Ashburn |
| 2007/0020261 A1 | 1/2007 | Sliwkowski et al. |
| 2007/0060501 A1 | 3/2007 | Jhamandas et al. |
| 2007/0071761 A1 | 3/2007 | Seon |
| 2007/0082044 A1 | 4/2007 | Yeum |
| 2007/0099946 A1 | 5/2007 | Doshan |
| 2007/0099988 A1 | 5/2007 | Sandage |
| 2007/0265293 A1 | 11/2007 | Boyd et al. |
| 2008/0194611 A1 | 8/2008 | Alverdy et al. |
| 2008/0274119 A1 | 11/2008 | Moss et al. |
| 2009/0209569 A1 | 8/2009 | Arnelle et al. |
| 2012/0316190 A1 | 12/2012 | Alverdy et al. |
| 2014/0011831 A1 | 1/2014 | Moss et al. |
| 2014/0066467 A1 | 3/2014 | Moss et al. |
| 2014/0142133 A1 | 5/2014 | Alverdy et al. |

FOREIGN PATENT DOCUMENTS

| | | |
|---|---|---|
| CA | 2064373 | 9/1992 |
| CA | 1315689 | 4/1993 |
| CA | 2312234 | 5/1999 |
| DE | 3780819 | 1/1993 |
| DE | 4303214 | 8/1994 |
| DE | 19651551 | 6/1998 |
| EP | 0278821 | 8/1988 |
| EP | 0289070 | 11/1988 |
| EP | 0306575 | 3/1989 |
| EP | 0352361 | 1/1990 |
| EP | 0506468 | 9/1992 |
| EP | 0643967 | 3/1995 |
| EP | 0760661 | 12/1998 |
| EP | 1047726 | 7/1999 |
| JP | 1068376 | 3/1989 |
| JP | 02-184628 | 7/1990 |
| NZ | 222911 | 12/1987 |
| WO | WO 83/03197 | 2/1983 |
| WO | WO 88/05297 | 7/1988 |
| WO | WO 93/17019 | 9/1993 |
| WO | WO 94/10202 | 5/1994 |
| WO | WO 95/09168 | 4/1995 |
| WO | WO 95/31985 | 11/1995 |
| WO | WO 96/14058 | 5/1996 |
| WO | WO 97/33566 | 9/1997 |
| WO | WO 97/36608 | 10/1997 |
| WO | WO 98/25613 | 6/1998 |
| WO | WO 99/01033 | 1/1999 |
| WO | WO 99/22737 | 5/1999 |
| WO | WO 99/36470 | 7/1999 |
| WO | WO 01/13909 | 3/2001 |
| WO | WO 01/32180 | 5/2001 |
| WO | WO 01/37785 | 5/2001 |
| WO | WO 01/41705 | 6/2001 |
| WO | WO 01/42207 | 6/2001 |
| WO | 01/70031 | 9/2001 |
| WO | WO 01/70031 | 9/2001 |
| WO | WO 01/85257 | 11/2001 |
| WO | WO 02/060870 | 8/2002 |
| WO | WO 02/098422 | 12/2002 |
| WO | WO 03/009829 | 2/2003 |
| WO | WO 03/020296 | 3/2003 |
| WO | WO 03/032990 | 4/2003 |
| WO | 03037340 | 5/2003 |
| WO | WO 03/037340 | 5/2003 |
| WO | WO 03/070232 | 8/2003 |
| WO | WO 2004/007503 | 1/2004 |
| WO | WO 2004/014291 | 2/2004 |
| WO | WO 2004/043964 | 5/2004 |
| WO | WO 2004/080996 | 9/2004 |
| WO | WO 2004/091622 | 10/2004 |
| WO | WO 2004/091623 | 10/2004 |
| WO | WO 2006/096626 | 9/2006 |
| WO | WO 2006/127898 | 11/2006 |
| WO | WO 2006/127899 | 11/2006 |
| WO | WO 2006/132963 | 12/2006 |
| WO | WO 2007/022531 | 2/2007 |
| WO | WO 2007/053194 | 8/2007 |
| WO | 2007/121447 | 10/2007 |
| WO | WO 2007/131154 | 11/2007 |
| WO | WO 2009/045985 | 4/2009 |
| WO | WO 2009/076195 | 6/2009 |

OTHER PUBLICATIONS

Logothetis et al., "Doxorubicin, Mitomycin-D and 5-Fluorouracil (DMF) in the Treatment of Metastatic Hormonal Refractory Adenocarcinoma of the Prostte, Wigh a Note on the Staging of Metastatic Prostate Cancer," Journal of Clinical Oncology, 1983, vol. 1, No. 6, pp. 368-379.

"Cancer Pain Remedy Wins Orphan Drug Status," "New Drug Doesn't Cross Blood-Brain Barrier," Research Reports in Oncology (1996) 10(12):1880.

"Methylnaltrexone: MNTX," Drugs RD (2006) 7(6):374-378.

Aballay, A. et al., "Caenorhabditis elegans as a host for the study of host-pathogen interactions," Curr. Opin. Microbiol. (2002) 5:97-101.

Aepfelbacher, M. et al., "Bacterial toxins block endothelial wound repair. Evidence that Rho GTPases control cytoskeletal rearrangements in migrating endothelial cells," Arterioscler. Thromb. Vasc. Biol. (1997) 17(9):1623-1629.

Akinbami, M.A. et al., Effect of a peripheral and a central acting opioid antagonist on the testicular response to stress in rats. Neuroendocrinology. Apr. 1994;59(4):343-8.

Aliaga, L. et al., "A clinical index predicting mortality with Pseudomonas aeruginosa bacteraemia," J. Med. Microbiol. (2002) 51:615-619.

Altier, N. et al., Opioid receptors in the ventral tegmental area contribute to stress-induced analgesia in the formalin test for tonic pain. Brain Res. Apr. 29, 1996;718(1-2):203-6.

Alverdy et al., "Influence of the critically ill state on host-pathogen interactions within the intestine: gut-derived sepsis redefined," Crit. Care Med. (2003) 31(2):598-607.

Alverdy, J. et al., "Gut-derived sepsis occurs when the right pathogen with the right verulence genes meets the right host: evidence for in vivo virulence expression and Pseudomonas aeruginosa," Ann. Surg. (2000) 232(4):480-489.

Alverdy, J.C. et al., "Surgical stress, bacteria, and mucosal immune function," Eur. J. Pediatr. Surg. (1999) 9:210-213.

Ambizas, E.M. et al., "Lubiprostone: a chloride channel activator for treatment of chronic constipation," Ann. Pharmacother. (2007) 41:957-964.

Amin, H.M. et al., Efficacy of methylnaltrexone versus naloxone for reversal of morphine-induced depression of hypoxic ventilatory response. Anesth Analg. Apr. 1994;78(4):701-5.

Amir, S. et al., Endorphins in endotoxin-induced hyperglycemia in mice. Arch Toxicol Suppl. 1983;6:261-5.

Amir, S., Naloxone improves, and morphine exacerbates, experimental shock induced by release of endogenous histamine by compound 48/80. Brain Res. Apr. 9, 1984;297(1):187-90.

Anderson, G.L. et al., "Assessing behavior toxicity with Caenorhabditis elegans," Environ. Toxicol. Chem. (2004) 23:1235-1240.

Angus, D.C. et al., Epidemiology of sepsis: an update, Crit. Care Med. (2001) 29(7):S109-S116.

Arai, M. et al., "Contribution of adenosine $A_2$ receptors and cyclic adenosine monophosphate to protective ischemic preconditioning of sinusoidal Ecs against storage/reperfusion injury in rat livers," Hepatology (2000) 32:297-302.

Arbo, M.D. et al., "Utility of serial rectal swab cultures for detection of ceftazidime- and imipenem-resistant gram-negative bacilli from patients in the invensive care unit," Eur. J. Clin. Microbiol. Infect. Dis. (1998) 17:727-730.

Arendt, R.M. et al., "Bidirectional effects of endogenous opioid peptides on endothelin release rates in porcine aortic endothelial cell

(56) References Cited

OTHER PUBLICATIONS culture: mediation by δ opioid receptor and opioid receptor antagonist-insensitive mechanisms," J. Pharmacol. Exp. Thera. (1995) 272(1):1-7.

Arerangaiah, R. et al., "Opioids induce renal abnormalities in tumor bearing mice," Nephron. Exp. Nephrol. (2007) 105:e80-e89.

Argentieri, T.M. et al., Interaction of the opiate antagonist, naltrexone methyl bromide, with the acetylcholine receptor system of the motor end-plate. Brain Res. Oct. 31, 1983;277(2):377-9.

Armstead, W.M., "Relationship between NO, the $K_{ATP}$ channel, and opioids in hypoxic pial artery dilation," Am. J. Physiol. (1998) 275:H988-H994—Abstract 3720.

Armstrong, S. et al., "The gastrointestinal activity and peripheral selectivity of alvimopan, ADL08-0011, and naloxone in mice," May 21, 2006 DDW Presentation in Los Angeles, Clinical Pharm. Therap. (2005) 77:74.

Aung, H. et al., "Scutellaria baicalensis decreases ritonavir-induced nausea," AIDS Research and Therapy (2005) 2(1):12 (6 pages).

Aung, H.H. et al., "Scutellaria baicalensis extract decreases cisplatin-induced pica in rats," Cancer Chemother. Pharmacol. (2003) 52:453-458.

Aung, H.H. et al., Methylnaltrexone prevents morphine-induced kaolin intake in the rat. Life Sci. Apr. 16, 2004;74(22):2685-91.

Autar, R. et al, "Adhesion inhibition of F1C-fimbriated *Escherichia coli* and Pseudomonas aeruginosa PAK and PAO by multivalent carbohydrate ligands," Chembiochem. (2003) 4:1317-1325.

Azghani, A.O. et al., "Pseudomonas aeruginosa outer membrane protein F is an adhesin in bacterial binding to lung epithelial cells in culture," Microb. Pathog. (2002) 33(3):109-114.

Bajolet-Laudinat, O. et al., "Cytotoxicity of Pseudomonas aeruginosa internal lectin PA-I to respiratory epithelial cells in primary culture," Infect. Immun. (1994) 62(10):4481-4487.

Baker, A.K. et al., Functional effects of systemically administered agonists and antagonists of mu, delta, and kappa opioid receptor subtypes on body temperature in mice. J Pharmacol Exp Ther. Sep. 2002;302(3):1253-64.

Balasubramanian, S. et al., "Morphine sulfate inhibits hypoxia-induced vascular endothelial growth factor expression in endothelial cells and cardiac myocytes," J. Mol. Cell Cardiol. (2001) 33(12):2179-2187.

Baratti, C.M. et al., Brain opioid peptides may participate in the reversal of pentylenetetrazol-induced amnesia. Meth. Find Exp Clin Pharmacol. Sep. 1990;12(7):451-6.

Barie, P.S., "Surviving sepsis," Surg. Infect. (2004) 5:1-2.

Barlett, J.G., "HIV: current diagnosis, management and treatment options," HIV Disease Management Guide PDR (2004) 101-122.

Basilisco, G. et al., Effect of loperamide and naloxone on mouth-to-caecum transit time evaluated by lactulose hydrogen breath test. Gut. Jul. 1985;26(7):700-3.

Basilisco, G. et al., Oral naloxone antagonizes loperamide-induced delay of orocecal transit, Dig. Dis. Sci. Aug. 1987; 32(8):829-832.

Becker, P.M. et al., "Differential regulation of diverse physiological responses to VEGF in pulmonary endothelial cells," Am. J. Physiol. Lung Cell Mol. Physiol. (2001) 281:L1500-L1511.

Bedingfield, J.B. et al., Methylnaltrexone attenuates taste aversion conditioned by low-dose ethanol. Alcohol. Jan. 1998;15(1):51-4.

Belcheva, M.M. et al., "μ opioid transactivation and down-regulation of the epidermal growth factor receptor in astrocytes: implications for mitogen-activated protein kinase signaling," Mol. Pharmacol. (2003) 64(6):1391-1401.

Belcheva, M.M. et al., "μ-opioid receptor-mediated ERK activation involves calmodulin-dependent epidermal growth factor receptor transactivation," J. Biol. Chem. (2001) 276(36):33847-33853.

Bergsland et al., "Maximizing the Potential of Bevacizumab in Cancer Treatment," The Oncologist, 2004, vol. 9, suppl. 1, p. 36-42.

Berkes, J. et al., "Intestinal epithelial responses to enteric pathogens: effects on the tight junction barrier, ion transport, and inflammation," Gut (2003) 52:439-451.

Bertani, I. et al., "Role of GacA, LasI, RhlI, Ppk, PsrA, Vfr and ClpXP in the regulation of the stationary-phase sigma factor rpoS/RpoS in Pseudomonas," Arch Microbiol. (2003) 180:264-271.

Bianchetti, A. et al., Quaternary derivatives of narcotic antagonists: stereochemical requirements at the chiral nitrogen for in vitro and in vivo activity. Life Sci. 1983;33 Suppl 1:415-8.

Bianchi, G. et al., Quaternary narcotic antagonists' relative ability to prevent antinociception and gastrointestinal transit inhibition in morphine-treated rats as an index of peripheral selectivity. Life Sci. May 31, 1982;30(22):1875-83.

Bickel, M., Stimulation of colonic motility in dogs and rats by an enkephalin analogue pentapeptide. Life Sci. 1983;33 Suppl 1:469-72.

Bigliardi, P.I. et al., "Different expression of μ-opiate receptor in chronic and acute wounds and the effect of β-endorphin on transforming growth factor β type II receptor and cytokeratin 16 expression," J. Invest. Dermatol. (2003) 120:145-152.

Bigliardi-Qi, M. et al., "Changes of epidermal Mu-opiate receptor expression and nerve endings in chronic atopic dermatitis," Dermatology (2005) 210:91-99.

Birukov, K.G. et al., "Magnitude-dependent regulation of pulmonary endothelial cell barrier function by cyclic stretch," Am. J. Physiol. Lung Cell Mol. Physiol. (2003)285:L785-797.

Birukova, A.A. et al., "Role of Rho GTPases in thrombin-induced lung vascular endothelial cells barrier dysfunction," Microvascular Res. (2004) 67:64-77.

Blank, M.S. et al., Central, stereoselective receptors mediate the acute effects of opiate antagonists on luteinizing hormone secretion. Life Sci. Oct. 27, 1986;39(17):1493-99.

Blebea, J. et al., "Differential effects of vascular growth factors on arterial and venous angiogenesis," J. Vasc. Surg. (2002) 35(3):532-538.

Blebea, J. et al., "Opioid growth factor modulates angiogenesis," J. Vasc. Surg. (2000) 32(2):364-373.

Bogatcheva, N.V. et al., "Molecular mechanisms of thrombin-induced endothelial cell permeability," Biochemistry (2002) 67(1):75-84.

Bolin, I. et al., "Identification of Helicobacter pylori by immunological dot blot method based on reaction of a species-specific monoclonal antibody with a surface-exposed protein," J. Clin. Mirobiol. (1995) 33:381-384.

Bonn, D., "Morphine stimulates tumour growth," Lancet Oncology (2002) 3(9):520.

Boonstra, B. et al., "Engineering novel biocatalytic routes for production of semisynthetic opiate drugs," Biomol. Eng. (2001) 18:41-47.

Bowen, C.A. et al., Antagonism of the antinociceptive and discriminative stimulus effects of heroin and morphine by 3-methoxynaltrexone and naltrexone in rhesus monkeys. J Pharmacol Exp Ther. Jul. 2002;302(1):264-73.

Bowen, S.E. et al., College on Problems of Drug Dependence 64th Annual Scientific Meeting. Jun. 8-13, 2002. Quebec City, Quebec, Canada. Abstracts. Drug Alcohol Depend. May 1, 2002;66 Suppl 1:S19, Abstract No. 65.

Bradesi et al., "Inflammatory bowel disease and irritable bowel syndrome, separate or unified," Curr. Op. Gastroenterology (2003) 19:336-342.

Braun, F. et al., "Kinetics and localization of interleukin-2, interleukin-6, heat shock protein 70, and interferon gamma during intestinal-rerfusion injury," Transplant Proc. (2004) 36:267-269.

Breitbart, W. et al., "Control of non-pain symptoms in HIV/AIDS," J. Back Musculoskeletal Rehab. (1997) 8:243-246.

Brix-Christensen, V. et al., "Endogenous morphine levels increase following cardiac surgery as part of the antiinflammatory response," Int. J. Cardiol. (1997) 62:191-197.

Brix-Christensen, V. et al., Endogenous morphine is produced in response to cardiopulmonary bypass in neonatal pigs. Acta Anaesthesiol Scand. Nov. 2000;44(10):1204-8.

Brown, D.R. et al., Opiate antagonists: central sites of action in suppressing water intake of the rat. Brain Res. Sep. 28, 1981;221(2):432-6.

(56) References Cited

OTHER PUBLICATIONS

Brown, D.R. et al., Reversal of morphine-induced catalepsy in the rat by narcotic antagonists and their quaternary derivatives. Neuropharmacology. Mar. 1983;22(3):317-21.

Brown, D.R. et al., The use of quaternary narcotic antagonists in opiate research. Neuropharmacology. Mar. 1985;24(3):181-91.

Brown, L.F. et al., "Expression of vascular permeability factor (vaxcular endothelial growth factor) by epidermal keratinocytes during wound healing," J. Exp. Med. (1992) 176:1375-1379.

Brown, T.D. et al., Techniques for mechanical stimulation of cells in vitro: a review. J Biomech. Jan. 2000;33(1):3-14.

Bruce, N.C. et al., "Microbial degradation of the morphine alkaloids: identification of morphine as an intermediate in the metabolism of morphine by Pseudomonas putida M10," Arch Microbiol. (1990) 154:465-470.

Caballero-Hernandez, D. et al., "Potentiation of rat lymphocyte proliferation by novel non-peptidic synthetic opioids," Int. Immunopharmacol. (2005) 5(7-8):1271-1278.

Cadet, M. et al., "Molecular identification and functional expression of 3, a novel alternative spliced variant of the human µ opiate receptor gene," J. Immunol (2003) 170:5118-5123.

Cadet, P. et al., "Differential expression of the human µ opiate receptor from different primary vascular endothelial cells," Med. Sci. Monit. (2004) 10(10):BR351-355.

Calcagnetti, D.J. et al., Quaternary naltrexone reveals the central mediation of conditional opioid analgesia. Pharmacol Biochem Behay. Jul. 1987;27(3):529-31.

Calfee, M.W. et al., "Interference with pseudomonas quinolone signal synthesis inhibits virulence factor expression by pseudomonas aeruginosa," Proc. Natl. Acad. Sci. USA (2001) 98(20):11633-11637.

Camilleri, M. et al., "Effect of a selective chloride channel activator, lubiprostone, on gastrointestinal transit, gastric sensory, and motor functions in healthy volunteers," Am. J. Physiol. (2006) 290:G942-947.

Cao, C.M. et al., "Cardioprotection of interleukin-2 is mediated via K-opioid receptors," J. Pharmacol. Exp. Ther. (2004) 309:560-567.

Carmeliet, P. et al., "Angiogenesis in cancer and other diseases," Nature (2000) 407:249-257.

Carr, A., "Improvement of the study, analysis, and reporting of adverse events associated with antiretroviral therapy," Lancet (2002) 360:81-85.

Carr, D.J.J. et al., Naltrexone antagonizes the analgesic and immunosuppressive effects of morphine in mice. J Pharmacol Exp Ther. May 1994;269(2):693-8.

Cascone, I. et al., "Tie-2-dependent activation of RhoA and Rac1 participates in endothelial cell motility triggered by angiopoietin-1," (2003) 102(7):2482-2490.

Chancey, S.T. et al., "Two-component transcriptional regulation of N-acyl-homoserine lactone production in pseudomonas aureofaciens," Appl. Environ. Microbiol. (1999) 65:2294-2299.

Chang, E.B. et al., an antiabsorptive basis for precipitated withdrawal diarrhea in morphine-dependent rats. J Pharmacol Exp Ther. Feb. 1984;228(2):364-9.

Chang, S.L. et al., "Morphine affects the brain-immune axis by modulating an interleukin-1 β dependent pathway," In: AIDS, Drugs of Abuse and the Neuroimmune Axis, New York, Plenum Publishing Corp., Friedman et al. eds. (1996) 35-42.

Chang, S.L. et al., "The association between opiates and cytokines in disease," Adv. Exp. Med. Biol. (1998) 437:4-6.

Chen, C. et al., "Catecholamines modulate *Escherichia coli* O157:H7 adherence to murine cecal mucosa," Shock (2003) 20:183-188.

Chen, C. et al., "Morphine stimulates vascular endothelial growth factor-like signaling in mouse retinal endothelial cells," Curr. Neurovas. Res. (2006) 3:171-180.

Chiu, H.H. et al., "Bacteremia and fugemia in hematological and oncological children with neutropenic fever: two-year study in a medical center," J. Microbiol. Immunol. Infect. (1998) 31:101-106.

Choi, Y.S. et al., Inhibition of chemokine-induced chemotaxis of monkey leukocytes by mu-opioid receptor agonists. In Vivo. Sep.-Oct. 1999;13(5):389-96.

Choi, Y.S. et al., Opioid antagonists: a review of their role in palliative care, focusing on use in opioid-related constipation. J Pain Symptom Manage. Jul. 2002;24(1):71-90. Review.

Cioci, G. et al., "Structural basis of calcium and galactose recognition by the lectin PA-IL of Pseudomonas aeruginosa," FEBS Left. (2003) 555:297-301.

Clark, N.M. et al, "Antimicrobial resistance among gram-negative organisms in the intensive care unit," Curr. Opin. Crit. Care (2003) 9:413-423.

Clauser, K.R. et al., "Role of accurate mass measurement (+/− 10 ppm) in protein identification strategies employing MS or MS/MS and database searching," Anal. Chem. (1999) 71:2871-2882.

Collins, S.L. et al., "Peak plasma concentrations after oral morphine: a systematic review," J. Pain Symptom Management (1998) 16(6):388-402.

Cozzolino, D. et al., "Acute effects of β-endorphin on cardiovascular function in patients with mild to moderate chronic heart failure," Am. Heart J. (2004) 148(E13):1-7.

Crawford, S. et al., "A deletion mutation in the 5' part of the pol gene of Moloney murine leukemia virus blocks proteolytic processing of the gag and pol polyproteins," J. Virol. (1985) 53:899-907.

Culpepper-Morgan, J.A. et al., Treatment of opioid-induced constipation with oral naloxone: a pilot study. Clin Pharmacol Ther. Jul. 1992;52(1):90-5 Abstract.

Dancik, V. et al., "De novo peptide sequencing via tandem mass spectrometry," J. Comput. Biol. (1999) 6:327-342.

Davies, A.G. et al., "A central role of the BK potassium channel in behavioral responses to ethanol in C. elegans," Cell (2003) 115:655-666.

Davies, A.G. et al., "Natural variation in the npr-1 gene modifies ethanol responses of wild strains of C. elegans," Neuron. (2004) 42:731-743.

Davies, A.G. et al., "Using C. elegans to screen for targets of ethanol and behavior-altering drugs," Biol. Proced. Online (2004) 6:113-119.

De Jonge, E. et al., "Effects of selective decontamination of digestive tract on mortality and acquisition of resistant bacteria in intensive care: a randomised controlled trial," Lancet (2003) 362:1011-1016.

De Kievit, T.R. et al., "Quorum-sensing genes in pseudomonas aeruginosa biofilms: their role and expression pattern," App. Environ. Microbiol. (2001) 67:1865-1873.

De Kievit, T.R. et al., "Role of the pseudomonas aeruginosa las and rhl quorum-sensing systems in rhlI regulation," FEMS Microbiol. Lett (2002) 212:101-106.

De Ponti, F. et al., Methylnaltrexone Progenies. Curr Opin Investig Drugs. Apr. 2002;3(4):614-20. Review.

Dechelotte, A. et al., "Uptake, 3-, and 6-glucuronidation of morphine in isolated cells from stomach, intestine, colon, and liver of the guinea pig," Drug Metab. Dispos. (1993) 21:13-17.

Denissen, J.F. et al., "Metabolism and disposition of the HIV-1 protease inhibitor ritonavir (ABT-538) in rats, dogs, and humans," Drug Metab. Dispos. (1997) 25:489-501.

Deziel, E. et al., "Analysis of pseudomonas aeruginosa 4-hydroxy-2-alkylquinolines (HAQs) reveals a role for 4-hydroxy-2-heptylquinoline in cell-to-cell communication," Proc. Natl. Acad. Sci USA (2004) 101:1339-1344.

Diggle, S.P. et al., "Advancing the quorum in Pseudomonas aeruginosa: MvaT and the regulation of N-acylhomoserine lactone production and virulence gene expression," J. Bacteriol. (2002) 184:2576-2586.

Diggle, S.P. et al., "The Pseudomonas aeruginosa quinolone signal molecule overcomes the cell density-dependency of the quorum sensing hierarchy, regulates rhl-dependent genes at the onset of stationary phase and can be produced in the absence of LasR," Mol. Microbiol. (2003) 50:29-43.

Doherty, M.M et al., "Route-dependent metabolism of morphine in the vascularly perfused rat small intestine preparation," Pharm. Res. (2000) 17(3):291-298.

(56) References Cited

OTHER PUBLICATIONS

Dudek, S.M. et al., "Cytoskeletal regulation of pulmonary ascular permeability," J. Appl. Physiol. (2001) 91:1487-1500.

Dunlap, P.V., "Quorum regulation of luminescence in vibrio fischeri," J. Mol. Microbiol. Biotechnol. (1999) 1:5-12.

Egan, T.D. et al., Prospective pharmacokinetic and pharmacodynamic validation of propofol's context sensitive T1/2. Anesthesiology. Sep. 1999;91(3A): Abstract A347.

Eisenberg, R.M., Effects of naltrexone on plasma corticosterone in opiate-naive rats: a central action. Life Sci. Mar. 19, 1984;34(12):1185-91.

Eisenstein, K et al., "Effect of opioids on oral salmonella infection and immune function," Adv. Exp. Med. Biol. (2001) 493:169-176.

Elperin, A. et al., "A patient's guide to protease inhibitors," AIDS Clin. Care (1996) 8:83-84.

Epstein, A.M. et al., "Naltrexone attenuates acute cigarette smoking behavior," Pharmacology Biochem. Behavior (2004) 77(1):29-37.

Ernest, C.S. et al., "Mechanism-based inactivation of CYP3A by HIV protease inhibitors," J. Pharmacol. Exp. Ther. (2005) 312:583-591.

Esposito, S. et al, "Bacterial infections in intensive care units: etiology and pathogenesis," Infez. Med. (1997) 5:145-159.

Essar, D.W. et al., "Identification and characterization of genes for a second anthranilate synthase in pseudomonas aeruginosa: interchangeability of the two anthranilate synthases and evolutionary implications," J. Bacteriol. (1990) 172:884-900.

Exadaktylos, A.K. et al., Can anesthetic technique for primary breast cancer surgery affect recurrence or metastatis? Anesthesiology (2006) 105:660-664.

Fagerlind, M.G. et al., "The role of regulators in the expression of quorum-sensing signals in Pseudomonas aeruginosa," J. Mol. Microbiol. Biotechnol. (2004) 6:88-100.

Farooqui, M. et al., "Mu opioid receptor stimulates a growth promoting and pro-angiogenic tumor microenvironment," Proc. Amer. Assoc. Cancer Res. (2005) 46:Abstract #4650, AACR Meeting Abstracts.

Farooqui, M. et al., "Naloxone acts as an antagonist of estrogen receptor in MCF-7 cells," Mol. Cancer Ther. (2006) 5(3):611-620.

Farthing, M.J.G. et al., New drugs in the management of the irritable bowel syndrome. Drugs. Jul. 1998;56(1):11-21.

Faura, C.C. et al., "Systematic review of factors affecting the ratios of morphine and its major metabolites," Pain (1998) 74:43-53.

Feistritzer et al., "Endothelial barrier protection by activated protein C through PAR1-dependent sphingosine 1-phosphate receptor-1 crossactivation," Blood (2005) 105(8):3178-3184.

Fenchel, T., "Microbial behavior in a heterogeneous world," Science (2002) 296:1068-1071.

Fernandez-Tome, M.P. et al., Interaction between opioid agonists or naloxone and 5-HTP on feeding behavior in food-deprived rats. Pharmacol Biochem Behav. Feb. 1988;29(2):387-92.

Fernando et al., "Inhibition of Vascular Endothelial Growth Factor in the Treatment of Colorectal Cancer," Seminars in Oncology, Jun. 2003, vol. 30, issue 3, supplement 6, pp. 39-50.

Ferrer, F.A. et al., "Angiogenesis and prostate cancer: in vivo and in vitro expression of angiogenesis factors by prostate cancer cells," Urology (1998) 51:161-167.

Fingl, E. et al., Chapter 43: Laxatives and cathartics. In Pharmacological Basis of Therapeutics. 1980: 1002-1012.

Finigan, J.H. et al., "Activated protein C mediates novel lung endothelial barrier enhancement," J. Biol. Chem. (2005) 280(17):17286-17293.

Finn, A.K. et al., "Endocytosis of the mu opioid receptor reduces tolerance and a cellular hallmark of opiate withdrawal," Neuron. (2001) 32:829-839.

Fleiszig, S.M. et al., "Pseudomonas aeruginosa-mediated cytotoxicity and invasion correlate with distinct genotypes at the loci encoding exoenzyme S," Infect. Immun. (1997) 65:579-586.

Flores, L.R. et al., Mechanisms of morphine-induced immunosuppression: effect of acute morphine administration on lymphocyte trafficking. J Pharmacol Exp Ther. Mar. 1995;272(3):1246-51.

Foss, J. et al., "Alvimopan (ENTEREG), a novel opioid antagonist, achieves active systemic concentrations," Amer. Soc. Clin. Pharma & Thera. (2005) PII-90, p. 74.

Foss, J.F. et al., "Methylnaltrexone does not antagonize the analgesic effect of morphine: a clinical study," (1995) ASA Abstracts, Annual Scientific Meeting of the American Society of Anesthesiologists, Atlanta, Georgia, Oct. 21-25, 1995, 83(3A Suppl):A361.

Foss, J.F. et al., Dose-related antagonism of the emetic effect of morphine by methylnaltrexone in dogs. J Clin Pharmacol. Aug. 1993;33(8):747-51.

Foss, J.F. et al., Effects of methylnaltrexone on morphine-induced cough suppression in guinea pigs. Life Sci. 1996;59(15):PL235-8.

Foss, J.F. et al., Enteric-coated methylnaltrexone prevents opioid-induced oral-cecal transit delay in humans. Anesth Analg. 2000;90. Abstract S409.

Foss, J.F. et al., Methylnaltrexone reduces morphine-induced postoperative emesis by 30%. Anesth Analg. 1994;78:S119.

Foss, J.F. et al., Prevention of apomorphine- or cisplatin-induced emesis in the dog by a combination of methylnaltrexone and morphine. Cancer Chemother Pharmacol. 1998;42(4):287-91.

Foss, J.F. et al., Safety and tolerance of methylnaltrexone in healthy humans: a randomized, placebo-controlled, intravenous, ascending-dose, pharmacokinetic study. J Clin Pharmacol. Jan. 1997;37(1):25-30.

Foss, J.F. et al., Subcutaneous methylnaltrexone reduces morphine-induced subjective effects in humans. Anesthesiology. 2001;95. Abstract A-817.

Foss, J.F. et al., The efficacy or oral methylnaltrexone in decreasing the subjective effects of IV morphine. Anesth Analg. 1997;84. Abstract S484.

Foss, J.F., A review of the potential role of methylnaltrexone in opioid bowel dysfunction. Am J Surg. Nov. 2001;182(5A Suppl):19S-26S.

Fox, J.G. et al., "Host and microbial constituents influence Helicobacter pylon-induced cancer in a murine model of hypergastrinemia," Gastroenterology (2003) 124:1879-1890.

France, C.P. et al., Comparison of naltrexone and quaternary naltrexone after systemic and intracerebroventricular administration in pigeons. Neuropharmacology. Jun. 1987;26(6):541-8.

France, C.P. et al., Intracerebroventricular drug administration in pigeons. Pharmacol Biochem Behay. Nov. 1985;23(5): 731-6.

France, C.P. et al., Morphine, saline and naltrexone discrimination in morphine-treated pigeons. J Pharm and Exper Ther. 1987;242:195-202.

Frassdorf, J. et al., "Morphine induces late cardioprotection in rat hearts in vivo: the involvement of opioid receptors and nuclear transcription factor-κB," Anesth. Analg. (2003) 101:934-941.

French, C.E. et al., "Purification and characterization of morphinone reductase from Pseudomonas putida M10," Biochem. J. (1994) 301 (Pt. 1):97-103.

Frich, L.M. et al., "Pain and pain treatment in AIDS patients: a longitudinal study," J. Pain Symptom Manage (2000) 19:339-347.

Friedman, J.D. et al., "Opioid antagonists in the treatment of opioid-induced constipation and pruritus," Ann. Pharmacother. (2001) 35(1):85-91.

Funke, C.W. et al., A proton and carbon-13 nuclear magnetic resonance study of three quaternary salts of naloxone and oxymorphone. J Chem Soc. 1986:735-8.

Furuta, G.T. et al., "Hypoxia-inducible factor 1-dependent induction of intestinal trefoil factor protects barrier function during hypoxia," J. Exp. Med. (2001) 193:1027-1034.

Gainor, J.P. et al., "Platelet-conditioned medium increases endothelia electrical resistance independently of cAMP/PKA and cGMP/PKG," Am. J. Physiol. Heart Circ. Physiol. (2001) 281:H1992-2001.

Garcia, J.G.N. et al., "Diperoxovanadate alters endothelial cell focal contacts and barrier function: role of tyrosine phosphorylation," J. Appl. Physiol. (2000) 89:2333-2343.

Garcia, J.G.N. et al., "Mechanisms of ionomycin-induced endothelial cell barrier dysfunction," Am. J. Physiol. (1997) 273:L172-L184.

(56) References Cited

OTHER PUBLICATIONS

Garcia, J.G.N. et al., "Spingosine 1-phosphate promotes endothelial cell barrier integrity by Edg-dependent cytoskeletal rearrangement," J. Clin. Invest. (2001) 108(5):689-701.

Gartland, M. "AVANTI 3: a randomized, double-blind trial to compare the efficacy and safety of lamivudine plus zidovudine versus lamivudine plus zidovudine plus nelfinavir in HIV-1 infected antiretroviral-nalve patients," Antivir. Ther. (2001) 6:127-134.

Gervitz, C., "Targeted approach: methylnaltrexone blocks opioid-induced constipation and other peripheral side effects," Topics in Pain Management (2005) 21(1):6-8.

Giles, T. et al., Quaternary opiate antagonists lower blood pressure and inhibit leucine-enkephalin responses. Eur J Pharmacol. Nov. 25, 1983;95(3-4):247-52.

Glick, J. et al., "The intracellular localization of Pseudomonas aeruginosa lectins," J. Gen. Microbiol. (1983) 129(Pt 10):3085-3090.

Gmerek, D.E. et al., Independent central and peripheral mediation of morphine-induced inhibition of gastrointestinal transit in rats. J Pharmacol Exp Ther. Jan. 1986;236(1):8-13.

Golden, T.R. et al., "Oxidative stress and aging: beyond correlation," Aging Cell (2002) 1:117-123.

Goodman, A.L. et al., "Analysis of regulatory networks in Pseudomonas aeruginosa by genomewide transcriptional profiling," Curr. Opin. Microbiol. (2004) 7:39-44.

Goumon, Y. et al., "Ascaris suum, an intestinal parasite, produces morphine," J. Immunol (2000) 165:339-343.

Gouvea, E.F. et al., "Outcome of infections caused by multiple drug-resistant bacteria in liver transplant recipients," Transplant Proc. (2004) 36:958-960.

Granata, F. et al., "Expression of OP4 (ORL1, NOP1) receptors in vascular endothelium," Eur. J. Pharmacol. (2003) 482:17-23.

Griffith, S.J. et al., "The epidemiology of Pseudomonas aeruginosa in oncology patients in a general hospital," J. Infect. Dis. (1989) 160:1030-1036.

Gupta, K. et al., "Angiogenesis: a curse or cure?" Postgrad Med. J. (2005) 81:236-242.

Gupta, K. et al., "Morphine exaggerates retinopathy in transgenic sickle mice," Blood (ASH Annual Meeting Abstract) (2005) 106:Abstract 209.

Gupta, K. et al., "Morphine mimics VEGF in vascular endothelium, by promoting pro-angiogenic and survival promoting signalling and angiogenesis," FASEB Journal (2002) 16(4):A207 and Annual Meeting of the Professional Research Scientists on Experimental Biology; New Orleans, Louisiana, Apr. 20-24, 2002 (Abstract only).

Gupta, K. et al., "Morphine stimulates angiogenesis by activating proangiogenic and survival-promoting signaling and promotes breast tumor growth," Cancer Res. (2002) 62(15):4491-4498.

Gupta, R.A. et al., "Activation of peroxisome proliferator-activated receptor gamma suppresses nuclear factor kappa B-mediated apoptosis induced by Helicobacter pylori in gastric epithelial cells," J. Biol. Chem. (2001) 276(33):31059-31066.

Gutstein, D.E. et al., Role of inositol 1,4,5-trisphosphate receptors in regulating apoptotic signaling and heart failure. Heart Vessels. 1997;Suppl 12:53-7.

Guy, H.R. et al., "Structural models of Na+, Ca2+, and K+ channels," Ion Channels and Genetic Diseases, Chapter 1, (1995) 1-28.

Hailes, A.M. et al., "Biological synthesis of the analgesic hydromorphone, an intermediate in the metabolism of morphine, by Pseudomonas putida M10," App. Environ. Microbiol. (1993) 59:2166-2170.

Hainsworth et al., "Paclitaxel by 1-hour infusion: an active drug in metastic non-small-cell lung cancer," Journal of Clinical Oncology, 1995, vol. 13, No. 7, pp. 1609-1614.

Hamoudeh et al., "Paclitaxel-loaded microparticles for Intratumoral Administration via the TMT Technique: Preparation, Characterization, and Preliminary Anittumoral Evaluation," Drug Development and Industrial Pharmacy, 2008, vol. 34, No. 7, pp. 698-707.

Hanif, K. et al., "Hypotensive effect of novel chimeric peptides of met-enkephalin and FMRFa," Regul. Pept. (2005) 125:155-161.

Hawkes, N.D. et al., "Naloxone treatment for irritable bowel syndrome—a randomized controlled trial with an oral formulation," Aliment Pharmacol. Ther. (2002) 16:1649-1654.

Hein, D.W. et al., Pharmacological analysis of the discriminative stimulus characteristics of ethylketazocine in the rhesus monkey. J Pharmacol Exp Ther. Jul. 1981;218(1):7-15.

Hellewell, S.B. et al., "A sigma-like binding site in rat pheochromocytoma (PC12) cells: decreased affinity for (+)-benzomorphans and lower molecular weight suggest a different sigma receptor form from that of guinea pig brain," Brain Res. (1990) 527:244-253.

Hendrickson, E.L. et al., "Differential roles of the Pseudomonas aeruginosa PA14 rpoN gene in pathogenicity in plants, nematodes, insects, and mice," J. Bacteriol. (2001) 183:7126-7134.

Hicks, M.E. et al., Differential effects of the novel non-peptidic opioid 4-tyrosylamido-6-benzyl-1,2,3,4 tetrahydroquinoline (CGPM-9) on in vitro rat t lymphocyte and macrophage functions. Life Sci. May 4, 2001;68(24):2685-94.

Hirota, H. et al., Loss of a gp130 cardiac muscle cell survival pathway is a critical event in the onset of heart failure during biomechanical stress. Cell. Apr. 16, 1999;97(2):189-98.

Ho, C.L. et al., Beta-endorphin: peripheral opioid activity of homologues from six species. Int J Pept Protein Res. Apr. 1987;29(4):521-4.

Ho, W.K.K. et al., Suppression of immunological functions in morphine addicted mice. NIDA Res Monogr. 1986;75:599-602.

Ho, W-Z. et al., "Methylnaltrexone antagonizes opioid-mediated enhancement of HIV infection of human blood mononuclear phagocytes," J. Pharm. Exp. Thera. (2003) 307:1158-1162.

Hoang, M.V. et al., "Rho activity critically and selectively regulates endothelial cell organization during angiogenesis," (2004) 101(7): 1874-1879.

Hofmann, P. et al., Hypocalcemia during restraint stress in rats. Indication that gastric ulcer prophylaxis by exogenous calcium interferes with calcitonin release. Res Exp Med (Berl). May 30, 1979;175(2):159-68.

Holzer, P., "Opioids and opioid receptors in the enteric nervous system: from a problem in opioid analgesia to a possible new prokinetic therapy in humans," Neurosci. Lett. (2004) 361:192-195.

Hou, Y.N. et al., "A μ-receptor opioid agonist induces AP-1 and NF-κB transcription factor activity in primary cultures of rat cortical neurons," Neurosci. Lett. (1996) 212:159-162.

Howd, R.A. et al., Naloxone and intestinal motility. Experientia. Oct. 15, 1978;34(10):1310-1.

http://opioids.com/opiates.html, "Endogenous opioids," (Nov. 6, 2007) 4 pages.

Hussain, M.A. et al., Improvement of the oral bioavailability of naltrexone in dogs: a prodrug approach. J Pharm Sci. May 1987;76(5):356-8.

Hussain, M.A. et al., Naltrexone-3-salicylate (a prodrug of naltrexone): synthesis and pharmacokinetics in dogs. Pharm Res. Feb. 1988;5(2):113-5.

Iorio, M.A. et al., Narcotic agonist/antagonist properties of quaternary diastereoisomers derived from oxymorphone and naloxone. Eur J Med Chem. 1984;19(4):301-3.

Jacobs, M.A. et al., "Comprehensive transposon mutant library of Pseudomonas aeruginosa," Proc. Natl. Acad. Sci. USA (2003) 100:14339-14344.

Jalowiec, J.E. et al., Suppression of juvenile social behavior requires antagonism of central opioid systems. Pharmacol Biochem Behav. Jul. 1989;33(3):697-700.

Jankovic, B.D. et al., Quaternary naltrexone: its immunomodulatory activity and interaction with brain delta and kappa opioid receptors. Immunopharmacology. Sep.-Oct. 1994;28(2):105-12.

Jenab, S. et al., "Ethanol and naloxone differentially upregulate delta opioid receptor gene expression in neuroblastoma hybrid (NG108-15) cells," Brain Res. Mol. Brain Res. (1994) 27:95-102.

Johanson, J.F. et al., "Lubiprostone, a locally acting chloride channel activator, in adult patients with chronic constipation: a double-blind, placebo-controlled, dose-ranging study to evaluate efficacy and safety," Aliment Pharm. Ther. (2007) 25:1351-1361.

(56) References Cited

OTHER PUBLICATIONS

Juhas, M. et al., "Global regulation of quorum sensing and virulence by VqsR in Pseudomonas aeruginosa," Microbiology (2004) 150:831-841.
Kakeji, Y. et al., "Preclinical studies of the combination of angiogenic inhibitors with cytotoxic agents," Invest. New Drugs (1997) 15:39-48.
Karhausen, J. et al., "Implications of hypoxia on mucosal barrier function," Cell Mol. Biol. (2003) 49:77-87.
Kasamatsu, K. et al., "Attenuation of aortic baroreflex responses by microinjections of endomorphin-2 into the rostral ventrolateral medullary pressor area of the rat," Am. J. Physiol. Regul. Integr. Comp. Physiol. (2005) 289:R59-R67.
Katoh, I. et al., "Murine leukemia virus maturation: protease region required for conversion from 'immature' to 'mature' core form and for virus infectivity," Virology (1985) 145:280-292.
Kaufman, P.N. et al., Role of opiate receptors in the regulation of colonic transit. Gastroenterology (1988) 94(6): 1351-6.
Kehlet, H. et al., Review of postoperative ileus. Am J Surg. Nov. 2001;182(5A Suppl):3S-10S. Review.
Kim, C. et al., Assay for methylnaltrexone in rat brain regions and serum by high-performance liquid chromatography with coulometric electrochemical detection. Chromatographia. Oct. 1989;28(7-8):359-63.
King, A.C. et al., "Hypothalamic-pituitary-adrenocortical (HPA) axis response and biotransformation of oral naltrexone: preliminary examination of relationship to family history of alcoholism," Neuropsychopharmacology (2002) 26(6):778-788.
Kinsman, R.I. et al., Effect of naloxone on feedback regulation of small bowel transit by fat. Gastroenterology. Aug. 1984;87(2):335-7.
Kirkeby, S. et al., "Lectin interactions with alpha-galactosylated xenoantigens," Xenotransplantation (2002) 9:260-267.
Ko, M.C.H. et al., "Orphanin FQ inhibits capsaicin-induced thermal nociception in monkeys by activation of peripheral ORL1 receptors," Bri. J. Pharmacol. (2002) 135:943-950.
Koblish, M. et al., Behavioral profile of ADL 8-2698, a novel GI-restricted μ opioid receptor antagonist. Society for Neuroscience Abstracts. 2001;27(2):2407.
Kobylecki, R.J. et al., N-Methylnalorphine: definition of N-allyl conformation for antagonism at the opiate receptor. J Med Chem. Nov. 1982;25(11):1278-80.
Koch, B. et al., "Lipopeptide production in *Pseudomonas* sp. strain DSS73 is regulated by components of sugar beet seed exudate via the Gac two-component regulatory system," Appl. Environ, Microbiol. (2002) 68:4509-4516.
Koczka, K. et al., "Selective quarternization of compounds with morphine skeleton," Acta Chimica Academica Scien. Hung. (1967) 51(4), 393-02.
Kodani, E. et al., "δ opioid receptor-induced late preconditioning is mediated by cyclooxygenase-2 in conscious rabbits," Am. J. Physiol. Heart Circ. Physiol. (2002) 283:H1943-H1957.
Kohler et al., "Components of intestinal epithelial hypoxia activate the virulence circuitry of Pseudomonas," Amer. J. Physio. Gastrointest Liver Physiol. (2005) 288:1048-1054.
Koob, G.F. et al., Effects of opiate antagonists and their quaternary derivatives on heroin self-administration in the rat. J Pharmacol Exp Ther. May 1984;229(2):481-6.
Kosten, T.A. et al., Naltrexone and morphine alter the discrimination and plasma levels of ethanol. Behav Pharmacol. Feb. 1999;10(1):1-13.
Kostic, T., "The effect of opioid antagonists in local regulation of testicular response to acute stress in adult rats," CAS Abstract Document No. 127: 13345, 1997.
Kotake, A.N. et al., "Variations in demethylation of N-methylnaltrexone in mice, rats, dogs, and humans," Xenobiotica (1989) 19(11):1247-1254.
Kreek, M.J. et al., "Naloxone, a specific opioid antagonist, reverses chronic idiopathic constipation," Lancet (1983) 261-262.

Kromer, W. et al., Endogenous opioids, the enteric nervous system and gut motility. Dig Dis. 1990;8(6):361-73.
Kromer, W. et al., The current status of opioid research on gastrointestinal motility. Life Sci. 1989;44(9):579-89.
Kropec, A. et al., "Exogenous or endogenous reservoirs of nosocomial Pseudomonas aeruginosa and *Staphylococcus aureus* infections in a surgical intensive care unit," Intensive Care Med. (1993) 19:161-165.
Kurahashi, K. et al., "Pathogenesis of septic shock in Pseudomonas aeruginosa pneumonia," J. Clin. Invest. (1999) 104:743-750.
Lai, H.P. et al., "Bacteremia in hematological and oncological children with febrile neutropenia: experience in a tertiary medical center in Taiwan," J. Microbiol. Immunol Infect. (2003) 36:197-202.
Lau, G.W. et al., "Pseudomonas aeruginosa pyocyanin is critical for lung infection in mice," Infect. Immun. (2004) 72(7):4275-4278.
Laughlin, R.S. et al., "The key role of Pseudomonas aeruginosa PA-I lectin on experimental gut-derived sepsis," Ann. Surg. (2000) 232:133-142.
Law, P.Y. et al., "Agonist activation of δ-opioid receptor but not μ-opioid receptor potentiates fetal calf serum or tyrosine kinase receptor-mediated cell proliferation in a cell-line-specific manner," Mol. Pharmacol. (1997) 51:152-160.
Law, P.Y. et al., "Properties of delta opioid receptor in neuroblastoma NS20Y: receptor activation and neuroblastoma proliferation," J. Pharmacol. Exp. Ther. (1995) 272(1):322-332.
Law, P.Y. et al., "Regulation of opioid receptor activities," J. Pharmacol. Exp. Ther. (1999) 289:607-624.
Leander, J.D., A kappa opioid effect: increased urination in the rat. J Pharmacol Exp Ther. Jan. 1983;224(1):89-94.
Ledgham, F. et al., "Interactions of the quorum sensing regulator QscR: interaction with itself and the other regulators of Pseudomonas aeruginosa LasR and Rh1R," Mol. Microbiol. (2003) 48:199-210.
Li, Y. et al., Methadone enhances human immunodeficiency virus infection of human immune cells. J Infect Dis. Jan. 1, 2002;185(1):118-22. Epub Dec. 14, 2001.
Lichterfeld, M. et al., "Long-term efficacy and safety of ritonavir/indinavir at 400/400 mg twice a day in combination with two nucleoside reverse transcriptase inhibitors as first line antiretroviral therapy," HIV Med. (2002) 3:37-43.
Lim, Y.J. et al., "Morphine preconditions Purkinje cells against cell death under in vitro simulated ischemia-reperfusion conditions," Anesthesiol. (2004) 100(3):562-568.
Lingen, M.W., "Endothelial Cell Migration Assay. A Quantitative Assay for Prediction of In Vivo Biology," Methods in Molecular Medicine, Wound Healing, Methods and Protocols (2003) 78:337-347.
Linn, A.J. et al., "Peripherally restricted μ-opioid receptor antagonists: a review," Techniques in Regional Anesthesia and Pain Management (2007) 11:27-32.
Little, P.J.et al., ADL 8-2698, a GI restricted opioid antagonist, blocks the antisecretory and colorectal transit effects of morphine and loperamide. Society for Neuroscience Abstracts. 2001; 27(2):2407. Abstract.
Liu, Y. and Senger, D.R., "Matrix-specific activation of Src and Rho initiates capillary morphogenesis of endothelial cells," FASEB J. (2004) 18:457-468.
Livermore, D.M., "The threat from the pink corner," Ann. Med. (2003) 35:226-234.
Livingston, E.H. et al., Postoperative ileus. Dig Dis Sci. Jan. 1990;35(1):121-32.
Lopez, Y. et al., Demonstration of long-lasting blockade of experimental ileus in rats by an opioid k-agonist. Gastroenterology. 1995;108(4):A640. Abstract.
Lory, S. et al., "The multi-talented bacterial adenylate cyclases," Int. J. Med. Microbiol. (2004) 293:479-482.
Lydon, A. et al., "Intravenous methylnaltrexone attenuates intrathecal morphine induced delayed gastric emptying in rats," ESA Free Paper Prize Competition. Eur J Anaesthesiol. Apr. 2001;18 Suppl 21:92, Abstract A-327.

(56) References Cited

OTHER PUBLICATIONS

Lysle, D.T. et al., Modulation of immune status by a conditioned aversive stimulus: evidence for the involvement of endogenous opioids. Brain Behav Immun. Jun. 1992;6(2):179-88.
Lyte, M. et al., "Stimulation of *Staphylococcus epidermidis* growth and biofilm formation by catecholamine inotropes," Lancet (2003) 361:130-135.
Machelska, H. et al., "Selectins and integrins but not platelet-endothelial cell adhesion molecule-1 regulate opioid inhibition of inflammatory pain," Br. J. Pharmacol. (2004) 142:772-780.
Mack, D.J. et al., Paralytic ileus: response to naloxone. Br J Surg. Oct. 1989;76(10):1101.
Magazine, H.I. et al., "Morphine-induced conformational changes in human monocytes, granulocytes, and endothelial cells and in invertebrate immunocytes and microglia are mediated by nitric oxide," J. Immunol (1996) 156:4845-4850.
Magnan, J. et al., the binding spectrum of narcotic analgesic drugs with different agonist and antagonist properties. Naunyn Schmiedebergs Arch Pharmacol. Jun. 1982;319(3):197-205.
Manara, L. et al., Peripheral selectivity of quaternary narcotic antagonists: relative ability to prevent gastrointestinal transit inhibition and antinociception in morphinized rats. Adv. Endog. Exog. Opioids, 12th Proc. Int. Narc. Res. Conf., Kyoto, Japan(1981): 402-4.
Manara, L. et al., The central and peripheral influences of opioids on gastrointestinal propulsion. Annu Rev Pharmacol Toxicol. 1985;25:249-73.
Marmor, M. et al., "Coronary artery disease and opioid use," Am. J. Cardiol. (2004) 93:1295-1297.
Marshall, J.C. et al., "The ecology and immunology of the gastrointestinal tract in health and critical illness," J. Hosp. Infect. (1991) 19 Suppl. C:7-17.
Marshall, J.C. et al., "The gastrointestinal tract. The 'undrained abcess' of multiple organ failure," Ann. Surg. (1993) 218:111-119.
Matsko, N. et al., "AFM of biological material embedded in epoxy resin," J. Struct. Biol. (2004) 146:334-343.
Matta, H. et al., "An immuno-dot blot assay for detection of thermostable protease from *Pseudomonas* sp. AF-36 of dairy origin," Lett. Appl. Microbiol. (1997) 25:300-302.
Mavrodi, D.V. et al., "Functional analysis of genes for biosynthesis of pyocyanin and phenazine-1-carboxamide from pseudomonas aeruginosa PAO1," J. Bacteriol. (2001) 183:6454-6465.
McBride, S.M. et al., "$\delta_2$ opioid receptor agonist facilitates mean arterial pressure recovery after hemorrhage in conscious rats," Shock (2005) 23(3):264-268.
McCance-Katz, E.F. et al., "Interactions between buprenorphine and antiretrovirals. I. The protease inhibitors Nelfinavir, Lopinavir/Ritonavir, and Ritonavir," Clinical Infect. Diseases (2006) 43:S235-S246.
McCarthy, R.N. et al., Preliminary studies on the use of plasma β-endorphin in horses as an indicator of stress and pain. J Equine Vet Sci. 1993;13(4):216-9.
McKnight, S.L. et al., "The pseudomonas quinolone signal regulates rhl quorum sensing in pseudomonus aeruginosa," J. Bacteriol. (2000) 182:2702-2708.
McQuay, H.J., "Opioid problems and morphine metabolism and excretion," taken from http://www.jr2.ox.ac.uk/bandolier/booth/painpag/wisdorn/c14.html (Oct. 26, 2005) 34 pages.
McQuay, H.J., "Opioid use in chronic pain," Acta Anaesthesiol. Scand. (1997) 41:175-183.
McVerry, B.J. et al., "In vitro and in vivo modulation of vascular barrier integrity by sphingosine 1-phosphate: mechanistic insights," Cellular Signaling (2005) 17:131-139.
Medscape, "Extracolonic Motility Abnormalities," http://www.medscape.com/viewarticle/442893_4 (Nov. 6, 2007) 2 pages—from Persistence of Abdominal Symptoms after Successful Surgery from South. Med. J. (2002) 95(9):1042-1046.
Medscape, "Irritable bowel syndrome and functional dyspepsia," http://www.medscape.com/viewarticle/506798_5 (Nov. 6, 2007) 3 pages—from Medscape General Medicine (2005) 7(3):17.

Melzig, M.F. et al., "Stimulation of endothelial angiotensin-converting enzyme by morphine via non-opioid receptor mediated processes," Pharmazie. (1998) 53:634-637.
Meyer, M., "Palliative care and AIDS: 2. Gastrointestinal symptoms," Int. J. Std. AIDS (1999) 10:495-505.
Mickley, G.A. et al., Quaternary naltrexone reverses morphine-induced behaviors. Physiol Behav. Aug. 1985;35(2):249-53.
Miedema, B.W. et al., Methods for decreasing postoperative gut dysmotility. Lancet Oncol. Jun. 2003;4(6):365-72.
Min, D.H. et al., "Chemical screening by mass spectrometery to identify inhibitors of anthrax lethal factor," Nat. Biotechnol. (2004) 22:717-723.
Misra, A.L. et al., Intravenous kinetics and metabolism of [15,16-3H]naltrexonium methiodide in the rat. J Pharm Pharmacol. Mar. 1987;39(3):225-7.
Mitchell, D. et al., "Poison induced pica in rats," Physiol. Behav. (1976) 17:691-697.
Mitchell, E. et al., "Structural basis for oligosaccharide-mediated adhesion of Pseudomonas aeruginosa in the lungs of cystic fibrosis patients," Nat. Struct. Biol. (2002) 9:918-921.
Mitchell, R.N. et al., "The link between IFN-γ and allograft arteriopathy: is the answer NO?" J. Clin. Invest. (2004) 114:762-764.
Mitsuya, H. et al., "Strategies for antiviral therapy in AIDS," Nature (1987) 325:773-778.
Moerman, I. et al., Evaluation of methylnaltrexone for the reduction of postoperative vomiting and nausea incidences. Acta Anaesthesiol Belg. 1995;46(3-4):127-32.
Moore, T., "Regulation of pulmonary endothelial cell shape by TRP-mediated calcium entry-transient receptor potential," Thomas L. Petty 40th Annual Aspen Lung Conference: Biology and Pathobiology of the Lung Circulation (1998) Chest 114:36S-38S.
Moser, C. et al., "Improved outcome of chronic Pseudomonas aeruginosa lung infection is associated with induction of a Th1-dominated cytokine response," Clin. Exp. Immunol. (2002) 127:206-213.
Moss, J. and Foss, J., "Pain relief without side effects: peripheral opiate antagonists," 33rd ASA Refresher Courses in Anesthesiology, Philadelphia, Lippincott Williams & Wilkins, Schwartz A.J. editor (2006) 175-186.
Moss, J. et al., "Opioid-induced changes in pulmonary barrier integrity may explain heroid-induced pulmonary edema," American Society of Anesthesiologists presentation, Oct. 17, 2007 in San Francisco, CA (Abstract).
Moss, J. et al., Methylnaltrexone prevents morphine-induced CCR5 receptor expression. Anesthesiology. 2003;99. Abstract A-961.
Moss, J. et al., Selective postoperative inhibition of gastrointestinal opioid receptors. N. Engl. J. Med. 2002;346(6):455.
Motwani, B. et al., "Pharmacoenhancement of protease inhibitors," Am. J. Ther. (2006) 13:57-63.
Mucha, R.F., Is the motivational effect of opiate withdrawal reflected by common somatic indices of precipitated withdrawal? A place conditioning study in the rat. Brain Res. Aug. 25, 1987;418(2):214-20.
Mucha, R.F., Taste aversion involving central opioid antagonism is potentiated in morphine-dependent rats. Life Sci. 1989;45(8):671-8.
Murohara, T. et al., "Nitrix oxide synthase modulates angiogenesis in response to tissue ischemia," J. Clin. Invest. (1998) 101(11):2567-2578.
Murono, K. et al., "Molecular comparison of bacterial isolates from blood with strains colonizing pharynx and intestine in immunocompromised patients with sepsis," J. Med. Microbiol. (2003) 52:527-530.
Murphey, E.D. et al., "Diminished bacterial clearance is associated with decreased IL-12 and interferon-gamma production but a sustained proinflammatory response in a murine model of postseptic immunosuppression," Shock (2004) 21:415-425.
Murphy, D.B. et al., "Pharmacokinetic of epidural administered methylnaltrexone a novel peripheral opioid antagonist," American Society of Anesthesiologists 1999 annual meeting. Dallas, Texas, USA. Oct. 9-13, 1999. ASA Abstracts, Anesthesiology, Sep. 1999;91(3A Suppl):A349.

(56) References Cited

OTHER PUBLICATIONS

Murphy, D.B. et al., Opioid antagonist modulation of ischaemia-induced ventricular arrhythmias: a peripheral mechanism. J Cardiovasc Pharmacol. Jan. 1999;33(1):122-5.
Murphy, D.B. et al., Opioid-induced delay in gastric emptying: a peripheral mechanism in humans. Anesthesiology. Oct. 1997;87(4):765-70.
Murphy, D.B. et al., Pharmacokinetic profile of epidurally administered methylnaltrexone, a novel peripheral opioid antagonist in a rabbit model. Br J Anaesth. Jan. 2001;86(1):120-2.
Naranjo, J.R. et al., Evidence for a central but not adrenal, opioid mediation in hypertension induced by brief isolation in the rat. Life Sci. May 26, 1986;38(21):1923-30.
National Cancer Institute, "Bevacizumab combined with chemotherapy prolongs survival for some patients with advanced lung cancer," http://www.cancer.gov/newscenter/newsfromnci/2005/avastinlung, posted May 13, 2005.
Nazli, A. et al., "Epithelia under metabolic stress perceive commensal bacteria as a threat," Am. J. Pathol. (2004) 164:947-957.
Nelson, C.J., "Morphine modulation of the contact hypersensitivity response: a pharmacological and immunological characterization," Dissertation Abstracts International, (2001) (62/03-B), p. 1635 (Abstract).
Nemeth-Lefkowitz, D. et al., "Hematological and immunological effects of methadone administration in mice," Research Communications in Substance Abuse (1980) 1(2): 177-83.
Neuhauser, M.M. et al., "Antibiotic resistance among gram-negative bacilli in U.S. intensive care units: implications for fluoroquinolone use," JAMA (2003) 289:885-888.
Neumann, P.B. et al., "Plasma morphine concentrations during chronic oral administration in patients with cancer pain," Pain (1982) 13:247-252.
Neves, F.O. et al., "Overexpression of a synthetic gene encoding human alpha interferon in *Escherichia coli*," Protein Expr. Purif. (2004) 35:353-359.
Nsereko et al., "Localized delivery of paclitaxel in solid tumors from biodegradable chitin microparticle formulations," Biomaterials, 2002, vol. 23, Iss. 13, pp. 2723-2731.
Nusrat, A. et al., "Molecular physiology and pathophysiology of tight junctions. IV. Regulation of tight junctions by extracellular stimuli: nutrients, cytokines, and immune cells," Am. J. Physiol. Gastrointest. Liver Physiol. (2000) 279:G851-857.
Odio, M. et al., Central but not peripheral opiate receptor blockade prolonged pituitary-adrenal responses to stress. Pharmacol Biochem Behav. Apr. 1990;35(4):963-9.
Ojielo, C.I. et al., "Defective phagocytosis and clearance of Pseudomonas aeruginosa in the lung following bone marrow transplantation," J. Immunol (2003) 171:4416-4424.
Olanders, K. et al., "The effect of intestinal ischemia and reperfusion injury on ICAM-1 expression, endothelial barrier function, neutrophil tissue influx, and protease inhibitor levels in rats," Shock (2002) 18:86-92.
Osinski, J. et al., Determination of methylnaltrexone in clinical samples by solid-phase extraction and high-performance liquid chromatography for a pharmacokinetics study. J Chromatogr B Analyt Technol Biomed Life Sci. Nov. 25, 2002;780(2):251-9.
Osmon, S. et al., "Hospital mortality for patients with bacteriemia due to *Staphylococcus aureus* or Pseudomonas aeruginosa," Chest (2004) 125:607-616.
O'Toole, G.A. et al., "Initiation of biofilm formation in pseudomonas fluorescens WCS 365 proceeds via multiple, convergent signaling pathways: a genetic analysis," Mol. Microbiol. (1998) 28:449-461.
Padua, C.A. et al., "High incidence of adverse reactions to initial antiretroviral therapy in Brazil," Brazil J. med. Biol. Res. (2006) 39:495-505.
Papapetropoulos, A. et al., Nitric oxide synthase inhibitors attenuate transforming-growth-factor-beta 1-stimulated capillary organization in vitro. Am J Pathol. May 1997;150(5):1835-44.
Pappagallo, M., Incidence, prevalence, and management of opioid bowel dysfunction. Am J Surg. Nov. 2001;182(5A Suppl):11S-18S.
Parkins, M.D. et al., "Pseudomonas aeruginosa GacA, a factor in multihost virulence, is also essential for biofilm formation," Mol. Microbiol. (2001) 40:1215-1226.
Parsek, M.R. et al., "Acyl-homoserine lactone quorum sensing in gram-negative bacteria: a signaling mechanism involved in associations with higher organisms," Proc. Natl. Acad. Sci. USA (2000) 97:8789-8793.
Parsek, M.R. et al., "Quorum sensing signals in development of Pseudomonas aeruginosa biofilms," Methods Enzymol. (1999) 310:43-55.
Pasi, A. et al., "Angiogenesis: modulation with opioids," Gen. Pharmacol. (1991) 22(6):1077-1079.
Pastores, S.M. et al., "Splanchnic ischemia and gut mucosal injury in sepsis and the multiple organ dysfunction syndrome," Am. J. Gastroenterol. (1996) 91:1697-1710.
Patel, H.H. et al., "COX-2 and iNOS in opioid-induced delayed cardioprotection in the intact rat," Life Sci. (2004) 75:129-140.
Paulson, D.M. et al., "Alvimopan: an oral, peripherally acting, mu-opioid receptor antagonist for the treatment of opioid-induced bowel dysfunction—a 21-day treatment—randomized clinical trial," J. Pain (2005) 6(3):184-192.
Pearson, J.P. et al., "Roles of pseudomonas aeruginosa las and rhl quorum-sensing systems in control of elastase and rhamnolipid biosynthesis genes," J. Bacteriol. (1997) 179:5756-5767.
Peart, J.N. et al., "Opioid-induced preconditioning: recent advances and future perspectives," Vasc. Pharmacol. (2005) 42:211-218.
Pennisi, E., "Infectious disease. Cholera strengthened by trip through gut," Science (2002) 296:1783-1784.
Pham, P.T.K. et al., Drugs of Abuse: Chemistry, Pharmacology, Immunology and AIDS; National Institute of Drug Research 96: Monograph Series. U.S. Department of Health and Human Services (1990) 1-243.
Polak, J.M. et al., Enkephalin-like immunoreactivity in the human gastrointestinal tract. Lancet. May 7, 1977;1(8019):972-4.
Polakiewicz, R.D. et al., "μ-opioid receptor activates signaling pathways implicated in cell survival and translational control," J. Biol. Chem. (1998) 273(36):23534-23541.
Polte, T. et al., "Cyclic AMP mediates endothelial protection by nitric oxide," Biochem. Biophys. Res. Commun. (1998) 251:460-465.
Poonawala, T. et al., "Opioids heal ischemic wounds in the rat," Wound Repair Regen. (2005) 13(2):165-174.
Popov, I., "Systemic treatment of colorectal cancer in Serbia: what have we done and what can offer in the new century?" Acta Chir. Iugosl. (2004) 51(2):117-121.
Powell, K.J. et al., Paradoxical effects of the opioid antagonist naltrexone on morphine analgesia, tolerance, and reward in rats. J Pharmacol Exp Ther. Feb. 2002;300(2):588-96.
Proctor, V.E. et al., "Barriers to adherence to highly active antiretroviral therapy as expressed by people living with HIV/AIDS," AIDS Patient Care STDS (1999) 13:535-544.
Progenics Pharmaceuticals, Inc., "Progenies achieves enrollment target in pivotal phase 3 clinical trial of methylnaltrexone for opioid-induced constipation," Press Release, Dec. 3, 2004.
Progenics Pharmaceuticals, Inc., "Progenies announces positive top-line results from pivotal phase 3 clinical trial of MNTX in opioid-induced constipation," Press Release, Mar. 10, 2005.
Progenics Pharmaceuticals, Inc., "Progenies initiates second phase 3 clinical trial of methylnaltrexone in opioid-induced constipation," Press Release, Jan. 13, 2004.
Proquest, "Pain management; cancer-pain remedy wins orphan drug status," Cancer Biotech. Weekly, (1996) p. 16—http://proquest.umi.com/pqdweb?index=32&sid=1&srchmode=3&vinst=PROD&fmt=3&s (Nov. 6, 2007).
Pugsley, M.K. et al., "Cardiovascular actions of the κ-agonist U-50,488H in the absence and presence of opioid receptor blockade," Br. J. Pharmacol. (1992) 105:521-526.
Qiao, J. et al., "PKA inhibits RhoA activation: a protection mechanism against endothelial barrier dysfunction," Am. J. Physiol. Lung Cell Mol. Physiol. (2003) 284:L972-L980.

(56) References Cited

OTHER PUBLICATIONS

Quang-Contagrel, N.D. et al., Long-term methadone treatment: effect on CD4+ lymphocyte counts and HIV-1 plasma RNA level in patients with Hw infection. Eur J Pain. 2001;5(4):415-20.
Quock, R.M. et al, Microwave facilitation of methylnaltrexone antagonism of morphine-induced analgesia in mice. J Bioelect. 1986;5(1):35-46.
Quock, R.M. et al., Narcotic antagonist potentiation of apomorphine drug effect: a stereospecific, centrally mediated drug action. Prog Neuropsychopharmacol Biol Psychiatry. 1985;9(3):239-43.
Quock, R.M. et al., Narcotic antagonist-induced hypotension in the spontaneously hypertensive rat. Life Sci. Sep. 2, 1985;37(9):819-26.
Ramabadran, K., Effects of N-methylnaloxone and N-methylnaltrexone on nociception and precipitated abstinence in mice. Life Sci. Sep. 20-27, 1982;31(12-13):1253-6.
Reimmann et al., "The global activator GacA of pseudomonas aeruginosa PAO positively controls the production of the autoinducer N-butyryl-homoserine lactone and the formation of the virulence factors pyocyanin, cyanide, and lipase," Mol. Microbiol. (1997) 24:309-319.
Remington's Pharmaceutical Sciences, 15th Edition, Mack Publishing Co., (1995) 1614-1615.
Resnick, J. et al., Delayed gastric emptying and postoperative ileus after nongastric abdominal surgery: part I. Am J Gastroenterol. May 1997;92(5):751-62.
Resnick, J. et al., Delayed gastric emptying and postoperative ileus after nongastric abdominal surgery: part II. Am J Gastroenterol. Jun. 1997;92(6):934-40.
Risdahl, J.M. et al., "Opiates and infection," J. Neuroimmunol. (1998) 83:4-18.
Rivière, P.J.M. et al., Fedotozine reverses ileus induced by surgery or peritonitis: action at peripheral kappa-opioid receptors. Gastroenterology. Mar. 1993;104(3):724-31.
Rivkin, A. et al., "Lubiprostone: chloride channel activator for chronic constipation," Clin. Ther. (2006) 28:2008-2021.
Robinson, B.A. et al., Oral naloxone in opioid-associated constipation. Lancet. Aug. 31, 1991;338(8766):581-2.
Rocha, F. et al., "Surgical stress shifts the intestinal *Escherichia coli* population to that of a more adherent phenotype: role in barrier regulation," Surgery (2001) 130:65-73.
Roger, Th. et al., Colonic motor responses in the pony: relevance of colonic stimulation by opiate antagonists. Am J Vet Res. Jan. 1985;46(1):31-5.
Rojas, M. et al., "A dot-blot assay for adhesive components relative to probiotics," Methods Enzymol. (2001) 336:389-402.
Roy, S. et al., "Morphine modulates NF κ B activation in macrophages," Biochem. Biophys. Res. Commun. (1998) 245:392-396.
Russell, J. et al., Antagonism of gut, but not central effects of morphine with quaternary narcotic antagonists. Eur J Pharmacol. Mar. 12, 1982;78(3):255-61.
Sachs, D. et al., "Peripheral analgesic blockade of hypernociception: activation of arginine/NO/cGMP/protein kinase G/ATP-sensitive K + channel pathway," Proc. Natl. Acad. Sci. USA (2004) 101(10):3680-3685.
Sakurada, S. et al., Differential antagonism of endomorphin-1 and endomorphin-2 supraspinal antinociception by naloxonazine and 3-methylnaltrexone. Peptides. May 2002;23(5):895-901.
Sala, R. et al., "Protection by N-acetylcysteine against pulmonary endothelial cell damage induced by oxidant injury," Eur. Respir. J. (1993) 6:440-446.
Sall, W., "Bevacizumab(Avastin) in advanced prostate cancer," Oncolink at the Chemotherpay Foundation Symposium (2003) 2 pages.
Sandner-Keisling, A. et al., Pharmacology of opioid inhibition to noxious uterine cervical distension. Anesthesiology. Oct. 2002;97(4):966-71.
Sansonetti, P., "Host-pathogen interactions: the seduction of molecular cross talk," Gut (2002) 50 Suppl. 3:iii2-8.
Sawa, T. et al., "In vitro cellular toxicity predicts Pseudomonas aeruginosa virulence in lung infections," Infect. Immun. (1998) 66:3242-3249.
Schaefer, G.J. et al., Effects of opioid antagonists and their quaternary derivatives on locomotor activity and fixed ratio responding for brain self-stimulation in rats. Pharmacol Biochem Behav. Nov. 1985;23(5):797-802.
Schang, J.C. et al., Beneficial effects of naloxone in a patient with intestinal pseudoobstruction. Am J Gastroenterol. Jun. 1985;80(6):407-11.
Schang, J.C. et al., How does morphine work on colonic motility? An electromyographic study in the human left and sigmoid colon. Life Sci. Feb. 24, 1986;38(8):671-6.
Schiller, L.R. et al., Studies of the mechanism of the antidiarrheal effect of codeine. J Clin Invest. Nov. 1982;70(5):999-1008.
Schmidhammer, H. et al., Synthesis and biological evaluation of 14-alkoxymorphinans. Part 10[1]. 14-O-methyl derivatives of 5-methylnalthrexone and 5-methylnaloxone. Helv Chim Acta. 1994; 77(6):1585-9.
Schmidhammer, H. et al., Synthesis and biological evaluation of 14-alkoxymorphinans. Part 9[1]. 14-O-ethyl-5-methylnaltrexone, an opioid antagonist with unusual selectivity. Helv Chim Acta. 1993; (1):476-80.
Schmidt, W.K., "Alvimopan (ADL 8-2698) is a novel peripheral opioid antagonist," Am. J. Surg. (2001) 182(5A Suppl):11S-18S.
Schmith, V.D. et al., "Alvimopan pharmacokinetics (PK) and Pharmacodynamics (PD) in patients with chronic constipation (CC)," Clinical Pharmacology & Therapeutics (2005) 77(2) P49.
Scholz, M., Managing constipation that's opioid-induced. 2000; 63(6):103.
Schreier, W.A. et al., Central regulation of intestinal function: morphine withdrawal diarrhea. Proc West Pharmacol Soc. 1982;25:151-4.
Schubert-Zsilavecz, V.M. et al., Das reizdarmsyndrom irritable bowel syndrome. Deutsche apotheker zeitung. Aug. 22, 2002; 142(34): 40-9.
Schultz, M.J. et al., "Endogenous interferon-gamma impairs bacterial clearance from lungs during Pseudomonas aeruginosa pneumonia," Eur. Cytokine Netw. (2001) 12:39-44.
Schuster, M. et al., "Identification, timing, and signal specificity of Pseudomonas aeruginosa quorum-controlled genes: a transcriptome analysis," J. Bacteriol. (2003) 185:2066-2079.
Schuster, M. et al., "Promoter specificity in pseudomonas aeruginosa quorum sensing revealed by DNA binding of purified LasR," Proc. Natl. Acad. Sci. USA (2004) 101(45):15833-15839.
Schuster, M. et al., "The Pseudomonas aeruginosa RpoS regulon and its relationship to quorum sensing," Mol. Microbiol. (2004) 51:973-985.
Schwartzentruber, D.J. et al., "Specific release of granulocyte-macrophage colony-stimulating factor, tumor-necrosis factor-α, and IFN-γ by human tumor-infiltrating lymphocytes after autologous tumor stimulation," J. Immunol (1991) 146:3674-3681.
Selgelid, M.J., "Ethids and infectious disease," Bioethics (2005) 19:272-289.
Sezen, S.F. et al., "Renal excretory responses produced by the delta opioid agonist, BW373U86, in conscious rats," J. Pharmacol. Exp. Ther. (1998) 287:238-245.
Shahbazian, A. et al., "Involvement of μ- and κ-, but not δ-, opiod receptors in the peristaltic motor depression caused by endogenous and exogenous opiods in the guinea pig intestine," Br. J. Pharmacol. (2002) 135:741-750.
Shavit, Y. et al., Effects of a single administration of morphine or footshock stress on natural killer cell cytotoxicity. Brain Behav Immun. Dec. 1987;1(4):318-28.
Shi, E. et al., "Cardioprotective effects of morphine on rat heart suffering from ischemia and reperfusion," Chin. Med. J. (Engl) (2003) 116:1059-1062.
Shibata, N. et al., "Drug interactions between HIV protease inhibitors based on a physiologically based pharmacokinetic model," J. Pharm. Sci. (2002) 91:680-689.
Singleton, P.A. et al., "CD44 interaction with ankyrin and IP3 receptor in lipid rafts promotes hyaluronan-mediated Ca2+ signal-

(56) References Cited

OTHER PUBLICATIONS ing leading to nitric oxide production and endothelial cell adhesion and proliferation," Exp. Cell Res. (2004) 295:102-118.
Singleton, P.A. et al., "CD44v10 interaction with Rho-kinase (ROK) activates inositol 1,4,5-triphosphate (IP3) receptor-mediated Ca2+ signaling during hyaluronan (HA)-induced endothelial cell migration," Cell Motility and the Cytoskeleton (2002) 53:293-316.
Singleton, P.A. et al., "Regulation of sphingosine 1-phosphate-induced endothelial cytoskeletal rearrangement and barrier enhancement by S1P1 receptor, PI3 kinase, Tiam1/Rac1, and a-actinin," FASEB Journal (2005) 19:1646-1656.
Smith, M.G. et al., "Microbial synergy via an ethanol-triggered pathway," Mol. Cell Biol. (2004) 24:3874-3884.
Smith, R.S. et al., "An adenylate cyclase-controlled signaling network regulates Pseudomonas aeruginosa virulence in a mouse model of acute pneumonia," Infect. Immun (2004) 72:1677-1684.
Smith, R.S. et al., "P. aeruginosa quorum-sensing systems and virulence," Curr. Opin. Microbiol. (2003) 6:56-60.
Soldani, G. et al., Central and peripheral involvement of mu receptors in gastric secretory effects of opioids in the dog. Eur J Pharmacol. Nov. 19, 1985;117(3):295-301.
Solvason, H.B. et al., Naltrexone blocks the expression of the conditioned elevation of natural killer cell activity in BALB/c mice. Brain Behav Immun. Sep. 1989;3(3):247-62.
Sperandio, V. et al., "Bacteria-host communication: the language of hormones," Proc. Natl. Acad. Sci USA (2003) 100:8951-8956.
Srinivasan, A. et al., "An outbreak of Pseudomonas aeruginosa infections associated with flexible bronchoscopes," N. Eng. J. Med. (2003) 348:221-227.
Stanski, D.R. et al., "Kinetics of intravenous and intramuscular morphine," Clin. Pharmacol. Ther. (1978) 24(1):52-59.
Stefano, G.B. et al., "Long-term exposure of human blood vessels to HIV gp120, morphine, and anandamide increases endothelial adhesion of monocytes: uncouple of nitric oxide release," J. Cardiovasc. Pharmacol. (1998) 31:862-868.
Stefano, G.B. et al., "Morphine enhances nitric oxide release in the mammalian gastrointestinal tract via the micro(3) opiate receptor subtype: a hormonal role for endogenous morphine," J. Physiol. Pharmacol. (2004) 55:279-288.
Stefano, G.B. et al., "Presence of the µ3 opiate receptor in endothelial cells. Coupling to nitric oxide production and vasodilation," J. Biol. Chem. (1995) 270:30290-30293.
Stefano, G.B. et al., "δ-2 opioid receptor subtype on human vascular endothelium uncouples morphine stimulated nitric oxide release," Int. J. Cardiol. (1998) 64(Suppl. 1):S43-S51.
Steidler, L. et al., "Treatment of murine colitis by Lactococcus lactis secreting interleukin-10," Science (2000) 289:1352-1355.
Steinbrook, R.A. et al., An opioid antagonist for postoperative ileus. N Engl J Med. Sep. 27, 2001;345(13):988-9.
Stephenson, E.J. et al., "µ opioid receptor stimulates a growth promoting and pro-angiogenic tumor microenvironment by transactivating VEGF receptor-2/Flk-1," Blood (ASH Annual Meeting Abstracts (2005) 106:Abstract 3687.
Stephenson, J. et al., Methylnaltrexone reverses opioid-induced constipation. Lancet Oncol. Apr. 2002;3(4):202.
Sternini, C. et al., "The opioid system in the gastrointestinal tract," Neurogastroenterol Motil. (2004) 16 Suppl 2, 3-16.
Stevens, T. et al., "Mechanisms regulating endothelial cell barrier function," Am. J. Physiol. Lung Cell Mol. Physiol. (2002) 279:L419-L422.
Stiene-Martin, A. et al., "Regional, developmental, and cell cycle-dependent differences in µ, δ, and κ-opioid receptor expression among cultured mouse astrocytes," Glia (1998) 22:249-259.
Stover, C.K. et al., "Complete geome sequence of pseudomonas aeruginosa PAO1, an opportunistic pathogen," Nature (2000) 406:959-964.
Strohmeier, G.R. et al., "Surface expression, polarization, and functional significance of CD73 in human intestinal epithelia," J. Clin. Invest. (1997) 99:2588-2601.

Sun, J. et al., "Bacterial activation of beta-catenin signaling in human epithelia," Am. J. Physiol. Gastrointest. Liver Physiol. (2004) 287:G220-G227.
Sun, Z. et al., "Gut barrier permeability, reticuloendothelial system function and protease inhibitor levels following intestinal ischaemia and reperfusion—effects of pretreatment with N-acetyl-L-cysteine and indomethacin," Dig. Liver Dis. (2002) 34:560-569.
Suzuki, S. et al., "Morphine suppresses lymphocyte spoptosis by blocking p53-mediated death signaling," Biochem. Biophys. Res. Commun. (2003) 308:802-808.
Swan, N.et al., NIDA plays key role in studying links between AIDS and drug abuse. AIDS Research, NIDA Notes. 1995; 10(3):1-6.
Sykes, N.P., "Using oral naloxone in management of opioid bowel dysfunction," Handbook of Opioid Bowel Syndrome, New York, Haworth Medical Press, Yuan, C-S. editor (2005) Chapter 9, 175-195.
Sykes, N.P., Oral naloxone in opioid-associated constipation. Lancet. Jun. 15, 1991;337(8755):1475.
Taguchi, A. et al., "Selective postoperative inhibition of gastrointestinal opioid receptors," N. Engl. J. Med. (2001) 345:935-940.
Takeda, N. et al., "Neuropharmacological mechanisms of emesis. I. Effects of antiemetic drugs on motion- and apomorphine-induced pica in rats," methods Find. Exp. Clin. Pharmacol. (1995) 17:589-590.
Takeda, N. et al., "Pica in rats is analogous to emesis: an animal model in emesis research," Pharmacol. Biochem. Behav. (1993) 45:817-821.
Talley, N.J. et al., Pharmacologic therapy for the irritable bowel syndrome. Am J Gastroenterol. Apr. 2003;98(4):750-8.
Tan, M.W. et al., "Killing of caenorhabditis elegans by Pseudomonas aeruginosa used to model mammalian bacterial pathogenesis," Proc. Natl. Acad. Sci. USA (1999) 96:715-720.
Tegeder, I. et al., "Opioids as modulators of cell death and survival—unraveling mechanisms and revealing new indications," Pharm. Rev. (2004) 56(3):351-369.
Thomas, J. et al., "A phase III double-blind placebo-controlled trial of methylnaltrexone (MNTX) for opioid-induced constipation (OIC) in advanced medical illness (AMI)," Abstract No. LBA8003 from the 2005 ASCO Annual Meeting (3 pages).
Thomas, J. et al., Amelioration of peripheral side effects of opioids: clinical experience with methylnaltrexone (MNTX). Proc World Congr Anesth. 2004:107.
Thompson, A.C. et al., Opioid stimulation in the ventral tegmental area facilitates the onset of maternal behavior in rats. Brain Res. Dec. 16, 1996;743(1-2):184-201.
Thompson, W.G. et al., Laxatives: clinical pharmacology and rational use. Drugs. Jan. 1980;19(1):49-58.
Tiruppathi, C. et al., "Endothelial permeability/pulmonary edema," Circ. Res. (2002) 91(1):70-76.
Tomiyasu, S. et al., Analysis of intercostal nerve damage associated with chronic post-thoracotomy pain. Anesthesiology. 2001;95. Abstract A-964.
Trebichavsky, I. et al., "Systemic and local cytokine response of young piglets to oral infection with *Salmonella enterica* serotype Typhimurium," Folia Microbiol. (2003) 48:403-407.
Tryoen-Toth, P. et al., "Regulation of K-opioid receptor mRNA level by cyclic AMP and growth factors in cultured rat glial cells," Mol. Brain Res. (1998) 55:141-150.
Tsikitis, V.L. et al., "The lectin-like domain of compliment receptor 3 protects endothelial barrier function from activated neutrophils," J. Immuno. (2004) 173:1284-1291.
Turner, J.R. et al., "Physiological regulation of epithelial tight junctions is associated with myosin light-chain phosphorylation," Am. J. Physiol. Cell Physiol. (1997) 273:C1378-C1385.
Uccelletti, D. et al., "Ire-1-dependent transcriptional up-regulation of a lumenal uridine diphosphatase from Caenorhabditis elegans," J. Biol. Chem. (2004) 279:27390-27398.
Ukai, M. et al., Suppression of deprivation-induced water intake in the rat by opioid antagonists: central sites of action. Psychopharmacology (Berl). 1987;91(3):279-84.

(56) References Cited

OTHER PUBLICATIONS

Valentino, R.J. et al., Quaternary naltrexone: evidence for the central mediation of discriminative stimulus effects of narcotic agonists and antagonists. J Pharmacol Exp Ther. Jun. 1981;217(3):652-9.
Valentino, R.J. et al., Receptor binding, antagonist, and withdrawal precipitating properties of opiate antagonists. Life Sci. Jun. 20, 1983;32(25):2887-96.
Vallejo, R. et al., "Opioid therapy and immunosuppression: a review," Am. J. Ther. (2004) 11:354-365.
Venturi, V., "Control of rpoS transcription in *Escherichia coli* and Pseudomonas: why so different?" Mol. Microbiol. (2003) 49:1-9.
Viswanathan, V.K. et al., "Microbes and their products—physiological effects upon mammalian mucosa," Adv. Drug Delivery Res. (2004) 56:727-762.
Wagner, V.E. et al., "Microarray analysis of Pseudomonas aeruginosa quorum-sensing regulons: effects of growth phase and environment," J. Bacteriol. (2003) 185:2080-2095.
Waldhoer, M. et al., "Opioid receptors," Annu. Rev. Biochem. (2004) 73:953-990.
Walker, M.J.K. et al., Role of central versus peripheral opioid receptors in analgesia induced by repeated administration of opioid antagonists. Psychopharmacology. 1991;104(2):164-6.
Walsh, D. et al., "The symptoms of advanced cancer: relationship to age, gender, and performance status in 1,000 patients," Support Care Cancer (2000) 8:175-179.
Wang, J. et al., "Morphine negatively regulates interferon-γ promoter activity in activated murine T cells through two distinct cyclic AMP-dependent pathways," J. Biol. Chem. (2003) 278(39):37622-37631.
Wang, J. et al., "The immunosuppressive effects of chronic morphine treatment are partially dependent on corticosterone and mediated by the ν-opioid receptor," J. Leukoc. Biol. (2002) 71:782-790.
Wang, X. et al., "A non-peptide substance P antagonist (CP-96,345) inhibits morphine induced NF-κB promoter activation in human NT2-N neurons," J. Neurosci. Res. (2004) 75:544-553.
Warren, P.H. et al., Effects of quaternary naltrexone and chlordiazepoxide in squirrel monkeys with enhanced sensitivity to the behavioral effects of naltrexone. J Pharmacol Exp Ther. Nov. 1985;235(2):412-7.
Wei, G. et al., "Effects of subcutaneous methylnaltrexone on morphine-induced gut motility changes: a clinical trial," Abstracts of the 2002 Annual Meeting of the American Society for Clinical Pharmacology and Therapeutics. Atlanta, Georgia, USA. Mar. 24-27, 2002. Clin Pharmacol Ther. Feb. 2002;71(2):MPI-26.
Wei, G. et al., Opioid-induced immunosuppression: is it centrally mediated or peripherally mediated? Biochem Pharmacol. Jun. 1, 2003;65(11):1761-6.
Wei, G. et al., Pharmacokinetics of subcutaneous methylnaltrexone: different route administration comparison. 2001. ASA Annual Meeting Abstracts. Oct. 14-18, 2001. Chicago, IL. Abstract A-962.
Wellink, J. et al., "Proteases involved in the processing of viral polyproteins," Brief Review. Arch. Virol. (1988) 98:1-26.
West, S.E. et al., "Construction of improved *Escherichia*-Pseudomonas shuttle vectors dervied from pUC18/19 and sequence of the region required for their replication in Pseudomonas aeruginosa," Gene (1994) 148(1):81-86.
Westerman, B.A. et al., "C2360, a nuclear protein expressed in human proliferative cytotrophoblasts, is a representative member of a novel protein family with a conserved coiled coil-helix-coiled coil-helix domain," Genomics (2004) 83:1094-1104.
Wetzker, R. et al., "Transactivation joins multiple tracks to the ERK/MAPK cascade," Nat. Rev. (2003) 4:651-657.
Whistler, C.A. et al., "The two-component regulators GacS and GacA influence accumulation of the stationary-phase sigma factor sigmaS and the stress response in Pseudomonas fluorescens Pf-5," J. Bacteriol. (1998) 180:6635-6641.
Whistler, J.L. et al., "Functional dissociation of μ opioid receptor signaling and endocytosis: implications for the biology of opiate tolerance and addiction," Neuron (1999) 23:737-746.

Whistler, J.L. et al., "Modulation of postendocytic sorting of G protein-coupled receptors," Science (2002) 297:615-620.
White, F.A. et al., "Chemokines: integrators of pain and inflammation," Nature Rev. Drug Discovery (2005) 4:834-844.
Whiteley, M. et al., "Idenfitication of genes controlled by quorum sensing in Pseudomonas aeruginosa," Proc. Natl. Acad. Sci USA (1999) 96:13904-13909.
Whiteley, M. et al., "Promoter specificity elements in Pseudomonas aeruginosa quorum-sensing-controlled genes," J. Bacteriol. (2001) 183:5529-5534.
Whiteley, M. et al., "Regulation of quorum sensing by RpoS in Pseudomonas aeruginosa," J. Bacteriol. (2000) 182:4356-4360.
Willett, C.G. et al., "Direct evidence that the VEGF-specific antibody bevacizumab has antivascular effects in human rectal cancer," Nature Med. (2004) 10(2):145-147.
Willette, R.N. et al., "Evidence for anticholinergic effects of naltrexone methylbromide," Res Comm Subst Abuse (1983) 4(4):325-37.
Wilmore, D.W. et al., Can we minimize the effects of opioids on the bowel and still achieve adequate pain control? Am J Surg. Nov. 200;182(5A Suppl):1S-2S.
Winzer, K. et al., "LuxS: its role in central metabolism and the in vitro synthesis of 4-hydroxy-5-methyl-3(2H)-furanone," Microbiology (2002) 148:909-922.
Winzer, K. et al., "Quorum sensing and the regulation of virulence gene expression in pathogenic bacteria," Int. J. Med. Microbiol. (2001) 291:131-143.
Winzer, K. et al., "The Pseudomonas aeruginosa lectins PA-IL and PA-IIL are controlled by quorum sensing and by RpoS," J. Bacteriol. (2000) 182:6401-6411.
Wittert, G. et al., "Tissue distribution of opioid receptor gene expression in the rat," Biochem. Biophys. Res. Commun. (1996) 218:887-881.
Wolfgang, M.C. et al., "Coordinate regulation of bacterial virulence genes by a novel adenylate cyclase-dependent signaling pathway," Dev. Cell (2003) 4:253-263.
Wu, L. et al., "Highmolecular-weight polyethylene glycol prevents lethal sepsis due to intestinal Pseudomonas aeruginosa," Gastroenterology (2004) 126:488-498.
Wu, L. et al., "Pseudomonas aeruginosa expresses a lethal virulence determinant, the PA-I lectin/adhesin, in the intestinal tract of a stressed host: the role of epithelia cell contact and molecules of the quorum sensing signaling system," Ann. Surg. (2003) 238:754-764.
Wu, L.R. et al., "Surgical injury and metabolic stress enhance the virulence of the human opportunistic pathogen Pseudomonas aeruginosa," Surgical Infections (2005) 6(2):185-195.
Wybran, J. et al., Suggestive evidence for receptors for morphine and methionine-enkephalin on normal human blood T lymphocytes. J Immunol Sep. 1979;123(3):1068-70.
Xie, P. et al., "Activation of NF-κB by bradykinin through a $G\alpha_q$- and $G\beta\gamma$-dependent pathway that involves phosphoinositide 3-kinase and Akt," J. Biol. Chem. (2000) 275(32):24907-24914.
Xu, D.Z. et al., "The effect of hypoxia/reoxygenation on the cellular function of intestinal epithelial cells," J. Trauma (1999) 46:280-285.
Xu, J. et al., "Message from a human gut symbiont: sensitivity is a prerequisite for sharing," Trends Microbiol. (2004) 21-28.
Yamaji, H. et al., "Pharmacokinetic interactions between HIV-protease inhibitors in rats," Biopharm. Drug Dispos. (1999) 20:241-247.
Yarwood, J.M. et al., "Quorum sensing in *Staphylococcus aureus* biofilms," J. Bacteriol. (2004) 186:1838-1850.
Yoshida, S. et al., "Effect of surgical stress on endogenous morphine and cytokine levels in the plasma aafter laparoscopic or open cholecystectomy," Surg. Endosc. (2000) 14:137-140.
Yu, H. et al., "Innate lung defenses and compromised Pseudomonas aeruginosa clearance in the malnourished mouse model of respiratory infections in cystic fibrosis," Infect. Immun. (2000) 68:2142-2147.
Yuan, C.S., "Methylnaltrexone mechanisms of action and effects on opioid bowel dysfunction and other opioid adverse effects," Ann. Pharmacother. (2007) 41:984-993.
Yuan, C.S. et al., "Methylnaltrexone for reversal of constipation due to chronic methadone use," JAMA (2000) 283(3):367-372.

(56) References Cited

OTHER PUBLICATIONS

Yuan, C.S. et al., "Tolerability, gut effects, and pharmacokinetics of methylnaltrexone following repeated intravenous administration in humans," J. Clin. Pharmacol (2005) 45:538-546.
Yuan, C.S. et al., Antagonism of chronic opioid-induce gut effects. Anesth Analg. 2000;90:S1-523. Abstract S479.
Yuan, C.S. et al., Antagonism of gastrointestinal opioid effects. Reg Anesth Pain Med. Nov.-Dec. 2000;25(6):639- 42.
Yuan, C.S. et al., Dose-related effects of oral acetaminophen on cold-induced pain: a double-blind, randomized, placebo-controlled trial. Clin Pharmacol Ther. Mar. 1998;63(3):379-83.
Yuan, C.S. et al., Effects of enteric-coated methylnaltrexone in preventing opioid-induced delay in oral-cecal transit time. Clin Pharmacol Ther. Apr. 2000;67(4):398-404.
Yuan, C.S. et al., Effects of intravenous methylnaltrexone on opioid-induced gut motility and transit time changes in subjects receiving chronic methadone therapy: a pilot study. Pain. Dec. 1999;83(3):631-5.
Yuan, C.S. et al., Effects of low-dose morphine on gastric emptying in healthy volunteers. J Clin Pharmacol. Nov. 1998;38(11):1017-20.
Yuan, C.S. et al., Effects of methylnaltrexone on chronic opioid induced gut motility and transit time changes. Br J Anaesth. 1998;81(1):94.
Yuan, C.S. et al., Effects of methylnaltrexone on chronic opioid-induced gut motility and transit time changes. University of Leicester—Abstracts from the Eighth International Symposium on Pain, Anaesthesia and Endocrinology. Sep. 18-19, 1997.
Yuan, C.S. et al., Effects of methylnaltrexone on morphine-induced inhibition of contraction in isolated guinea-pig ileum and human intestine. Eur J Pharmacol. Mar. 24, 1995;276(1-2):107-11.
Yuan, C.S. et al., Effects of methylnaltrexone on morphine-induced inhibition of contractions in isolated guinea-pig and human intestine. Anesthesiology. Sep. 1995; 83(3A). Abstract A358.
Yuan, C.S. et al., Effects of subcutaneous methylnaltrexone on morphine-induced peripherally mediated side effects: a double-blind randomized placebo-controlled trial. J Pharmacol Exp Ther. Jan. 2002;300(1):118-23.
Yuan, C.S. et al., Efficacy of orally administered methylnaltrexone in decreasing subjective effects after intravenous morphine. Drug Alcohol Depend. Oct. 1, 1998;52(2):161-5.
Yuan, C.S. et al., Gastric effects of methylnaltrexone on mu, kappa, and delta opioid agonists induced brainstem unitary responses. Neuropharmacology. Mar. 1999;38(3):425-32.
Yuan, C.S. et al., Gastric effects of mu-, delta- and kappa-opioid receptor agonists on brainstem unitary responses in the neonatal rat. Eur J Pharmacol. Oct. 24, 1996;314(1-2):27-32.
Yuan, C.S. et al., Gut and brain effects of American ginseng root on brainstem neuronal activities in rats. Amer J Chin Med. 1998; 26: 47-55.
Yuan, C.S. et al., Gut motility and transit changes in patients receiving long-term methadone maintenance. J Clin Pharmacol. Oct. 1998;38(10):931-5.
Yuan, C.S. et al., Methylnaltrexone (MNTX) for chronic opioid-induced constipation. 2002 ASCO Annual Meeting. Proc Am Soc Clin Oncol. 2002;21:376a. Abstract 1501.
Yuan, C.S. et al., Methylnaltrexone (MNTX) reverses chronic opioid constipation: a double-blind, randomized, placebo-controlled trial. Anesthesiology. Sep. 1999; 91 (3A). Abstract A973.
Yuan, C.S. et al., Methylnaltrexone changes gut motility and transit time in chronic methadone-maintained subjects. Anesth Analg. 1999;88: S1-424. Abstract S404.
Yuan, C.S. et al., Methylnaltrexone effects on morphine-induced inhibition in isolated guinea-pig and human intestine. Clin Pharm & Therapeut. Feb. 1995;57:138. Abstract PI-11.
Yuan, C.S. et al., Methylnaltrexone prevents morphine-induced delay in oral-cecal transit time without affecting analgesia: a double-blind placebo-controlled trial. Clin Pharmacol Ther. Apr. 1996;59(4):469-75.
Yuan, C.S. et al., Methylnaltrexone prevents morphine-induced kaolin intake in the rat. Anesthesiology. 2003;99. Abstract A-922.

Yuan, C.S. et al., Methylnaltrexone reduces oral-cecal transit time in humans. Dig Dis Week Abstr. 2003:A-578. Abstract T1840.
Yuan, C.S. et al., Methylnaltrexone reverses morphine-induced changes in gastrointestinal motility: a clinical study. Anesthesiology Sep. 1995; 83(3A): Abstract A360.
Yuan, C.S. et al., Methylnaltrexone: investigation of clinical applications. Drug Develop Res. 2000;50(2):133-41.
Yuan, C.S. et al., Opioid analgesia without gut side effects: effects of methylnaltrexone as a novel peripheral opioid antagonist. Assoc Univ Anesth Abst. 2003: PD2.
Yuan, C.S. et al., Oral methylnaltrexone for opioid-induced constipation. JAMA. Sep. 20, 2000;284(11):1383-4.
Yuan, C.S. et al., Oral methylnaltrexone reverses chronic opioid-induced constipation. Anesthesiology. Sep. 2000;93(3A). Abstract A-872.
Yuan, C.S. et al., Oral methylnaltrexone reverses morphine-induced changes in gastrointestinal motility. Anesthesiology. Sep. 1995;85(3A). Abstract A335.
Yuan, C.S. et al., Pain control without side effects: clinical studies on methylnaltrexone as a novel peripheral opioid antagonist. $7^{th}$ America-Japan Anesth Congr. Yamanashi, Japan. 2002:41.
Yuan, C.S. et al., Pharmacokinetics of intravenous vs. oral methylnaltrexone: evidence for direct gut effects. Anesth Analg. 2001;92: S1-363. Abstract S274.
Yuan, C.S. et al., Safety and tolerance of oral methylnaltrexone in healthy volunteers. Anesth Analg. 1997;84:S1-599. Abstract S574.
Yuan, C.S. et al., Subcutaneous methylnaltrexone prevents morphine-induced delay in gut transit time: a clinical trial. Anesthesiology. 2001;95. Abstract A-963.
Yuan, C.S. et al., The safety and efficacy of oral methylnaltrexone in preventing morphine-induced delay in oralcecal transit time. Clin Pharmacol Ther. Apr. 1997;61(4):467-75.
Yuan, C.S., "Clinical status of methylnaltrexone: a new agent to prevent and manage opioid-induced side effects," J. Support Oncol. (2004) 2:111-122.
Yuan, C-S. et al., "Methylnaltrexone, a novel peripheral opiod receptor antagonist for the treatment of opiod side effects," Exp. Opin. Investig. Drugs (2006) 15(5):541-552.
Zagon, I.S. et al., "Opioid antagonists inhibit the growth of metastatic murine neuro blastoma," Cancer Letts. (1983) 21(1):89-94.
Zagon, I.S. et al., "Opioid growth factor regulates the cell cycle of human neoplasias," Int. J. Oncol. (2000) 17(5):1053-1061.
Zagon, I.S. et al., "Opioids and differentiation in human cancer cells," Neuropeptides (2005) 39:495-505.
Zagon, I.S. et al., "Opioids and the apoptotic pathway in human cancer cells," Neuropeptides (2003) 37:79-88.
Zaugg, M. et al., "Anaesthetics and cardiac preconditioning Part I. Signalling and cytoprotective mechanisms," Br. J. Anaesth. (2003) 91(4):551-565.
Zeng, H. et al., "Heterotrimeric $G\alpha_q/G\alpha_{11}$ proteins function upstream of vascular endothelial growth factor (VEGF) receptor-2 (KDR) phosphorylation in vascular permeability factor/VEGF signaling," J. Biol. Chem. (2003) 278:20738-20745.
Zeng et al., "Expression of Vascular Endothelial Groth factor Receptor-3 by Lymphatic Endothelial Cells is Associated with Lymph Node Metastasis in Prostate Cancer," Clinical Cancer Research, Aug. 2004, vol. 10, pp. 5137-5144.
Zhang, H. et al., "LPS induces permeability injury in lung microvascular endothelium via AT1 receptor," Biochem. Biophys. (2005) 441:75-83.
Zhang, Y. et al., "Effect of the endogenous ? opioid agonist dynorphin A(1-17) on cocaine-evoked increases in striatal dopamine levels and cocaine-induced place preference in C57BL/6J mice," Psychopharmacology (2004) 172:422-429.
Zimmerman, D.M. et al., Discovery of a potent, peripherally selective trans-3,4-dimethyl-4-(3-hydroxyphenyl) piperidine opioid antagonist for the treatment of gastrointestinal motility disorders. J Med Chem. Jul. 22, 1994, 37(15):2262-5.
McKeage, K. et al., "Lubiprostone," Drugs 2006; 66 (6): 873-879.
Crowell, M. et al., "Activation of type-2 chloride channels: a novel therapeutic target for the treatment of chronic constipation," Current opinion in investigational drugs, 2007;8(1):66-70.

(56) References Cited

OTHER PUBLICATIONS

Sorbera, L. A. et al., "Lubiprostone", Drugs of the Future, 2004, vol. 29 No. 4, 336-341.
International Search Report and Written Opinion of International Searching Authority for International Application No. PCT/US2006/007892 dated Oct. 9, 2006.
International Search Report and Written Opinion of International Searching Authority for International Application No. PCT/US2006/021604 dated Jun. 5, 2007.
Partial International Search of International Searching Authority for International Application No. PCT/US2007/066806 dated Dec. 11, 2007.
International Search Report and Written Opinion of International Searching Authority for International Application No. PCT/US2007/066806 dated Apr. 28, 2008.
International Search Report and Written Opinion of the International Searching Authority for Application No. PCT/US2008/085662 dated Apr. 8, 2009 (12 pages).
International Search Report and Written Opinion for Application No. PCT/US08/78229 dated Dec. 24, 2008 (6 pages).
Australian Patent Office Action for Application No. 2007237943 dated Dec. 9, 2011 (2 pages).
Australian Patent Office Action for Application No. 2007237943 dated Oct. 23, 2012 (3 pages).
Canadian Patent Office Action from Application No. 2,649,710 dated May 21, 2013 (3 pages).
Canadian Patent Office Action for Application No. 2,649,710 dated Aug. 12, 2014 (2 pages).
European Patent Office Action for Application No. 07760785.1 dated Jun. 14, 2011 (6 pages).
Japanese Patent Office Action for Application No. 2009-506726 dated May 22, 2012 (4 pages)—English Translation and Original.
Japanese Patent Office Action for Application No. 2009-506726 dated Jan. 22, 2013 (4 pages)—English Translation and Original.
Japanese Patent Office Action for Application No. 2010-537105 dated Jun. 25, 2013 (Original and English Translation, 7 pages).
United States Patent Office Action for U.S. Appl. No. 11/908,058 dated Sep. 28, 2009 (2 pages).
United States Patent Office Action for U.S. Appl. No. 11/908,058 dated May 14, 2010 (12 pages).
United States Patent Office Action for U.S. Appl. No. 11/908,058 dated Nov. 23, 2010 (11 pages).
United States Patent Office Action for U.S. Appl. No. 11/908,058 dated May 12, 2011 (18 pages).
United States Patent Office Action for U.S. Appl. No. 11/908,058 dated Jan. 6, 2012 (19 pages).
United States Patent Office Action for U.S. Appl. No. 11/908,058 dated May 22, 2012 (5 pages).
United States Patent Office Action for U.S. Appl. No. 11/908,058 dated Dec. 7, 2012 (3 pages).
United States Patent Office Action for U.S. Appl. No. 11/908,058 dated Sep. 19, 2013 (11 pages).
United States Patent Office Final Rejection for U.S. Appl. No. 11/908,058 dated Feb. 28, 2014 (15 pages).
United States Patent Office Action for U.S. Appl. No. 11/379,010 dated Dec. 14, 2009 (16 pages).
United States Patent Office Action for U.S. Appl. No. 11/379,010 dated Jun. 23, 2010 (18 pages).
United States Patent Office Advisory Action for U.S. Appl. No. 11/379,010 dated Sep. 29, 2010 (4 pages).
United States Patent Office Action for U.S. Appl. No. 11/379,010 dated Mar. 28, 2011 (17 pages).
United States Patent Office Action for U.S. Appl. No. 11/379,010 dated Nov. 17, 2011 (15 pages).
United States Patent Office Action for U.S. Appl. No. 11/379,010 dated Nov. 26, 2012 (18 pages).
United States Patent Office Action for U.S. Appl. No. 11/379,010 dated Dec. 7, 2012 (3 pages).
United States Patent Office Notice of Allowance for U.S. Appl. No. 11/379,010 dated May 15, 2013 (11 pages).
United States Patent Office Action for U.S. Appl. No. 11/914,984 dated Jan. 5, 2012 (22 pages).
United States Patent Office Action for U.S. Appl. No. 13/483,932 dated Dec. 6, 2012 (18 pages).
United States Patent Office Final Rejection for U.S. Appl. No. 13/483,932 dated Apr. 24, 2013 (12 pages).
United States Patent Office Action for U.S. Appl. No. 12/723,339 dated Sep. 14, 2012 (21 pages).
United States Patent Office Action for U.S. Appl. No. 12/723,339 dated Dec. 7, 2012 (3 pages).
United States Patent Office Notice of Allowance for U.S. Appl. No. 12/723,339 dated Apr. 23, 2013 (11 pages).
United States Patent Office Action for U.S. Appl. No. 11/908,058 dated Dec. 18, 2014 (20 pages).
United States Patent Office Action for U.S. Appl. No. 11/908,058 dated Sep. 16, 2015 (19 pages).
United States Patent Office Action for U.S. Appl. No. 13/972,122 dated Oct. 16, 2015 (29 pages).
United States Patent Office Action for U.S. Appl. No. 13/972,129 dated Nov. 30, 2015 (25 pages).
Krajnik, M., "Opioids and the immune system: implications for clinical practice," Polska Medycyna Paliatywna (2004) 3(2):139-164.
United States Patent Office Action for U.S. Appl. No. 11/908,058 dated Jul. 1, 2016 (36 pages).
United States Patent Office Action for U.S. Appl. No. 14/061,331 dated Jun. 2, 2016 (12 pages).
United States Patent Office Action for U.S. Appl. No. 13/972,129 dated Apr. 19, 2016 (9 pages).
United States Patent Office Notice of Allowance for U.S. Appl. No. 13/972,122 dated Feb. 9, 2017 (10 pages).
United States Patent Office Notice of Allowance for U.S. Appl. No. 11/908,058 dated Jan. 23, 2017 (11 pages).
United States Patent Office Notice of Allowance for U.S. Appl. No. 13/972,129 dated Apr. 18, 2017 (6 pages).

\* cited by examiner

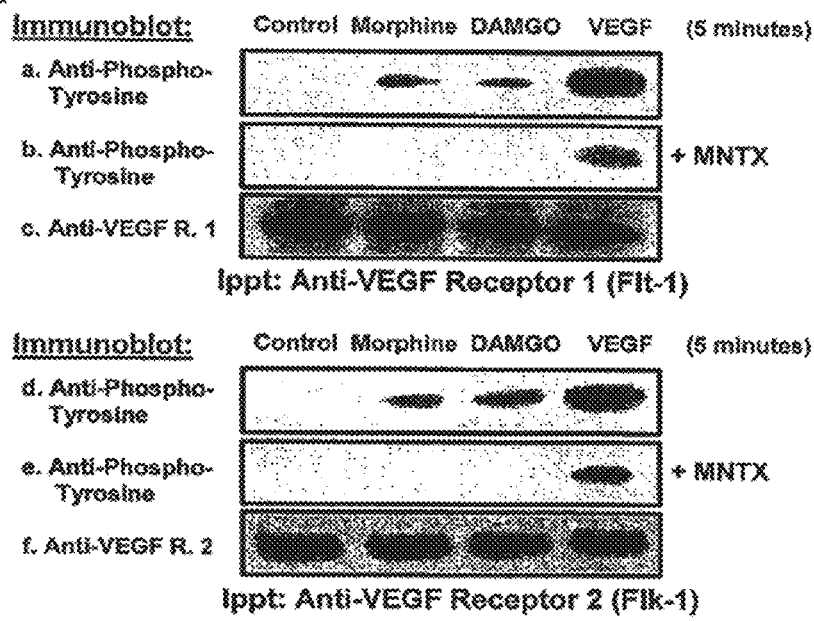
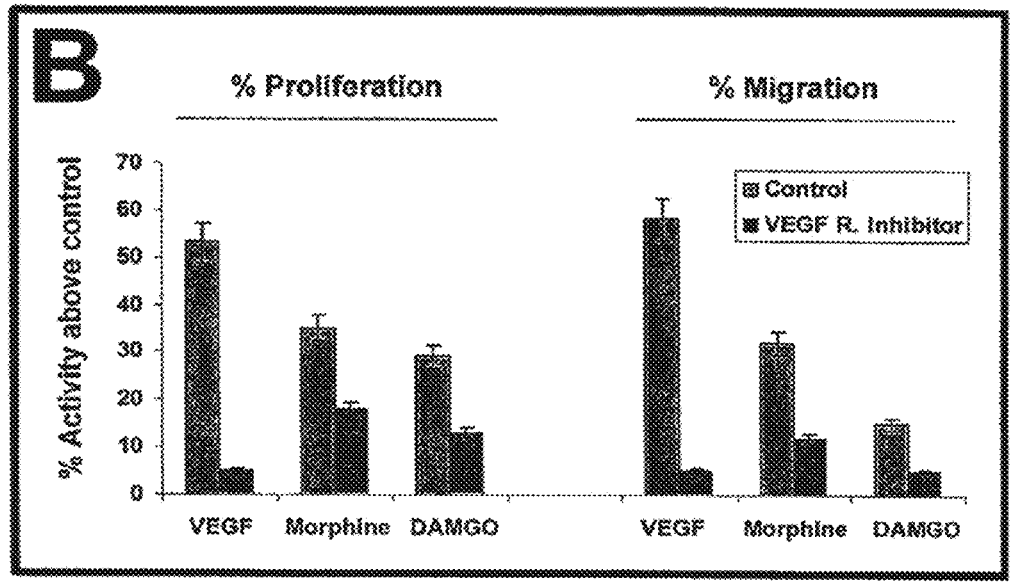
FIGURE 8

A
Immunoblot:     Control   Morphine   DAMGO   VEGF    (5 minutes)
a. Anti-RhoA
Activated RhoA
b. Anti-RhoA
Activated RhoA    + MNTX
c. Anti-RhoA
Total RhoA
B
Morphine (5 minutes)
Immunoblot:    Control   Morphine Alone   VEGF R. Inhibitor
a. Anti-RhoA
Activated RhoA
b. Anti-RhoA
Total RhoA
DAMGO (5 minutes)
Control   DAMGO Alone   VEGF R. Inhibitor
c. Anti-RhoA
Activated RhoA
d. Anti-RhoA
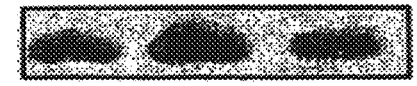
Total RhoA
FIGURE 9

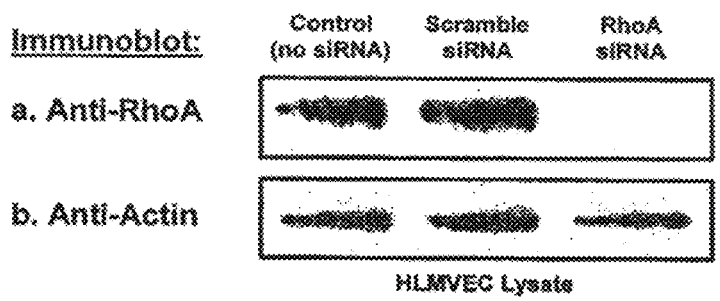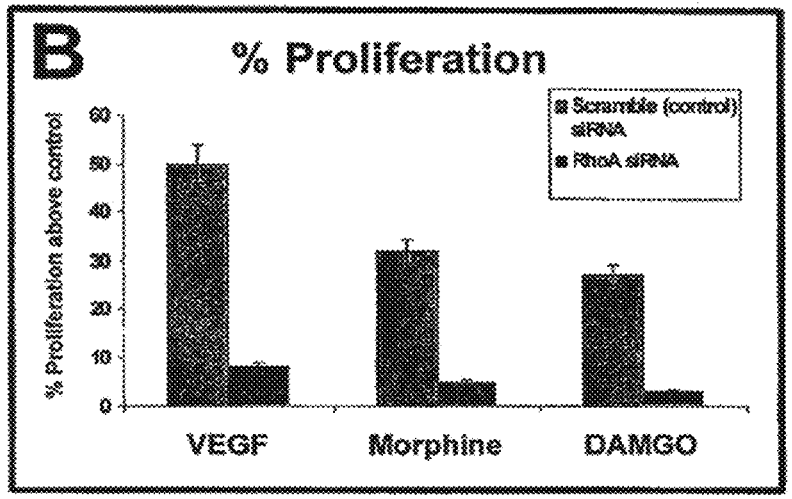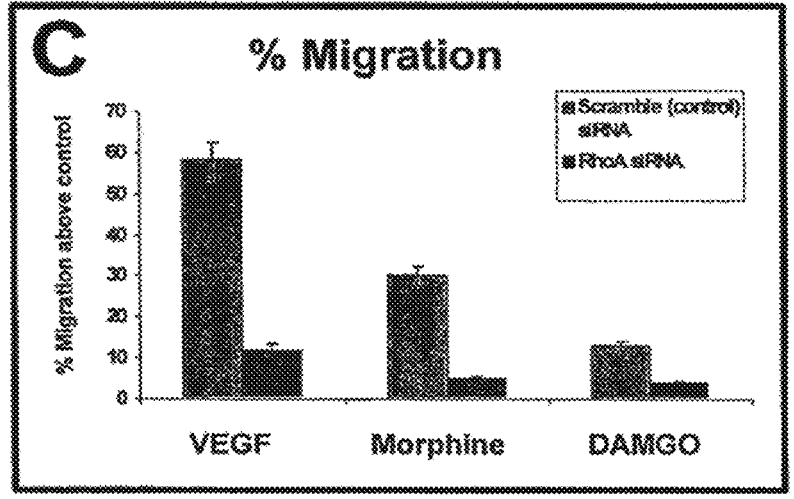
FIGURE 10

US 9,662,325 B2

USE OF OPIOID ANTAGONISTS TO ATTENUATE ENDOTHELIAL CELL PROLIFERATION AND MIGRATION

RELATED APPLICATIONS

This application is a continuation-in-part of U.S. application Ser. No. 13/972,122, filed Aug. 21, 2013, which is a continuation of U.S. application Ser. No. 11/379,010, filed Apr. 17, 2006, now U.S. Pat. No. 8,524,731 issued Sep. 3, 2013, which is a continuation-in-part of PCT Application No. PCT/US2006/07892 filed on Mar. 7, 2006, which claims benefit under 35 U.S.C. 119(e) of the filing dates of U.S. Ser. No. 60/659,193 filed on Mar. 7, 2005, 60/725,703 filed Oct. 12, 2005, 60/731,009 filed on Oct. 28, 2005, and 60/760,851 filed Jan. 20, 2006, the entire disclosures of which are incorporated herein by reference.

STATEMENT REGARDING FEDERAL SPONSORED RESEARCH OR DEVELOPMENT

This invention was supported in part by National Institutes of Health grants: DE12322; DE00470; and DE015830. The United States government has certain rights in this invention.

FIELD OF INVENTION

The invention relates to methods of attenuating migration and/or proliferation of endothelial cells, especially associated with tumors, utilizing opioid antagonists.

INTRODUCTION

Cellular proliferation is a normal ongoing process in all living organisms that involves numerous factors and signals that are delicately balanced to maintain regular cellular cycles. Whether or not mammalian cells will grow and divide is determined by a variety of feedback control mechanism, which includes the availability of space in which a cell can grow, and the secretion of specific stimulatory and inhibitory factors in the immediate environment.

Angiogenesis and angiogenesis-related diseases are affected by cellular proliferation. The process of angiogenesis results in the formation of new blood vessels. Under normal physiological conditions, animals, including humans, undergo angiogenesis only in very specific restricted situations. For example, angiogenesis is normally observed in wound healing, fetal and embryonic development, and formation of the corpus luteum, endometrium and placenta.

During the process of angiogenesis, endothelial cells, which normally exist in a quiescent state as part of an existing blood vessel, enter a migratory, proliferative state. This migratory, proliferative state of endothelial cells is eventually resolved when the cells return to the quiescent state as part of a functional new blood vessel. The generation of new capillaries involves a complex process that requires a number of cellular and molecular events to occur in both a spatial and temporal pattern. Some of these activities include the degradation of the surrounding basement membrane of the originating vessel, the migration of the endothelial cells through the connective tissue stroma, cell proliferation, the formation of tube-like structures, and the maturation of these endothelial-lined tubes into new blood vessels. (Cliff, 1963; Schoefl, 1963; Ausprunck and Folkman, 1977). Some essential angiogenic factors include fibroblast growth factor-basic, vascular endothelial growth factor (VEGF), angiopoietins, cytokines, extracellular matrix proteins, and matrix metalloproteases. These factors are produced locally by stromal cells and by activated leukocytes that are recruited to the area (Risau, W. (1997) Nature 386(6626):671-674; Risau and Flamme (1995) Ann. Rev. Cell Dev. Biol. 11:73-91). Unlike other angiogenic factors, VEGF acts as an endothelial cell specific mitogen during angiogenesis (Terman et al., 1992 and Ferrara, 1993).

Angiogenesis can be stimulated and harnessed by some neoplasms (e.g., tumors) to increase nutrient uptake. It has been found that angiogenesis is essential for the growth of solid tumors beyond 2-3 mm in diameter and for tumor metastasis (Folkman, 1995; reviewed in Bouck et al., 1996). In contrast to normal angiogenesis, which leads to anastomoses and capillary maturation, angiogenesis associated with neoplasia is a continuous process. Endothelial cells are activated by nearby neoplastic cells to secrete not only VEGF which stimulates angiogenesis, but also matrix metalloproteases (MMP) which degrade the surrounding extracellular matrix. The endothelial cells then invade the extracellular matrix where they migrate, proliferate, and organize to form new blood vessels, which support neoplasm growth and survival. The newly vascularized neoplasm continues to grow, leading to further nutrient deprivation and chronic pro-angiogenic signaling. The vasculature of neoplasms is characterized by the presence of lacunae and a low rate of anastomoses. This partially dysfunctional vasculature fuels the permanent requirement for angiogenesis. Additionally, this incomplete vasculature allows the shedding of neoplastic cells into the systemic circulation. Hence, the angiogenic potential of a neoplasm correlates with metastatic potential. (Weidner et al. (1991) N. Engl. J. Med. 324(1):1-8; Folkman and Shing (1992) J. Biol. Chem. 267(16): 10931-10934).

As a significant proportion of neoplasms are dependent on continued angiogenesis, inhibition of angiogenesis blocks neoplasm growth which often leads to complete necrosis of the neoplasm. (Weidner et al. (1991) N. Engl. J. Med. 324(1):1-8; Folkman and Shing (1992) J. Biol. Chem. 267 (16):10931-10934). Suppression of anyone of the steps of and/or factors involved in angiogenesis could inhibit the formation of new vessels, and therefore, affect tumor growth and generation of metastases. Indeed, it has been estimated that the elimination of a single endothelial cell could inhibit the growth of 100 tumor cells (Thorpe et al., 1995). It has also been found that antibodies raised against the angiogenic factor VEGF have been shown to suppress tumor growth in vivo (Kim et al., 1993).

As part of treating and managing patients with cancer and many medical conditions, opioid agonists, such as morphine, are widely used for associated pain. For example, morphine is used in the terminal phase of care of approximately one-half of the patients that die of cancer each year in the United States. Opioid agonists, such as morphine comprise a group of compounds that act on a series of endogenous opioid receptors, such as mu-, kappa-, and delta-receptors in biological systems. Normally, these endogenous receptors bind endogenous opioids. Endogenous opioids are natively produced by mammalian cells.

Endogenous opioids include beta-endorphins, enkephalins, and dynorphins. Beta-endorphins show a preference for mu receptors, enkephalins for delta receptors and dynorphins for kappa receptors. Opioid agonists are classified by their preferential effects on the endogenous opioid receptors. Generally, the mu-receptor is associated with pain relief, and chemical dependence (e.g., drug addiction and alcoholism). Morphine, for example, is a mu-opioid agonist.

Opioid receptors are not limited to the brain and central nervous system (eNS), e.g., to central receptors. Peripheral opioid receptors may be found in other tissues throughout the body, e.g., gastrointestinal tissue.

Despite wide use in pain management, morphine and other opioid medications can have severe side effects that may be caused by activation of the peripheral receptors. The side effects can be difficult to manage and can result in the patient refusing opioid-based pain management. Side effects of opioid treatment include nausea, constipation, inhibition of gastrointestinal motility, respiratory suppression and immunosuppression. Additionally, morphine and other opioid receptor agonists can stimulate human microvascular endothelial cell proliferation and angiogenesis in vitro and in vivo at typical morphine or morphine-equivalent blood concentrations. This pro-angiogenesis activity of the opioid agonists, while palliative for pain, may hasten tumor progression.

Opioid antagonists are similarly classified by their effects on the opioid receptors, e.g., by their ability to antagonize one receptor more effectively than another receptor. For example, the opioid antagonist naloxone acts as a competitive antagonist at all opioid receptors, but is approximately ten times more effective at mu-receptors than at kappa receptors, and is, therefore, classified as a mu-opioid antagonist. Opioid antagonists may antagonize central receptors, peripheral receptors or both. Opioid antagonists, and in particular peripheral opioid antagonists, have been used to lessen the side-effects of exogenously administered opioids, as well as to lessen the unwanted effects of excessive endogenous opioids.

Opioid antagonists also have been examined for their potential use as anticancer agents for particular types of cancer, as described in U.S. Pat. Nos. 6,384,044 and 6,136,780 and in the scientific literature Gupta et al. *Cancer Research,* 62: 4491-98 (2002). The anticancer effects of opioid antagonists have been controversial and not well understood, but it has been held that the opioid antagonist anticancer effects, to the extent they have been shown at all, are unrelated to angiogenesis (Poonawala T, et al., Wound Repair Regen. 2005 March-April; 13(2): 165-74; Popov I., Acta Chirlugosl. 2004; 51(2): 117-21; Blebea J, et al., J Vasc Surg. 2002 March; 35(3):532-8; Balasubramanian S, et al., J Mol Cell Cardiol. 2001 December; 33(12):2179-87; Zagon I S, et al., Int J Oncol. 2000 November; 17(5):1053-61; Blebea J et al., J Vasc Surg. 2000 August; 32(2):364-73; Pasi A, et al., Gen Pharmacol. (991; 22(6):1077-9.) In fact, it has been reported that in xenograft tumor model in mice, the opioid antagonist naloxone did not exhibit a significant effect on morphine induced angiogenesis Gupta et al. *Cancer Research,* 62: 4491-98 (2002). Therefore, it is surprising that it is now discovered that opioid antagonists can inhibit endothelial proliferation and migration associated with angiogenesis.

BRIEF DESCRIPTION OF THE INVENTION

The invention provides methods of attenuating, e.g., inhibiting or reducing, cellular proliferation and migration, particularly endothelial cell proliferation and migration, including that associated with angiogenesis, using opioid antagonists, including, but not limited to, those that are peripherally restricted antagonists.

According to one aspect of the invention, a method of treatment is provided. The method involves administering to a subject with a disorder characterized by unwanted migration or proliferation of endothelial cells an effective amount of an opioid antagonist. The treatment may inhibit one or both of migration and proliferation. The unwanted migration or proliferation of endothelial cells can be unwanted migration or proliferation of vascular endothelial cells, including, but not limited to, unwanted neovascularization or angiogenesis. Examples of unwanted neovascularization include, but are not limited to, neovascularization associated with cancer and ocular neovascularization. The disorder can be any disorder characterized by unwanted migration or proliferation of endothelial cells. Important such disorders are cancer, sickle cell anemia, vascular wounds, proliferative retinopathies, and unwanted endothelial cell proliferation in the kidneys and the lung.

In important embodiments, the opioid antagonist is a peripheral opioid antagonist. Peripheral opioid antagonists include, but are not limited to, quaternary or tertiary morphinan derivatives, piperidine-N-alkylcarboxylates, and quaternary benzomorphans. One important such peripheral opioid antagonist is methylnaltrexone. Another opioid antagonist is alvimopan. In important embodiments, the effective amount is such that the subject has effective circulating blood plasma levels of the opioid antagonist continuously for at least 1 week, at least 2 weeks, at least three weeks and, preferably, at least 4 weeks.

The invention also includes the coadministration of the opioid antagonists with agents that are not opioid antagonists, but which are nonetheless useful in treating disorders characterized by unwanted migration or proliferation of endothelial cells. Examples of such agents include anticancer agents, antineovascularization agents (for example, anti-VEGF monoclonal antibody), antidiabetes agents, antisickle cell agents, wound healing agents, and anthendothelial cell proliferative agents.

It will be understood that the subjects may be, or may not be, on concurrent opioid therapy, depending on the particular disorder the subject has, the severity of the disorder, and the need the subject has for pain management. In some embodiments, the subject is taking concurrent opioid therapy. In some embodiments, the subject is not taking concurrent opioid therapy. In some embodiments, the subject is taking concurrent chronic opioid therapy. In some embodiments, the subject is not taking concurrent chronic opioid therapy.

According to another aspect of the invention, a method of inhibiting VEGF activity in endothelial cells is provided. The method involves contacting the cells with an effective amount of an opioid antagonist.

According to another aspect of the invention, a method of inhibiting exogenous opioid-induced cellular migration or proliferation in endothelial cells is provided. The method involves contacting the cells with an effective amount of an opioid antagonist.

According to another aspect of the invention, a method of inhibiting Rho A activation in endothelial cells is provided. The method involves contacting the cells with an effective amount of an opioid antagonist.

According to any of the foregoing embodiments, the opioid antagonist preferably is a peripheral opioid antagonist, and most preferably is methylnaltrexone.

The invention provides methods of attenuating migration and/or proliferation of endothelial cells of a tumor or cancer, comprising contacting the cells with an antimigratory or antiproliferative amount of an opioid antagonist. In another aspect, the invention provides methods of attenuating angiogenesis associated with cancer. Thus, the invention contemplates treating a human cancer patient, for example, by a method of attenuating angiogenesis in a cancerous tissue of a patient, comprising administering to the cancer tissue of the patient an effective amount of an opioid antagonist.

The invention also provides a method of treating abnormal neovascularization, comprising administering to a patient in need of such treatment, an amount of an opioid antagonist effective to inhibit the formation of blood vessels.

The invention also includes a method of attenuating tumor progression and metastasis in animal tissues, comprising contacting tumor cells or tissues with a growth-inhibiting amount of an opioid antagonist, and a method of attenuating proliferation of hyperproliferative cells in a subject, comprising administering to the subject at least one opioid antagonist, in an amount which is effective to attenuate proliferation of the hyperproliferative cells. In one embodiment, the method involves administering a peripheral opioid antagonist, and, in particular, a quaternary derivative of noroxymorphone, to a subject with cancer, whether or not the cancer involves angiogenesis, to treat or inhibit the development or recurrence of the cancer. Cancers not involving angiogenesis include those that do not involve the formation of a solid tumor fed by neovasculature. Certain blood cell cancers fall into this category, for example: leukemias (cancer of the leukocytes or white cells), lymphomas (arising in the lymph nodes or lymphocytes), and some cancers of the bone marrow elements. Thus, in one aspect of the invention, a method of treatment is provided. The method involves administering to a subject with a disorder characterized by hyperproliferation of cells an effective amount of a peripheral opioid antagonist. In one embodiment, the cells are cancer cells. The cancer cells may be cancer cells associated with angiogenesis or they may be unassociated with angiogenesis. In one embodiment, the peripheral opioid antagonist is methylnaltrexone.

In further embodiments, the invention provides methods of treating cancer, wherein a peripheral opioid antagonist and at least one other therapeutic agent that is not an opioid or opioid antagonist are co-administered to the patient. Suitable therapeutic agents include anticancer agents (including chemotherapeutic agents and antineoplastic agents), as well as other antiangiogenesis agents. It has been discovered that opioid antagonists co-administered with various anticancer drugs, radiotherapy or other antiangiogenic drugs can give rise to a significantly enhanced antiproliferative effect on cancerous cells, thus providing an increased therapeutic effect, e.g., employing peripheral opioid antagonists to certain tumors can potentiate their response to other therapeutic regimens. Specifically, a significantly increased antiproliferative effect, including but not limited to a significantly increased antiangiogenic effect, is obtained with co-administered combinations as described in more detail below. Not only can an existing regimen be enhanced, but new regimens are possible, resulting, for example, in lower concentrations of the anticancer compound, a lower dosing of radiation, or lower concentration of other antiangiogenic drugs, compared to the treatment regimes in which the drugs or radiation are used alone. There is the potential, therefore, to provide therapy wherein adverse side effects associated with the anticancer or other antiangiogenic drugs or radiotherapy are considerably reduced than normally observed with the anticancer or other antiangiogenic drugs or radiotherapy when used alone. Thus, in one aspect of the invention, a method of treatment is provided. The method involves administering to a subject with a disorder characterized by hyperproliferation of cells an effective amount of an opioid antagonist and an anticancer agent, radiation, or an antiangiogenic agent.

In one embodiment, the cells are cancer cells. In one embodiment, the opioid antagonist is a peripheral opioid antagonist. In one embodiment, the peripheral opioid antagonist is methylnaltrexone. In another aspect of the invention, a method of reducing the risk of recurrence of a cancer in a subject after medical intervention is provided. The method involves administering to the subject before, during or after the medical intervention an effective amount of an opioid antagonist and an anticancer agent, radiation, or an antiangiogenic agent. In one embodiment, the opioid antagonist is a peripheral opioid antagonist. In one embodiment, the peripheral opioid antagonist is methylnaltrexone.

In another aspect of the invention, the opioid antagonists are used peri-operatively. By "peri-operatively," it is meant immediately before (e.g., in preparation for), during, and/or immediately after a surgery or a surgical or endoscopic procedure, e.g. colonoscopy, gastrolaparoscopy, and especially a surgery or surgical procedure involving the removal of a tumor. The opioid antagonists act to attenuate the recurrence of and/or the metastasis of the tumor, especially that arising from angiogenesis associated therewith. It is anticipated that the opioid antagonist will preferably be given in a continuous dosing regimen, e.g., a regimen that maintains a minimum, and even more preferably relatively constant, blood level. It is further contemplated that the methods of the present invention may have prophylactic value in certain disorders associated with abnormal angiogenesis. Thus, the invention provides a method of preventing the appearance or re-appearance of a disorder in a mammal, the disorder being characterized by unwanted endothelial cell migration or proliferation, including abnormal angiogenesis, comprising administering to a mammal in need of such treatment, an effective amount of an opioid antagonist, wherein the disorder is a cancer, sickle cell anemia, ocular neovascular diseases, diabetes, ocular retinopathy, or other unwanted endothelial proliferation in kidneys, eye or lung. It will therefore be understood that, as used herein, treating a subject with a disorder characterized by unwanted endothelial cell proliferation or migration includes treating a subject with an active disorder to inhibit or cure the disorder and treating a subject to inhibit a disorder from reoccurring. For example, the subject may have had a solid tumor removed, and the subject may receive the treatment to inhibit the tumor from reoccurring.

In attenuating cell proliferation, the invention provides a method for the treatment of abnormal cell proliferation of a cell expressing vascular endothelial growth factor (VEGF) in a mammal which comprises administering to the mammal a therapeutically effective amount of an opioid antagonist. The invention also includes a method of treating cancerous tissue in a subject comprising, administering to the subject an amount of an opioid antagonist sufficient to inhibit VEGF production in the cancerous tissue, as well as a method of treating angiogenic disease, the method comprising contacting a tissue or a population of endothelial cells with a composition comprising an amount of at least one of an opioid antagonist under conditions effective to inhibit VEGF-induced angiogenesis and to treat angiogenic disease.

In another aspect, the present invention provides a method of inhibiting or reducing angiogenesis, particularly opioid-induced angiogenesis, e.g., of tumor cells, by administrating or providing an opioid antagonist, particularly a peripheral opioid antagonist, to cells undergoing angiogenesis. In further aspect, the invention provides methods of treating opioid-induced angiogenesis in patients receiving opioid treatment or in patients where the angiogenesis is induced by endogenous opioids. The former group is typically cancer patients on opioid-based pain management. The methods comprise administering an opioid antagonist to a patient in an antiangiogenic amount, e.g., an amount sufficient to inhibit or reduce the opioid-induced angiogenesis. In those patients receiving opioid treatment, the opioid and the peripheral opioid antagonist may be co-administered. Peripheral opioid antagonists can, thus, be used to inhibit or reduce the angiogenic effects of opioids on tumor cells, and attenuate the growth of a tumor.

Suitable opioid antagonists generally include heterocyclic amine compounds that belong to several different classes of compounds. For example, one class is suitably tertiary derivatives of morphinan, and in particular, tertiary derivatives of noroxymorphone. In one embodiment, the tertiary derivative of noroxymorphone is, e.g. naloxone or naltrexone.

Suitable peripheral opioid antagonists are also generally heterocyclic amine compounds that may belong to several different classes of compounds. For example, one class is suitably quaternary derivatives of morphinan, and in particular, quaternary derivatives of noroxymorphone. In one embodiment, the quaternary derivative of noroxymorphone is, e.g., N-methylnaltrexone (or simply methylnaltrexone). Another class is N-substituted piperidines. In one embodiment, the N-piperidine is a piperidine-N-alkylcarbonylate, such as, e.g., alvimopan. Another class of compounds which may be of value in the methods of the present invention is quaternary derivatives of benzomorphans.

In some embodiments of the invention, the opioid antagonist may be a mu opioid antagonist. In other embodiments, the opioid antagonist may be a kappa opioid antagonist. The invention also encompasses administration of more than one opioid antagonist, including combinations of mu antagonists, combinations of kappa antagonists and combinations of mu and kappa antagonists, for example, a combination of methylnaltrexone and alvimopan, or a combination of naltrexone and methylnaltrexone.

In further embodiments, the invention provides methods of treating opioid-induced angiogenesis in patients receiving an opioid, wherein a peripheral opioid antagonist and at least one other therapeutic agent that is not an opioid or opioid antagonist are co-administered to the patient. Suitable therapeutic agents include anticancer agents (including chemotherapeutic agents and antineoplastic agents), as well as other antiangiogenesis agents.

In yet another aspect, the invention provides a method of reducing the risk of recurrence of a cancer or tumor after medical intervention (such intervention to include but not be limited to surgery, e.g. pulmonary surgery, surgical and endoscopic procedures, e.g. colonoscopy, gastrolaparoscopy, chemotherapy, etc.), comprising co-administering to a cancer patient an opioid antagonist. Thus, the invention contemplates, for example, a method of minimizing the post-operative recurrence of, e.g., breast cancer in a patient, comprising administering to the patient an effective amount of an opioid antagonist. Peripheral opioid antagonists in accordance with the present invention, e.g., MNTX, can also inhibit VEGF, platelet-derived growth factor (PDGF), or sphingosine I-phosphate (SIP)-stimulated or induced cell proliferation in the endothelial cells.

Further provided herein is a method of enhancing the efficacy of a cancer chemotherapeutic agent in a subject having a cancer, wherein the method comprises administering the cancer chemotherapeutic agent and an opioid antagonist to the subject.

In some embodiments, the chemotherapeutic agent is a tyrosine kinase inhibitor. In some embodiments, the tyrosine kinase inhibitor is an EGFR inhibitor. In some embodiments, the tyrosine kinase inhibitor is erlotinib.

In some embodiments, the chemotherapeutic agent is an anti-microtubule agent. In some embodiments, the anti-microtubule agent is selected from the group consisting of: vinorelbine, paclitaxel, docetaxel, and a combination thereof.

In some embodiments, the chemotherapeutic agent is an antimetabolite. In some embodiments, the antimetabolite is gemcitabine.

Also provided herein is a method of inhibiting cancer progression in a subject, comprising administering a therapeutically effective amount of a chemotherapeutic agent with a therapeutically effective amount of an opioid antagonist. In some embodiments, the chemotherapeutic agent is a tyrosine kinase inhibitor, an anti-microtubule agent or an antimetabolite.

In some embodiments, the opioid antagonist is a peripheral opioid antagonist. In some embodiments, the peripheral opioid antagonist comprises a compound of formula (I). In some embodiments, the peripheral opioid antagonist comprises methylnaltrexone.

BRIEF DESCRIPTION OF DRAWINGS

The invention may be better understood and appreciated by reference to the detailed description of specific embodiments presented herein in conjunction with the accompanying drawings of which:

FIG. 8 is a panel of immunoblots indicating the tyrosine phosphorylation (activation) of (A) of anti-VEGF R.1 (Flt-1) and 2 (Flk-1) using immunoprecipitated VEGF R.1 or 2 and anti-phospho-tyrosine in human pulmonary microvascular endothelial cells in the presence of VEGF, morphine and DAMGO with or without MNTX and a bar graph (B) of percent proliferation and migration of human pulmonary microvascular endothelial cells in the presence of VEGF, morphine and DAMGO with or without VEGF R. inhibitor.

FIG. 9 is a panel of immunoblots indicating RhoA activation using anti-RhoA in human pulmonary microvascular endothelial cells in the presence of VEGF, morphine and DAMGO with or without MNTX (A) or VEGF R. Inhibitor (B).

FIG. 10 is a panel of immunoblots (A) of anti-RhoA of human pulmonary microvascular endothelial cells in the presence of scramble siRNA (targeting no known human mRNA sequence) or RhoA siRNA and a bar graph of percent proliferation (B) and migration (C) of human pulmonary microvascular endothelial cells in the presence of VEGF, morphine and DAMGO with or without scramble siRNA (targeting no known human mRNA sequence) or RhoA siRNA.

DETAILED DESCRIPTION OF THE INVENTION

Figure 1:
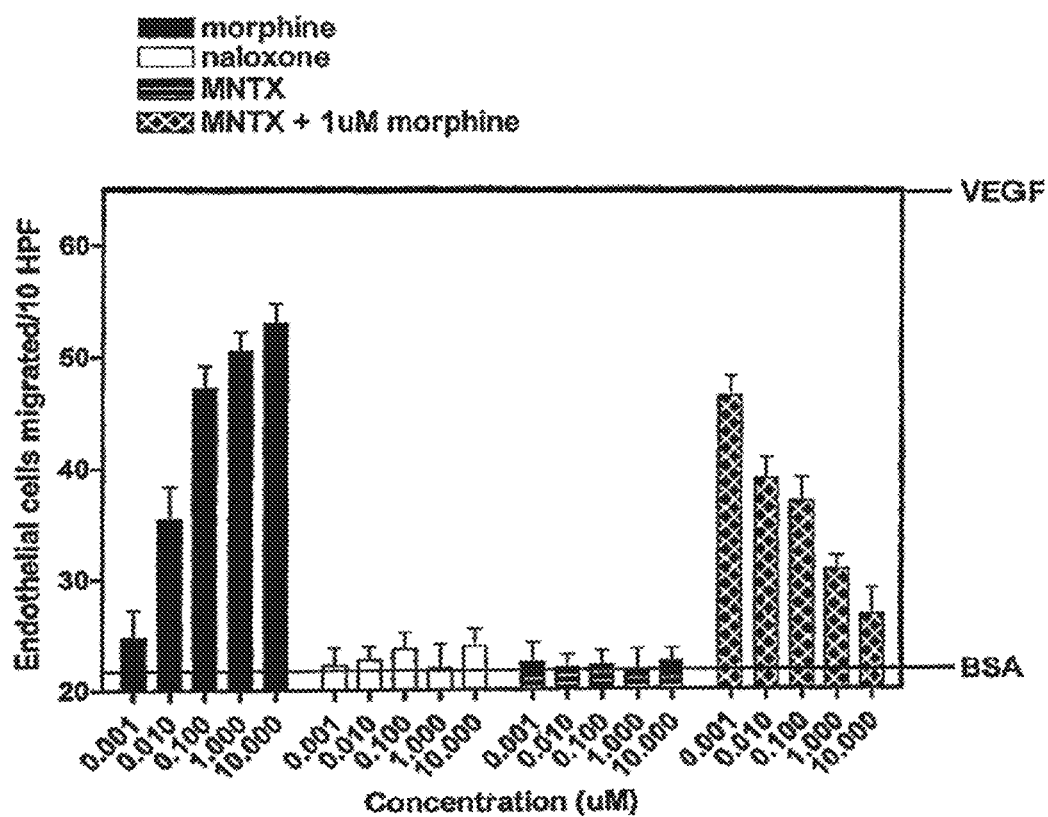
FIG. 1 is a bar graph of dose-dependent inhibition of human microvascular endothelial cell (HMVEC) migration, depicting the results from Example 1.

The present invention provides methods of attenuating abnormal or undesirable migration and/or proliferation of endothelial cells. As such, the invention provides methods for attenuating angiogenesis in a tissue or an organ of a subject by the use of opioid antagonists, and a novel approach for treating angiogenic related diseases and other hyperproliferative diseases in mammals.

For example, as described above, solid tumors rely on the generation of new blood vessels for nutrients to reach the cells within the tumor. The growth factors required for angiogenesis can be produced by the tumor cells or alternatively, exogenous factors, such as opioids can stimulate new blood vessel growth. The present invention by the use of opioid antagonists provides a novel therapeutic approach to the treatment of such tumors, wherein the generation of new blood vessels within the tumor, rather than the tumor cells themselves, is the target. This treatment is not likely to lead to the development of resistant tumor cells.

Described herein are opioid antagonists inhibit proliferation and migration induced by opioids, endogenous or exogenous, and growth factors, such as VEGF, PDGF, S1P etc. Peripheral opioid antagonists, in particular, showed a substantial efficacy in inhibiting opioid and growth factor induced proliferation and migration of endothelial cells. The peripheral opioid antagonist methylnaltrexone (MNTX) inhibited both opioid and growth factor induced proliferation and migration in a concentration dependent manner. In addition, naloxone also inhibited opioid-induced endothelial migration. It should be noted, however, that the naloxone inhibition of DAMGO induced migration of endothelial cells occurred at a relatively high, micromolar, concentration of naloxone. Furthermore, it has now been discovered that opioid antagonists, and the peripheral opioid antagonist MNTX in particular, inhibit agonist induced endothelial cell (EC) proliferation and migration via inhibition of receptor phosphorylation and/or transactivation and subsequent inhibition of Rho A activation. The agonists can be opioids, exogenous and/or endogenous, angiogenic factors (VEGF), and other proliferation and/or migration stimulating factors (PDGF, S1P, S1P$_3$ receptor, RhoA, etc). These results suggest that inhibition of angiogenesis by opioid antagonists can be a useful therapeutic intervention for, among other disorders, cancer.

The present invention also provides methods of attenuating abnormal or undesirable proliferation of cancer cells per se. This aspect of the invention is useful in situations involving the presence or absence of angiogenic activity. The absence of angiogenic activity is evidenced by one or more of the following characteristics: nonsolid tumors or tumors where there is repulsion of existing blood vessels and/or absence of micro vessels within the tumor, limited growth, for example up to about 1 mm in diameter in vivo, at which time further expansion is stopped, harmless to the host until it switches to an angiogenic phenotype, etc. Nonangiogenic tumors can be completely avascular or they can contain empty lumen without red blood cells. The gross difference between the nonangiogenic and angiogenic tumors (i.e. white vs. red tumors) is most likely due to the reactive hyperemia that accompanies the onset of blood flow after the angiogenic switch is completed in a previously hypoxic tumor. Examples of nonangiogenic tumor lineages include but are not limited to breast adenocarcinoma, osteosarcoma, glioblastoma, embryonic kidney tumors etc. There are many factors that could play a role in tumor dormancy and the rate-determining step for tumor expansion of nonangiogenic tumors could be governed by lack of angiogenesis and/or differentiation programs, tumor cell survival, immune response to the host etc. Although some nonagiogenic tumors never switch to an angiogenic phenotype, many undergo spontaneous transformation into an angiogenic and harmful phenotype. Therefore, treatment of nonangiogenic tumors is of therapeutic significance.

Cancers not involving angiogenesis include those that do not involve the formation of a solid tumor fed by neovasculature. Certain blood cell cancers can fall into this category, for example: leukemias, including acute lymphocytic leukemia (ALL), acute myelogenous leukemia (AML), chronic lymphocytic leukemia (CLL), chronic myelogenous leukemia (CML), and hairy cell leukemia; lymphomas (arising in the lymph nodes or lymphocytes) including Hodgkin lymphoma, Burkitt's lymphoma, cutaneous lymphoma, cutaneous T-cell lymphoma, follicular lymphoma, lymphoblastic lymphoma, MALT lymphoma, mantle cell lymphoma, Waldenstrom's macroglobulinemia, primary central nervous system lymphoma; and some cancers of the bone marrow elements including Ewing's sarcoma and osteosarcoma.

Before any embodiments of the invention are explained in detail, it is to be understood that the invention is not limited in its application to the details of the structure and function of the invention set forth in the following description or illustrated in the appended FIGS of the drawing. The invention is capable of other embodiments and of being practiced or carried out in various ways. Also, it is to be understood that the phraseology and terminology used herein is for the purpose of description and should not be regarded as limiting. The use of terms such as "including," "comprising," or "having" and variations thereof herein is meant to encompass the item listed thereafter and equivalents thereof as well as additional items.

Unless otherwise noted, technical terms are used according to conventional usage. As used herein, however, the following definitions may be useful in aiding the skilled practitioner in understanding the invention:

"Subject" refers to humans, dogs, cats, and horses.

"Chronic opioid use" refers to and is characterized by the need for substantially higher levels of opioid to produce the therapeutic benefit as a result of prior opioid use, as is well known in the art. Chronic opioid use as used herein includes daily opioid treatment for a week or more or intermittent opioid use for at least two weeks.

"Alkyl" refers to an aliphatic hydrocarbon group which is saturated and which may be straight, branched or cyclic having from 1 to about 10 carbon atoms in the chain, and all combinations and subcombinations of chains therein. Exemplary alkyl groups include methyl, ethyl, n-propyl, isopropyl, butyl, isobutyl, see-butyl, tert-butyl, pentyl, hexyl, heptyl, octyl, nonyl and decyl.

"Lower alkyl" refers to an alkyl group having 1 to about 6 carbon atoms.

"Alkenyl" refers to an aliphatic hydrocarbon group containing at least one carbon-carbon double bond and having from 2 to about 10 carbon atoms in the chain, and all combinations and sub combinations of chains therein. Exemplary alkenyl groups include vinyl, propenyl, butenyl, pentenyl, hexenyl, heptenyl, octenyl, nonenyl and decenyl groups.

"Alkynyl" refers to an aliphatic hydrocarbon group containing at least one carbon-carbon triple bond and having from 2 to about 10 carbon atoms in the chain, and combinations and sub combinations of chains therein. Exemplary alkynyl groups include ethynyl, propenyl, butenyl, pentenyl, hexenyl, heptenyl, octenyl, nonenyl and decenyl groups.

"Alkylene" refers to a bivalent aliphatic hydrocarbon group having from 1 to about 6 carbon atoms, and all combinations and subcombinations of chains therein. The alkylene group may be straight, branched or cyclic. There may be optionally inserted along the alkylene group one or more oxygen, sulfur or optionally substituted nitrogen atoms, wherein the nitrogen substituent is alkyl as described previously.

"Alkenylene" refers to an alkylene group containing at least one carbon-carbon double bond. Exemplary alkenylene groups include ethenylene (—CH=CH—) and propenylene (CH=CHCH$_2$—).

"Cycloalkyl" refers to any stable monocyclic or bicyclic ring having from about 3 to about 10 carbons, and all combinations and subcombinations of rings therein. The cycloalkyl group may be optionally substituted with one or more cycloalkyl-group substituents. Exemplary cycloalkyl groups include cyclopropyl, cyclobutyl, cyclopentyl, cyclohexyl, cycloheptyl and cyclooctyl groups.

"Cycloalkyl-substituted alkyl" refers to a linear alkyl group, preferably a lower alkyl group, substituted at a terminal carbon with a cycloalkyl group, preferably a C3-C8 cycloalkyl group. Exemplary cycloalkyl-substituted alkyl groups include cyclohexylmethyl, cyclohexylethyl, cyclopentylethyl, cyclopentylpropyl, cyclopropylmethyl and the like.

"Cycloalkenyl" refers to an olefinically unsaturated cycloaliphatic group having from about 4 to about 10 carbons, and all combinations and subcombinations of rings therein.

"Alkoxy" refers to an alkyl-O-group where alkyl is as previously described. Exemplary alkoxy groups include, for example, methoxy, ethoxy, propoxy, butoxy and heptoxy.

"Alkoxy-alkyl" refers to an alkyl-O-alkyl group where alkyl is as previously described.

"Acyl" means an alkyl-CO group wherein alkyl is as previously described. Exemplary acyl groups include acetyl, propanoyl, 2-methylpropanoyl, butanoyl and palmitoyl.

"Aryl" refers to an aromatic carbocyclic radical containing from about 6 to about 10 carbons, and all combinations and subcombinations of rings therein. The aryl group may be optionally substituted with one or two or more aryl group substituents. Exemplary aryl groups include phenyl and naphthyl.

"Aryl-substituted alkyl" refers to a linear alkyl group, preferably a lower alkyl group, substituted at a terminal carbon with an optionally substituted aryl group, preferably an optionally substituted phenyl ring. Exemplary aryl-substituted alkyl groups include, for example, phenylmethyl, phenyl ethyl and 3-(4-methylphenyl)propyl.

"Heterocyclic" refers to a monocyclic or multicyclic ring system carbocyclic radical containing from about 4 to about 10 members, and all combinations and subcombinations of rings therein, wherein one or more of the members of the ring is an element other than carbon, for example, nitrogen, oxygen or sulfur. The heterocyclic group may be aromatic or nonaromatic. Exemplary heterocyclic groups include, for example, pyrrole and piperidine groups.

"Halo" refers to fluoro, chloro, bromo or iodo.

"Peripheral," in reference to opioid antagonists, designates opioid antagonists that act primarily on physiological systems and components external to the central nervous system, e.g., they do not readily cross the blood-brain barrier in an amount effective to inhibit the central effects of opioids. In other words, peripheral opioid antagonists do not effectively inhibit the analgesic effects of opioids when administered peripherally, e.g., they do not reduce the analgesic effect of the opioids. For example, the peripheral opioid antagonist compounds employed in the methods of the present invention exhibit high levels of activity with respect to gastrointestinal tissue, while exhibiting reduced or substantially no central nervous system (CNS) activity. The peripheral opioid antagonist compounds employed in the present methods suitably exhibit less than about 15% of their pharmacological activity in the CNS, with about 0% (e.g., no CNS activity) being most suitable. The non-central acting characteristic of a peripheral opioid antagonist is often related to charge, polarity and/or size of the molecule. For example, peripherally-acting quaternary amine opioid antagonists are positively charged while the central-acting tertiary amine opioid antagonists are neutral molecules. The peripheral opioid antagonists useful in the present invention are typically mu and/or kappa opioid antagonists.

As used herein, "antiangiogenesis" or "antiangiogenic" is meant to refer to the capability of a molecule/compound to attenuate, e.g., inhibit, reduce or modulate, proliferation of new blood vessels, in general, and for example, to reduce or inhibit migration and proliferation of human microvascular endothelial cells in culture in the presence of certain growth factors. As described above, the formation of new blood vessels by endothelial cells involves migration, proliferation and differentiation of the cells.

In the following description of the methods of the invention, process steps are carried out at room temperature and atmospheric pressure unless otherwise specified. It also is specifically understood that any numerical range recited herein includes all values from the lower value to the upper value, e.g., all possible combinations of numerical values between the lowest value and the highest value enumerated are to be considered to be expressly stated in this application. For example, if a concentration range or beneficial effect range is stated as 1% to 50%, it is intended that values such as 2% to 40%, 10% to 30%, or 1% to 3%, etc., are expressly enumerated in this specification. These are only examples of what is specifically intended.

In one aspect, the present invention relates to methods of attenuating abnormal or undesirable cellular, particularly endothelial cell migration and/or proliferation, and angiogenesis in tissue or an organ of a subject. The methods comprise providing or administering one or more opioid antagonists in an effective amount to endothelial cells of the tissue or organ of a patient to inhibit endothelial cell migration and proliferation, and angiogenesis. The angiogenesis may, in part, be the result of receiving opioid treatment, particularly for pain management in cancer patients, or having high levels of endogenous opioids.

Figure 2:
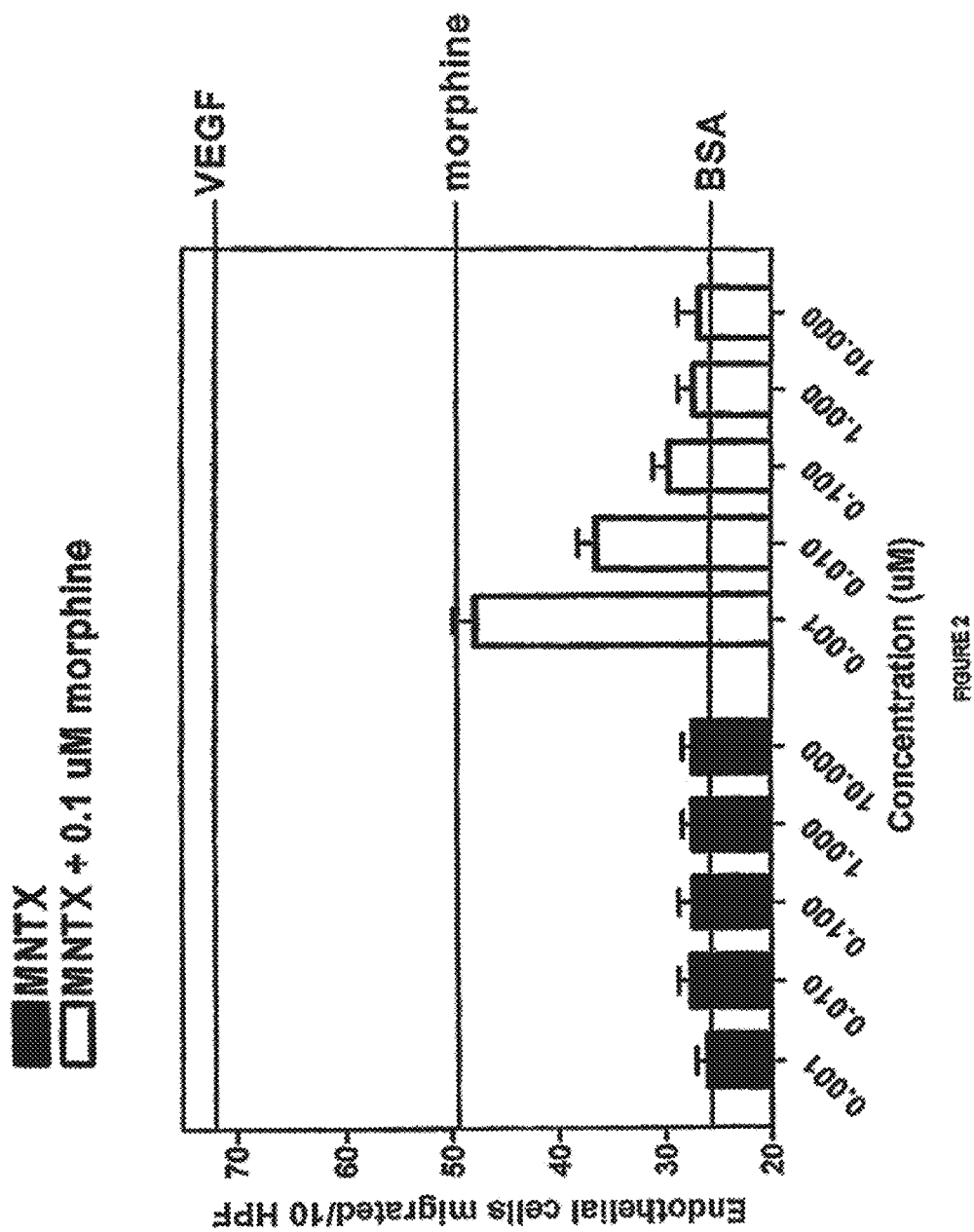
FIG. 2 is a bar graph of dose-dependent inhibition of human microvascular endothelial cell migration, depicting the results from Example 2.
Figure 3:
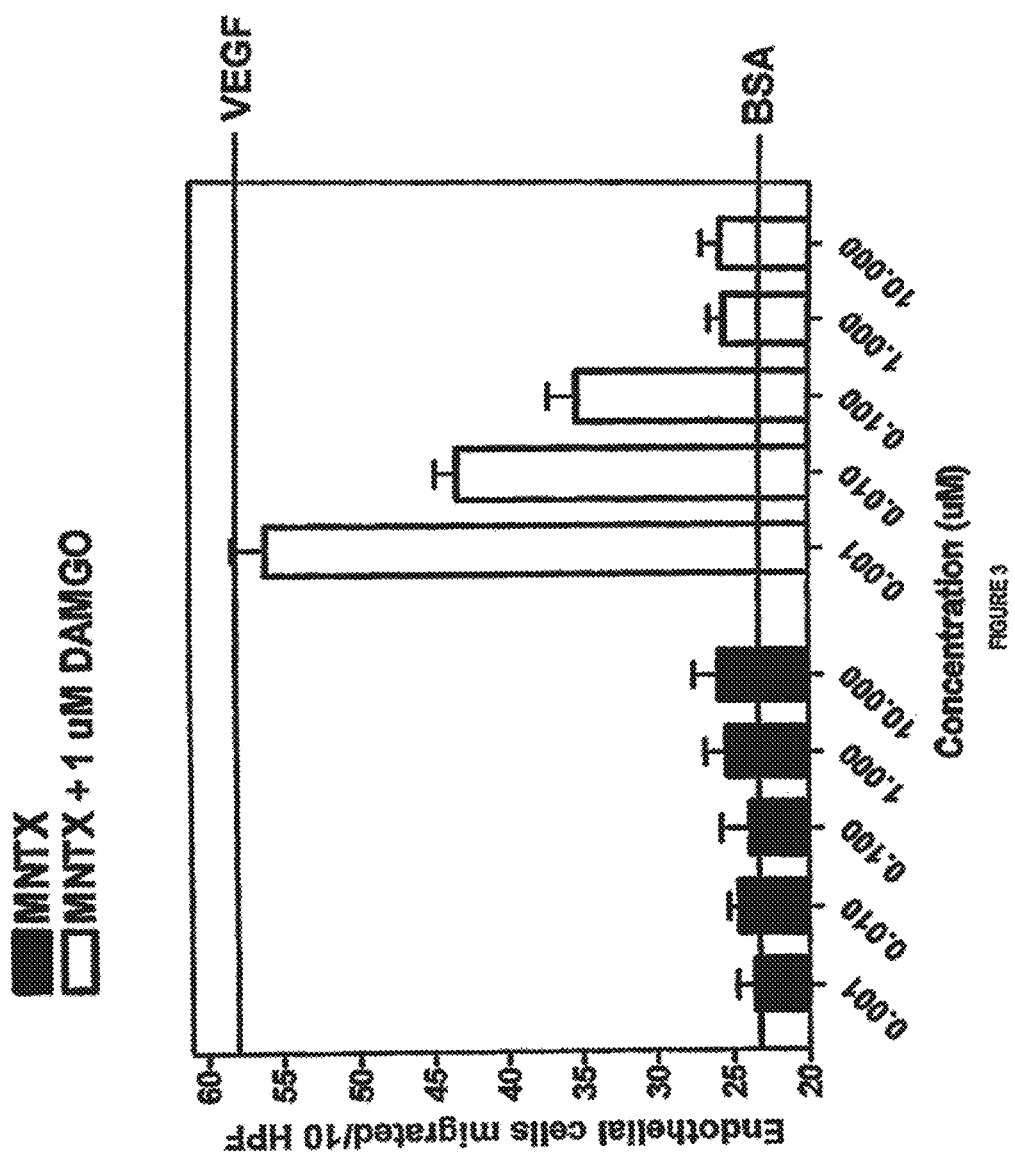
FIG. 3 is a bar graph of dose-dependent inhibition of HMVEC migration using MNTX and MNTX+DAMGO.

It was observed that morphine and the mu agonist enkephalin DAMGO ([D-Ala$^2$, N-McPhe$^4$ Gly$^5$-ol]enkephalin), each cause a dose-dependent increase in migration of endothelial cells similar to that of vascular endothelial growth factor (VEGF) as measured by, e.g., a chemotaxis assay (as detailed in the examples below) or other similar assays used to identify factors in tumor angiogenesis and the drugs that affect it. At clinically relevant concentrations of morphine, the magnitude of the effect is approximately 70% of that which is achieved by VEGF. This morphine-based endothelial cell migration is attenuated by the mu opioid antagonist methylnaltrexone (MNTX) in a dose-dependent fashion. For example, endothelial cell migration induced by morphine, in concentrations as low as $10^{-7}$M, is significantly blocked by $10^{-7}$M MNTX (FIG. 2). This attenuation strongly suggesting that endothelial cell migration is mediated by morphine action on the mu opioid receptor (MOR). As described in the examples below, the effect via the MOR rather than other opioid receptors is confirmed by experiments that show the highly selective synthetic enkephalin mu agonist DAMGO also induces migration. The migratory effect induced by DAMGO is also blocked by MNTX (FIG. 3).

In one comprehensive review (Neumann et al. Pain 1982; 13:247-52), analgesia in cancer patients was associated with a range of steady state concentrations of morphine and plasma ranging from 6 to 364 ng/mL. It was observed an effect of morphine that causes endothelial cell migration at 100 ng/mL well within the clinical dose range. It therefore is believed by the inventors herein that a dose of MNTX which will maintain plasma levels of MNTX at minimum levels of plasma MNTX between about 25 and 150 ng/mL would be suitable. Such doses are attainable and are well tolerated (Yuan et al., J Clin Pharmacol 2005; 45:538-46).

Alvimopan, another selective peripheral opioid antagonist given orally, is in late stage development for prophylaxis of postoperative ileus and the management of opioid induced constipation (Moss et al., Pain relief without side effects: peripheral opioid antagonists. In Schwartz, A J., editor. 33rd ASA Refresher Course in Anesthesiology. Philadelphia: Lippincott Williams & Wilkins (in press).) There is some transpassage of alvimopan across the membrane (J. Foss, et al., Clin. Pharm. & Ther. 2005, PII-90, p. 74) and it may, therefore, possess the ability to reverse some of the systemic effects of opioids without affecting analgesia even when given orally.

Without being bound by any particular theory, it may be that the mechanism of mu opioid effect on endothelial cell migration occurs at the membrane level as MNTX, unlike naloxone, is a charged molecule at physiological pH. Morphine acts via G-protein coupled receptors, while VEGF acts by receptor tyrosine kinases. While the actions of mu agonists and VEGF may be independent, there is growing evidence of receptor transactivation as a mechanism. A prior investigation demonstrated that pertussis toxin dependent GPCRs transactivate VEGF receptor-2/F1 K1 (Zeng, H. et al., J. Biol. Chem. 2003; 278:20738-45). By this manner morphine could transactivate F11 c-1 and promote an environment where endothelial cell proliferation and tumor growth could occur. A recent study of MOR knockout mice infected with T241 fibrosarcoma cells demonstrated significant differences in the incidences of tumor growth and a 10-fold increase in F11 c-1 expression in morphine treated mice versus controls, versus no increase in morphine treated KO mice (K. Gupta, personal communication). This provides further evidence that morphine stimulates endothelial cell proliferation and promotes tumor growth probably by trans activating FLK1 phosphorylation. As such, the present invention provides potential clinical strategies using MNTX as well as other peripheral opioid antagonist in conjunction with current therapies targeting VEGF. Although a direct effect by receptor transactivation is possible, a potential additional factor involved in the proliferation of tumors may well be the role of chemokines as integrators of pain and inflammation. A recent review on this subject (White et al., Nature Rev. Drug Discovery 2005; 4:834-44) also suggests a possible role for leukocytes in activating opioid receptors.

Furthermore, it was observed that morphine, DAMGO and VEGF stimulate RhoA activation which is inhibited by opioid antagonists, such as MNTX. RhoA is an important signaling molecule involved in angiogenesis (Aepfelbacher et al., 1997; Cascone et al., 2003; Hoang et al., 2004; Liu and Sanger, 2004.) VEGF receptor transactivation is important for opiate-induced RhoA activation. Silencing RhoA expression blocked opioid and VEGF induced EC proliferation and migration, demonstrating a role for RhoA activation in agonist-induced EC angiogenic activity. The MNTX mediated attenuation of RhoA activation may be important for the inhibitory role of MNTX on opioid and VEGF induced angiogenesis.

Because morphine and other opioids at clinical doses enhance endothelial cell migration, the present invention may be of therapeutic value in opioid antagonist treatment for patients on significant and sustained doses of opioids that have tumors relying on the angiogenic process. Further, while the inventor's clinical observations have focused on morphine, which is exogenously administered, endogenous opioids, which are released by stress or pain, may also play a role in endothelial cell migration. Based on endothelial cell migration experiments detailed below in the examples, MNTX and opioid antagonists generally are of therapeutic value as an antiangiogenic therapy even absent exogenous opioid administration (as detailed herein). It is envisioned that the methods of the present invention will inhibit or reduce the growth of blood vessels within and to a tumor. Inhibiting the growth of blood vessels within tumors prevents nutrients and oxygen from being supplied to the tumor to support growth beyond a certain size. Minimizing the number of blood vessels or other tumors also lessens the probability that the tumor will metastasize.

Multidrug resistance, an important mechanism by which many cancers develop resistance to chemotherapeutic drugs, is a major contributing factor to the failure of cancer drug therapy. It affects patients with a variety of cancers including lung, breast, ovarian and lower gastrointestinal tract cancers. Resistance to therapy is regulated by at least two classes of molecular pumps in tumor-cell plasma membranes that actively expel chemotherapeutic drugs from inside the cell. This allows tumor cells to avoid the toxic effects of the drugs and promotes multidrug resistance. The two pumps commonly found in cancer are P-glycoprotein and the multidrug resistance-associated proteins (MRP) that belong to the ATP-binding cassette (ABC) transporters. A major MRP expressed in NSCLC is ABCC3. Morphine may promote drug resistance to a variety of chemotherapeutic agents with different mechanisms of action including tyrosine kinase inhibitor, microtubule modifying agents and DNA synthesis inhibitor. Among other things, the present invention may be useful to reverse the multidrug resistance effects of morphine.

The present invention may be of therapeutic value in opioid antagonist treatment for patients who have tumors relying on the angiogenic process. Tumors that rely on angiogenic processes are solid tumors, leukemias and myelomas. Solid tumors include, but are not limited to adrenal cortical carcinoma, tumors of the bladder: squamous cell carcinoma, urothelial carcinomas; tumors of the bone: adamantinoma, aneurysmal bone cysts, chondroblastoma, chondroma, chondromyxoid fibroma, chondrosarcoma, fibrous dysplasia of the bone, giant cell tumour, osteochondroma, osteosarcoma; breast tumors: secretory ductal carcinoma, chordoma; colon tumors: colorectal adenocarcinoma; eye tumors: posterior uveal melanoma, fibrogenesis imperfecta ossium, head and neck squamous cell carcinoma; kidney tumors: chromophobe renal cell carcinoma, clear cell renal cell carcinoma, nephroblastoma (Wilms tumor), kidney: papillary renal cell carcinoma, primary renal ASPS CR 1-TFE3 tumor, renal cell carcinoma; liver tumors: hepatoblastoma, hepatocellular carcinoma; lung tumors: non-small cell carcinoma, small cell cancer; malignant melanoma of soft parts; nervous system tumors: medulloblastoma, meningioma, neuroblastoma, astrocytic tumors, ependymomas, peripheral nerve sheath tumors, phaeochromocytoma; ovarian tumors: epithelial tumors, germ cell tumors, sex cord-stromal tumors, pericytoma; pituitary adenomas; rhabdoid tumor; skin tumors: cutaneous benign fibrous histiocytomas; smooth muscle tumors: intravenous leiomyomatosis; soft tissue tumors: liposarcoma, myxoid liposarcoma, low grade fibromyxoid sarcoma, leiomyosarcoma, alveolar soft part sarcoma, angiomatoid fibrous histiocytoma (AFH), clear cell sarcoma, desmoplastic small round cell tumor, elastofibroma, Ewing's tumors, extraskeletal myxoid chondrosarcoma, inflammatory myofibroblastic tumor, lipoblastoma, lipoma/benign lipomatous tumors, liposarcoma/malignant lipomatous tumors, malignant myoepithelioma, rhabdomyosarcoma, synovial sarcoma, squamous cell cancer; tumors of the testis: germ cell tumors, spermatocytic seminoma; thyroid tumors: anaplastic (undifferentiated) carcinoma, oncocytic tumors, papillary carcinoma; uterus tumors: carcinoma of the cervix, endometrial carcinoma, leiomyoma etc.

In one embodiment of the invention the tumors are prostate cancer, gastrointestinal tumors such as colon or pancreatic cancer and the compounds of the invention are co-administered with other anticancer agents as described herein.

The opioid antagonists in accordance with the present invention include both centrally and peripherally acting opioid antagonists. It is contemplated that those antagonists of particular value are suitably the peripheral opioid antagonists. Especially suitable may be a mu opioid antagonist, especially a mu peripheral opioid antagonist. Opioid antagonists form a class of compounds that can vary in structure while maintaining the peripheral restrictive property. These compounds include tertiary and quaternary morphinans, in particular noroxymorphone derivatives, N-substituted piperidines, and in particular, piperidine-N-alkylcarboxylates, and tertiary and quaternary benzomorphans. Peripherally restricted antagonists, while varied in structure, are typically charged, polar and/or of high molecular weight, each of which impedes their crossing the blood-brain barrier.

Examples of opioid antagonists, which cross the blood-brain barrier and are centrally (and peripherally) active, include, e.g., naloxone, naltrexone (each of which is commercially available from Baxter Pharmaceutical Products, Inc.) and nalmefene (available, e.g., from DuPont Pharma). These may be of value in attenuating angiogenesis in the central nervous system or in patients not being treated for pain management or other opioid treatment.

A peripheral opioid antagonist useful for the present invention may be a compound which is a quaternary morphinan derivative, and in particular, a quaternary noroxymorphone of formula (I):

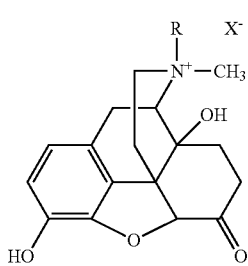

wherein R is alkyl, alkenyl, alkynyl, aryl, cycloalkyl-substituted alkyl or aryl-substituted alkyl, and X' is the anion, especially a chloride, bromide, iodide or methylsulfate anion. The noroxymorphone derivatives of formula (I) can be prepared, for example, according to the procedure in U.S. Pat. No. 4,176,186, which is incorporated herein by reference; see also, U.S. Pat. Nos. 4,719,215; 4,861,781; 5,102,887; 5,972,954 and 6,274,591, U.S. Patent Application Nos. 2002/0028825 and 2003/0022909; and PCT publication Nos. WO 99/22737 and WO 98/25613, all of which are hereby incorporated by reference.

A compound of formula (I) of particular value is N-methylnaltrexone (or simply methylnaltrexone), wherein R is cyclopropylmethyl as represented in formula (II):

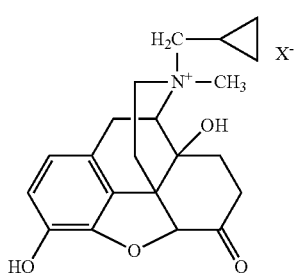

wherein X— is as described above. Methylnaltrexone is a quaternary derivative of the opioid antagonist naltrexone. Methylnaltrexone exists as a salt, and "methylnaltrexone" or "MNTX", as used herein, therefore embraces salts. "Methylnaltrexone" or "MNTX" specifically includes, but is not limited to, bromide salts, chloride salts, iodide salts, carbonate salts, and sulfate salts of methylnaltrexone. Names used for the bromide salt of MNTX in the literature include: methylnaltrexone bromide; N-methylnaltrexone bromide; naltrexone methobromide; naltrexone methyl bromide; SC-37359, MRZ-2663-BR, and N-cyclopropylmethyl-noroxy-morphine-methobromide. Methylnaltrexone is commercially available from, e.g., Mallinclaodt Pharmaceuticals, St. Louis, Mo. Methylnaltrexone is provided as a white crystalline powder, freely soluble in water, typically as the bromide salt. The compound as provided is 99.4% pure by reverse phase HPLC, and contains less than 0.011% unquaternized naltrexone by the same method. Methylnaltrexone can be prepared as a sterile solution at a concentration of, e.g., about 5 mg/mL.

Other suitable peripheral opioid antagonists may include N-substituted piperidines, and in particular, piperidine-N-alkylcarboxylates as represented by formula (III):

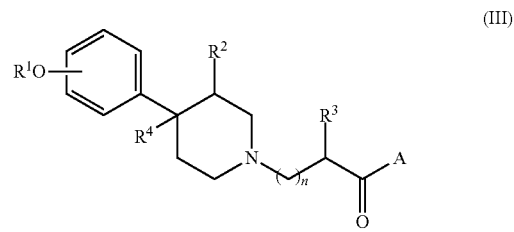

wherein
$R^1$ is hydrogen or alkyl;
$R^2$ is hydrogen, alkyl, or alkenyl;
$R^3$ is hydrogen, alkyl, alkenyl, aryl, cycloalkyl, cycloalkenyl, cycloalkyl-substituted alkyl, cycloalkenyl-substituted alkyl or aryl-substituted alkyl;
$R^4$ is hydrogen, alkyl, or alkenyl;
A is $OR^5$ or $NR^6R^7$; wherein
$R^5$ is hydrogen, alkyl, alkenyl, cycloalkyl, cycloalkenyl, cycloalkyl-substituted alkyl, cycloalkenyl-substituted alkyl or aryl-substituted alkyl;
$R^6$ is hydrogen or alkyl;
$R^7$ is hydrogen, alkyl, alkenyl, aryl, cycloalkyl, cycloalkenyl, cycloalkyl-substituted alkyl, cycloalkenyl-substituted alkyl or aryl-substituted alkyl, or alkylene-substituted B or together with the nitrogen atom to which they are attached, $R^6$ and $R^7$ form a heterocyclic ring selected from pyrrole and piperidine; B is

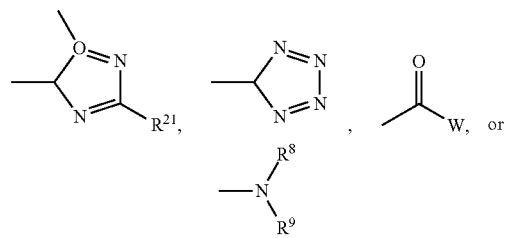

wherein $R^8$ is hydrogen or alkyl;
$R^9$ is hydrogen, alkyl, alkenyl, aryl, cycloalkyl, cycloalkenyl, cycloalkyl-substituted alkyl, cycloalkenyl-substituted alkyl or aryl-substituted alkyl or together with the nitrogen atom to which they are attached, $R^8$ and $R^9$ form a heterocyclic ring selected from pyrrole and piperidine;
W is $OR^{10}$, $NR^{11}R^{12}$, or OE; wherein
$R^{10}$ is hydrogen, alkyl, alkenyl, cycloalkyl, cycloalkenyl, cycloalkyl-substituted alkyl, cycloalkenyl-substituted alkenyl, or aryl-substituted alkyl;
$R^{11}$ is hydrogen or alkyl;
$R^{12}$ is hydrogen, alkyl, alkenyl, aryl, cycloalkyl, cycloalkenyl, cycloalkyl-substituted alkyl, cycloalkenyl-substituted alkyl, aryl-substituted alkyl or alkylene-substituted C(=O)Y or, together with the nitrogen atom to which they are attached, $R^{11}$ and $R^{12}$ form a heterocyclic ring selected from pyrrole and piperidine;

E is

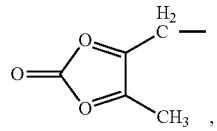

alkylene-substituted (C=O)D, or —$R^{13}$OC(=O)$R^{14}$; wherein $R^{13}$ is alkyl-substituted alkylene;
$R^{14}$ is alkyl;
D is $OR^{16}$ or $NR^{16}R^{17}$; wherein
$R^{15}$ is hydrogen, alkyl, alkenyl, cycloalkyl, cycloalkenyl, cycloalkyl-substituted alkyl, cycloalkenyl substituted alkyl, or aryl-substituted alkyl;
$R^{16}$ is hydrogen, alkyl, alkenyl, aryl, aryl-substituted alkyl, cycloalkyl, cycloalkenyl, cycloalkyl substituted alkyl or cycloalkenyl-substituted alkyl;
$R^{17}$ is hydrogen or alkyl or, together with the nitrogen atom to which they are attached, $R^{16}$ and $R^{17}$ form a heterocyclic ring selected from the group consisting of pyrrole or piperidine;
Y is $OR^{18}$ or $NR^{19}R^{20}$; wherein
$R^{18}$ is hydrogen, alkyl, alkenyl, cycloalkyl, cycloalkenyl, cycloalkyl-substituted alkyl, cycloalkenyl-substituted alkyl, or aryl-substituted alkyl;
$R^{19}$ is hydrogen or alkyl;
$R^{20}$ is hydrogen, alkyl, alkenyl, aryl, cycloalkyl, cycloalkenyl, cycloalkyl-substituted alkyl, cycloalkenyl-substituted alkyl, or aryl-substituted alkyl or, together with the nitrogen atom to which they are attached, $R^{19}$ and $R^{20}$ form a heterocyclic ring selected from pyrrole and piperidine;
$R^{21}$ is hydrogen or alkyl;
and n is 0 to 4.

Particular piperidine-N-alkylcarbonylates which may be of value are N-alkylamino-3,4,4 substituted piperidines, such as alvimopan represented below as formula (IV):

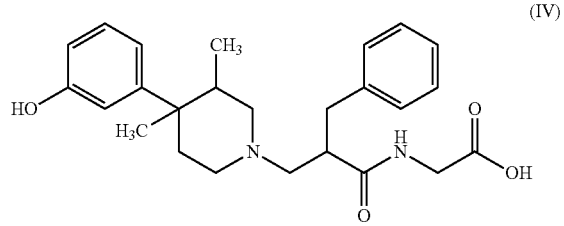 [SMILES: CC1CN(CC(Cc2ccccc2)C(=O)NCC(=O)O)CCC1(C)c1cccc(O)c1]

Suitable N-substituted piperidines may be prepared as disclosed in U.S. Pat. Nos. 5,270,328; 6,451,806; 6,469,030, all of which are hereby incorporated by reference. Alvimopan is available from Adolor Corp., Exton, Pa. Such compounds have moderately high molecular weights, a zwitterion form and a polarity which prevent penetration of the blood-brain barrier.

Still other suitable peripheral opioid antagonist compounds may include quaternary benzomorphan compounds. The quaternary benzomorphan compounds employed in the methods of the present invention exhibit high levels of morphine antagonism, while exhibiting reduced, and preferably substantially no, agonist activity.

The quaternary benzomorphan compounds which may be employed in the methods of the present invention have the following formula (V):

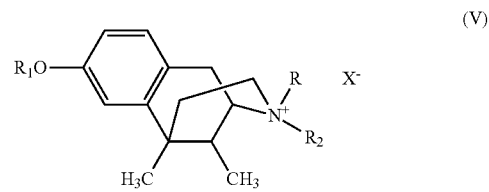

wherein;
$R^1$ is hydrogen, acyl or acetoxy; and
$R^2$ is alkyl or alkenyl;
R is alkyl, alkenyl or alkynyl and
$X^-$ is an anion, especially a chloride, bromide, iodide or methylsulfate anion.

Specific quaternary derivatives of benzomorphan compounds that may be employed in the methods of the present invention include the following compounds of formula (V): 2'-hydroxy 5,9-dimethyl-2,2-diallyl-6,7-benzomorphanium-bromide; 2'-hydroxy-5,9-dimethyl-2-n-propyl-2 ally 1-6,7-benzomorphanium-bromide; 2'-hydroxy-5,9-dimethyl-2-n-propyl-2-propargyl-6, 7 benzomorphanium-bromide; and 2'-acetoxy-5,9-dimethyl-2-n-propyl-2-ally)-6,7 benzomorphanium-bromide.

Other quaternary benzomorphan compounds that may be employed in the methods of the present invention are described, for example, in U.S. Pat. No. 3,723,440, the entire disclosure of which is incorporated herein by reference. The compounds employed in the methods of the present invention may exist in prodrug form. As used herein, "prodrug" is intended to include any covalently bonded carriers which release the active parent drug according to formulas (I) to (V) or other formulas or compounds employed in the methods of the present invention in vivo when such prodrug is administered to a mammalian subject. Since prodrugs are known to enhance numerous desirable qualities of pharmaceuticals (e.g., solubility, bioavailability, manufacturing, etc.), the compounds employed in the present methods may, if desired, be delivered in prodrug form. Thus, the present invention contemplates methods of delivering prodrugs. Prodrugs of the compounds employed in the present invention may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively.

Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

As noted, the compounds employed in the methods of the present invention may be prepared in a number of ways well known to those skilled in the art. All preparations disclosed in association with the present invention are contemplated to be practiced on any scale, including milligram, gram, multigram, kilogram, multikilogram or commercial pharmaceutical scale.

Compounds employed in the present methods may contain one or more asymmetrically substituted carbon atom, and may be isolated in optically active or racemic form. Thus, all chiral, diastereomeric, racemic form, epimeric form and all geometric isomeric form of a structure are intended, unless the specific stereochemistry or isomeric form is specifically indicated. It is well known in the art how to prepare and isolate such optically active form. For example, mixtures of stereo isomers may be separated by standard techniques including, but not limited to, resolution of racemic form, normal, reverse-phase, and chiral chromatography, preferential salt formation, recrystallization, and the like, or by chiral synthesis either from chiral starting materials or by deliberate synthesis of target chiral centers.

In some embodiments of the invention, the opioid antagonist may be a mu opioid antagonist. In other embodiments, the opioid antagonist may be a kappa opioid antagonist. The invention also encompasses administration of more than one opioid antagonist, including combinations of mu antagonists, combinations of kappa antagonists and combinations of mu and kappa antagonists, for example, a combination of methylnaltrexone and alvimopan.

The methods of the present invention encompass providing a therapeutic or prophylactic role in other endothelial-based diseases, e.g., in a variety of angiogenesis and/or proliferation-related neoplastic and non-neoplastic diseases, e.g., sickle cell disease, neovascular disease of the eye (such as diabetic retinopathy, neovascular glaucoma, retinopathy of prematurity, age-related macular degeneration), endothelial proliferation in the kidneys or lung and psoriasis. Non-neoplastic conditions that are amenable to treatment include rheumatoid arthritis, psoriasis, atherosclerosis, diabetic and other proliferative retinopathies including retinopathy of prematurity, retrolental fibroplasia, neovascular glaucoma, age-related macular degeneration, thyroid hyperplasias (including Grave's disease), corneal and other tissue transplantation, chronic inflammation, lung inflammation, nephrotic syndrome, preeclampsia, ascites, pericardial effusion (such as that associated with pericarditis), and pleural effusion. For example, it has been shown that morphine induced proliferative retinopathy in sickle cell disease (Gupta et al., personal communication). It is anticipated that treatment with an opioid antagonist may significantly inhibit the retinopathy, particularly with opioid-induced retinopathy in sickle cell patients that are in active opioid therapy, and receive opioids for long periods of time, including chronic therapy for weeks, months or even years.

The methods of the present invention are also envisioned to be of value in reducing the risk of recurrence of a malignancy or neoplasm after treatment with other therapeutic modalities, e.g., after surgical intervention. For example, the present invention provides a method for reducing the risk of recurrence of postoperative cancer. The cancers may include, for example, breast cancer or prostate cancer, and reduced risk may be achieved by providing to the patient suffering from such cancer an effective amount of an opioid antagonist, particularly a peripheral opioid antagonist. For example, as described above, patients undergoing breast cancer surgery had a significant difference (fourfold) in the incidence of recurrence at 2-4 years depending on whether the patients received regional or general anesthesia (with morphine during their initial surgery. Co-administration of the opioid antagonists, especially peripheral antagonist, in accordance with the present invention with surgical treatment may be of value to reduce the incidence of recurrence of the cancer.

It is also contemplated that the invention provides a method of inhibiting the activity of VEGF by providing to the affected cells or subject an effective amount of an opioid antagonist under conditions sufficient to inhibit VEGF-induced angiogenesis. In other words, the compounds of the present invention have VEGF-inhibitory or antagonist activity.

As also shown in the examples below, it has further been found that a peripheral opioid antagonist, MNTX, attenuates not only VEGF-induced endothelial cell migration, but also induction of endothelial migration and/or proliferation by other pro-migration/pro-proliferative factors such as platelet derived growth factor (PDGF), or sphingosine 1-phosphate (S1P). Such attenuation ranges from about 10% to 60%, and provides further evidence that the methods of the present invention have value in inhibiting pro-migration, pro-angiogenic factors.

The methods of the invention also encompass treating patients, e.g., cancer patients, who are undergoing treatment with opioid agonists. Opioid agonists include, but are not limited to, morphine, methadone, codeine, meperidine, fentidine, fentanil, sufentanil, alfentanil and the like. As described above, opioid agonists are classified by their ability to agonize one type of receptor an order of magnitude more effectively than another. For example, the relative affinity of morphine for the mu receptor is 200 times greater than for the kappa receptor, and is therefore classified as a mu opioid agonist. Some opioid agonists may act as agonists towards one receptor and antagonists toward another receptor and are classified as agonist/antagonists, (also known as mixed or partial agonists). "Agonist/antagonist," "partial agonist," and "mixed agonist" are used interchangeably herein. These opioids include, but are not limited to, pentazocine, butorphanol, nalorphine, nalbufine, buprenorphine, bremazocine, and bezocine. Many of the agonist/antagonist group of opioids are agonists at the kappa receptors and antagonists at the mu receptors. Further, it is envisioned the active metabolites of opioid agonists may also be active as angiogenesis inducers. For example, the metabolites of morphine, morphine 3-glucuronide (M3G) and morphine 6-glucuronide (M6G) may be active proangiogenic factors.

Generally, the peripheral opioid antagonists in accordance with the present invention may be administered in an effective amount such that the patient's plasma level of the peripheral opioid antagonist is in the range from $10^{-6}$ M to $10^{-9}$ M. Patient drug plasma levels may be measured using routine HPLC methods known to those of skill in the art.

As described in the examples below, the enkephalin analog DAMGO induces endothelial migration. Thus, the methods of the present invention may be of value to patient suffering from angiogenic-related or hyperproliferative diseases, e.g., cancer, quite apart from treatment with opioid agonists.

The particular mode of administration of the opioid antagonist selected will depend, of course, upon the particular combination of drugs selected, the severity of the tumor progression being treated, in the cancer patient, the general health condition of the patient, and the dosage required for therapeutic efficacy. The methods of this invention, generally speaking, may be practiced using any mode of administration that is medically acceptable, e.g., any mode that produces effective levels of the active compounds without causing clinically unacceptable adverse effects. Such modes of administration include oral, rectal, topical (as by powder, ointment, drops, transdermal patch or iontophoretic devise), trans dermal, sublingual, intramuscular, infusion, intravenous, pulmonary, intramuscular, intracavity, as an aerosol, aural (e.g., via eardrops), intranasal, inhalation, intraocular or subcutaneous. Direct injection could also be used for local delivery. Oral or subcutaneous administration may be suitable for prophylactic or long term treatment because of the convenience of the patient as well as the dosing schedule. For ocular diseases, ophthalmic formulations may be injected or instilled directly.

Additionally, the opioid antagonists may be administered as an enterically coated tablet or capsule. In some embodiments, the opioid antagonist is administered by a slow infusion method or by a time-release or controlled-release method or as a lyophilized powder.

When administered, the compounds of the invention are given in pharmaceutically acceptable amounts and in pharmaceutically acceptable compositions or preparations. Such preparations may routinely contain salts, buffering agents, preservatives, and optionally other therapeutic ingredients. When used in medicine, the salts should be pharmaceutically acceptable, but non-pharmaceutically acceptable salts may conveniently be used to prepare pharmaceutically acceptable salts thereof and are not excluded from the scope of the invention.

Such pharmacologically and pharmaceutically acceptable salts include, but are not limited to, those prepared from the following acids: hydrochloric, hydrobromic, sulfuric, nitric, phosphoric, maleic, acetic, salicylic, p-toluenesulfonic, tartaric, citric, methanesulfonic, formic, succinic, naphthalene-2-sulfonic, pamoic, 3-hydroxy-2-naphthalenecarboxylic, and benzene sulfonic. Suitable buffering agents include, but are not limited to, acetic acid and salts thereof (1-2% WN); citric acid and salts thereof (1-3% WN); boric acid and salts thereof (0.5-2.5% WN); and phosphoric acid and salts thereof (0.8-2% WN).

Suitable preservatives include, but are not limited to, benzalkonium chloride (0.003-0.03% WN); chlorobutanol (0.3-0.9% WIN); parabens (0.01-0.25% WN) and thimerosal (0.004-0.02% WN).

For ease of administration, a pharmaceutical composition of the peripheral opioid antagonist may also contain one or more pharmaceutically acceptable excipients, such as lubricants, diluents, binders, carriers, and disintegrants. Other auxiliary agents may include, e.g., stabilizers, wetting agents, emulsifiers, salts for influencing osmotic pressure, coloring, flavoring and/or aromatic active compounds.

A pharmaceutically acceptable carrier or excipient refers to a non-toxic solid, semi-solid or liquid filler, diluent, encapsulating material or formulation auxiliary of any type. For example, suitable pharmaceutically acceptable carriers, diluents, solvents or vehicles include, but are not limited to, water, salt (buffer) solutions, alcohols, gum arabic, mineral and vegetable oils, benzyl alcohols, polyethylene glycols, gelatin, carbohydrates such as lactose, amylose or starch, magnesium stearate, talc, silicic acid, viscous paraffin, vegetable oils, fatty acid monoglycerides and diglycerides, pentaerythritol fatty acid esters, hydroxy methylcellulose, polyvinyl pyrrolidone, etc. Proper fluidity may be maintained, for example, by the use of coating materials such as lecithin, by the maintenance of the required particle size in the case of dispersions and by the use of surfactants. Prevention of the action of microorganisms may be ensured by the inclusion of various antibacterial and antifungal agents such as paraben, chlorobutanol, phenol, sorbic acid and the like.

If a pharmaceutically acceptable solid carrier is used, the dosage form of the analogs may be tablets, capsules, powders, suppositories, or lozenges. If a liquid carrier is used, soft gelatin capsules, transdermal patches, aerosol sprays, topical cream, syrups or liquid suspensions, emulsions or solutions may be the dosage form.

For parental application, particularly suitable are injectable, sterile solutions, preferably nonaqueous or aqueous solutions, as well as dispersions, suspensions, emulsions, or implants, including suppositories. Ampoules are often convenient unit dosages. Injectable depot form may also be suitable and may be made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled.

Depot injectable formulations are also prepared by entrapping the drug in liposomes or microemulsions which are compatible with body tissues. The injectable formulations may be sterilized, for example, by filtration through a bacterial-retaining filter or by incorporating sterilizing agents in the form of sterile solid compositions which can be dissolved or dispersed in sterile water or other sterile injectable media just prior to use.

For enteral application, particularly suitable are tablets, dragees, liquids, drops, suppositories, or capsules such as soft gelatin capsules. A syrup, elixir, or the like can be used wherein a sweetened vehicle is employed.

As noted, other delivery system may include time-release, delayed-release or sustained-release delivery system. Such system can avoid repeated administrations of the compounds of the invention, increasing convenience to the patient and the physician and maintain sustained plasma levels of compounds. Many types of controlled-release delivery system are available and known to those of ordinary skill in the art. Sustained- or controlled-release compositions can be formulated, e.g., as liposomes or those wherein the active compound is protected with differentially degradable coatings, such as by microencapsulation, multiple coatings, etc.

For example, compounds of this invention may be combined with pharmaceutically acceptable sustained-release matrices, such as biodegradable polymers, to form therapeutic compositions. A sustained-release matrix, as used herein, is a matrix made of materials, usually polymers, which are degradable by enzymatic or acid-base hydrolysis or by dissolution. Once inserted into the body, the matrix is acted upon by enzymes and body fluids. A sustained-release matrix may be desirably chosen from biocompatible materials such as liposomes, polymer-based system such as polylactides (polylactic acid), polyglycolide (polymer of glycolic acid), polylactide co-glycolide (copolymers of lactic acid and glycolic acid), polyanhydrides, poly(ortho) esters, polysaccharides, polyamino acids, hyaluronic acid, collagen, chondroitin sulfate, polynucleotides, polyvinyl propylene, polyvinyl pyrrolidone, and silicone; nonpolymer system such as carboxylic acids, fatty acids, phospholipids, amino acids, lipids such as sterols, hydrogel release system; silastic system; peptide-based system; implants and the like. Specific examples include, but are not limited to: (a) erosional system in which the polysaccharide is contained in a form within a matrix, found in U.S. Pat. Nos. 4,452,775, 4,675,189, and 5,736,152 (herein incorporated by reference in their entireties), and (b) diffusional system in which an active component permeates at a controlled rate from a polymer such as described in U.S. Pat. Nos. 3,854,480, 5,133,974 and 5,407,686 (herein incorporated by reference in their entireties). In addition, pump-based hard-wired delivery system can be used, some of which are adapted for implantation. Suitable enteric coatings are described in PCT publication No. WO 98/25613 and U.S. Pat. No. 6,274,591, both incorporated herein by reference.

Use of a long-term sustained-release implant may be particularly suitable for treatment of chronic conditions. "Long-term" release, as used herein, means that the implant is constructed and arranged to deliver therapeutic levels of the active ingredient for at least 7 days, and suitably 30 to 60 days. Long-term sustained-release implants are well-known to those of ordinary skill in the art and include some of the release system described above.

For topical application, there are employed as nonsprayable form, viscous to semi-solid or solid form comprising a carrier compatible with topical application and having a dynamic viscosity preferably greater than water. Suitable formulations include, but are not limited to, solutions, suspensions, emulsions, cream, ointments, powders, liniments, salves, aerosols, etc., which are, if desired, sterilized or mixed with auxiliary agents, e.g., preservatives, etc.

Transdermal or iontophoretic delivery of pharmaceutical compositions of the peripheral opioid antagonists is also possible.

Respecting MNTX specifically, aqueous formulations may include chelating agent, a buffering agent, an antioxidant and, optionally, an isotonicity agent, preferably pH adjusted to between 3.0 and 3.5. Preferred such formulations that are stable to autoclaving and long term storage are described in application Ser. No. 10/821,811, now published as US 2004/0266806, entitled "Pharmaceutical Formulation," the disclosure of which is incorporated herein by reference.

In one embodiment, compounds of the invention are administered in a dosing regimen which provides a continuous dosing regimen of the compound to a subject, e.g., a regimen that maintains minimum plasma levels of the opioid antagonist, and preferably eliminates the spikes and troughs of a drug level with conventional regimens. Suitably, a continuous dose may be achieved by administering the compound to a subject on a daily basis using any of the delivery methods disclosed herein. In one embodiment, the continuous dose may be achieved using continuous infusion to the subject, or via a mechanism that facilitates the release of the compound over time, for example, a transdermal patch, or a sustained release formulation. Suitably, compounds of the invention are continuously released to the subject in amounts sufficient to maintain a concentration of the compound in the plasma of the subject effective to inhibit or reduce opioid induced angiogenesis; or in cancer patients, to attenuate growth of a tumor. Compounds in accordance with the present invention, whether provided alone or in combination with other therapeutic agents, are provided in an antiangiogenic effective amount. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the level of ordinary skill in the art to start doses of the compound at levels lower than those required to achieve the desired therapeutic effect and to gradually increase the dosage until the desired effect is achieved.

If desired, the effective daily dose may be divided into multiple doses for purposes of administration. Consequently, single dose compositions may contain such amounts or submultiples thereof to make up the daily dose. As noted, those of ordinary skill in the art will readily optimize effective doses and co-administration regimens (as described herein) as determined by good medical practice and the clinical condition of the individual patient.

Generally, oral doses of the opioid antagonists, particularly peripheral antagonists, will range from about 0.01 to about 80 mg/kg body weight per day. It is expected that oral doses in the range from 1 to 20 mg/kg body weight will yield the desired results. Generally, parenteral administration, including intravenous and subcutaneous administration, will range from about 0.001 to 5 mg/kg body weight. It is expected that doses ranging from 0.05 to 0.5 mg/kg body weight will yield the desired results. Dosage may be adjusted appropriately to achieve desired drug levels, local or systemic, depending on the mode of administration. For example, it is expected that the dosage for oral administration of the opioid antagonists in an enteric ally coated formulation would be from 10 to 30% of the non-coated oral dose. In the event that the response in a patient is insufficient of such doses, even higher doses (or effectively higher 30 dosage by a different, more localized delivery route) may be employed to the extent that the patient tolerance permits. Multiple doses per day are contemplated to achieve appropriate systemic levels of compounds. Appropriate system levels can be determined by, for example, measurement of the patient's plasma level of the drug using routine HPLC methods known to these of skill in the art.

In some embodiments of the invention, the opioid antagonists are co-administered with the opioid. The term "co-administration" is meant to refer to a combination therapy by any administration route in which two or more agents are administered to a patient or subject. Co-administration of agents may also be referred to as combination therapy or combination treatment. The agents may be in the same dosage formulations or separate formulations. For combination treatment with more than one active agent, where the active agents are in separate dosage formulations, the active agents can be administered concurrently, or they each can be administered at separately staggered times. The agents may be administered simultaneously or sequentially (e.g., one agent may directly follow administration of the other or the agents may be give episodically, e.g., one can be given at one time followed by the other at a later time, e.g., within a week), as long as they are given in a manner sufficient to allow both agents to achieve effective concentrations in the body. The agents may also be administered by different routes, e.g., one agent may be administered intravenously while a second agent is administered intramuscularly, intravenously or orally. In other words, the co-administration of the opioid antagonist compound in accordance with the present invention with an opioid is suitably considered a combined pharmaceutical preparation which contains an opioid antagonist and a opioid agent, the preparation being adapted for the administration of the peripheral opioid antagonist on a daily or intermittent basis, and the administration of opioid agent on a daily or intermittent basis. Thus, the opioid antagonists may be administered prior to, concomitant with, or after administration of the opioids.

Co-administrable agents also may be formulated as an admixture, as, for example, in a single formulation or single tablet. These formulations may be parenteral or oral, such as the formulations described, e.g., in U.S. Pat. Nos. 6,277,384; 6,261,599; 5,958,452 and PCT publication No. WO 98/25613, each hereby incorporated by reference.

It is further contemplated that the present method can be used alone or in conjunction with other treatments to control the growth or migration of endothelial cells in connection with the various conditions described above. The peripheral opioid antagonist may be co-administered with another therapeutic agent that is not an opioid or opioid antagonist. Suitable such therapeutic agents include anticancer agents, e.g., chemotherapeutic agents, radiotherapy, or other antiangiogenic agents such as suramin, or anti-VEGF mab, an endostatin or radiotherapy. It is envisioned that the opioid antagonists in accordance with the present invention are of particular value when co-administered with those agents that inhibit VEGF activity, e.g., anti-VEGF mab. The anti-VEGF antibodies are useful in the treatment of various neoplastic and non-neoplastic diseases and disorders, including endometrial hyperplasia, endometriosis, abnormal vascular proliferation associated with phakomatoses, edema (such as that associated with brain tumors and Meigs' syndrome. One example of an anti-VEGF mab is bevacizumab (Avastin, Genentech) described in U.S. Pat. No. 6,884,879 and WO94/10202 hereby incorporated in their entirety. In a certain embodiments of the invention, MNTX is co-administered with Avastin.

In other words, the compounds of the present invention may also be useful for the treatment of cancer in patients, as described above, either when used alone or in combination with one or more other anticancer agents, e.g., radiotherapy and/or other chemotherapeutic, including antiangiogenic, treatments conventionally administered to patients for treating cancer. The main categories and examples of such drugs are listed herein and include, but are not limited to metalloprotease inhibitors, inhibitors of endothelial cell proliferation/migration, antagonists of angiogenic growth factors, inhibitors of Integrin/Survival signaling, and chelators of copper.

In certain embodiments the compounds of the invention can be combined with known combinations of anticancer agents. The compounds of the invention can be combined with an antiangiogenic agent and a chemotherapeutic agent and administered to a cancer patient. For example, MNTX can be administered to cancer patients in combination with Avastin and 5-fluorouracil. It is anticipated that the opioid antagonists co-administered with various anticancer drugs, radiotherapy or other anti angiogenic drugs can give rise to a significantly enhanced antiproliferative effect on cancerous cells, and thus providing an increased therapeutic effect, e.g., employing peripheral opioid antagonists to certain tumors can potentiate their response to other therapeutic regimens. Specifically, a significantly increased anti angiogenic or antihyperproliferative effect is obtained with the above disclosed co-administered combinations, even if utilizing lower concentrations of the anticancer, a lower dosing of radiation, or other antiangiogenic drugs compared to the treatment regimes in which the drugs or radiation are used alone. Therefore there is the potential to provide therapy wherein adverse side effects associated with the anticancer or other antiangiogenic drugs or radiotherapy are considerably reduced than normally observed with the anticancer or other antiangiogenic drugs or radiotherapy used alone in larger doses. For example, co-administration of an opioid antagonist in accordance with the present invention with an anti-VEGF agent, e.g., anti-VEGF mab, may reduce the dose of the anti-VEGF agent or increase potency or efficacy or both. Further, as detailed herein, the co-administration of an opioid antagonist in accordance with the present invention with other anticancer modalities may have prophylactic value.

When used in the treatment of hyperproliferative diseases, compounds of the present invention may be co-administered with metalloprotease inhibitors such as for example: Marimastat, synthetic matrix metalloprotease inhibitor (MMPI), British Biotech; Bay 12-9566, synthetic MMPI and inhibitor tumor growth, Bayer; AG3340, synthetic MMPI, Agouron/Warner-Lambert; CGS 27023A, synthetic MMPI, Novartis; CGS 27023A, Synthetic MMPI; COL-3, synthetic MMPI, tetracycline derivative, Collagenex; AE-941 (Neovastat), naturally occurring MMPI, AEterna, BMS-275291, synthetic MMPI, Bristol-Myers Squibb; Penicillamine, urokinase inhibitor, NCI-NABTT.

When used in the treatment of hyperproliferative diseases, compounds of the present invention may be co-administered with direct inhibitors of endothelial cell proliferation/migration such as: TNP-470 (fumagillin derivative), inhibits endothelial cell growth, TAP Pharmaceuticals; Squalamine, inhibits sodium-hydrogen exchanger, NIHE3, Magainin; Combretastatin, induction of apoptosis in proliferating endothelial cells, Oxigene; Endostatin, inhibition of endothelial cells, EntreMed; Penicillamine, blocks endothelial cell migration and proliferation, NCI-NABTT; Farnesyl Transferase Inhibitor (FTI), blocks endothelial cell migration and proliferation, NCI-NABTT, -L-778,123 Merck, -SCH66336 Schering-Plough, -RI15777 Janssen.

When used in the treatment of hyperproliferative diseases, compounds of the present invention may be co-administered with antagonists of angiogenic growth factors such as: anti-VEGF antibody, monoclonal antibody that inactivates VEGF, Genentech; thalidomide, blocks activity of angiogenic growth factors (bFGF, VEGF, TNF-alpha), Celgene; SU5416 (sexaminib; 3[(3,5-dimethyl-1H-pyrrol-2-yl)methylene]-1,3-dihydro-2H-indol-2-one), blocks VEGF receptor (Flk-1/KDR) signaling (tyrosine kinase), Sugen-NCI; ribozyme (Angiozyme), attenuates mRNA of VEGF receptors, Ribozyme Pharmaceuticals, Inc; SU6668 (5-[1,2-dihydro-2-oxo-3H-indol-3-ylidene)methyl]-2,4-dimethyl-1H-pyrrole-3-propanoic acid), blocks VEGF, bFGF, and PDGF receptor signaling, Sugen; PTK787/ZK22584 (vatalnib), blocks VEGF receptor signaling, Novartis; Interferon-alpha, inhibition of bFGF and VEGF production; Suramin, blocks binding of growth factor to its receptor, NCI-NABTT.

When used in the treatment of hyperproliferative diseases, compounds of the present invention may be co-administered with drugs that inhibit endothelial-specific Integrin/Survival signaling: Vitaxin, antibody to alpha-v-beta3 integrin present on endothelial cell surface, Ixsys; EMD121974, small molecule blocker of integrin present on endothelial cell surface, Merck KGaA.

When used in the treatment of hyperproliferative diseases, compounds of the present invention may be co-administered with chelators of copper, such as: penicillamine, sulfhydryl group binds copper; clears copper through urinary excretion, NCI-NABTT; tetrathiomolybdate, thiol groups tightly bind copper, inactivate copper available to tumor, University of Michigan Cancer Center; captopril, chelates copper and zinc; also, inhibitor of MMP and angiotensin converting enzyme, Northwestern University.

When used in the treatment of hyperproliferative diseases, compounds of the present invention may be co-administered with angiogenesis antagonists with distinct mechanisms:

CAI (carboxyamidotriazole), inhibitor of calcium influx, NCI; ABT-627 (atrasentan), endothelin receptor antagonist, Abbott/NCI; CM101/ZDO101, group B streptococcus toxin that selectively disrupts proliferating endothelium by interaction with the (CM201) receptor, CarboMed/Zeneca; Interleukin-12, induction of interferon-gamma, down-regulation of IL-10, induction of IP-10, M.D. Anderson Cancer Center/Temple University, Temple University, Genetics Institute, Hoffman LaRoche; IM862 (small anti-VEGF dipeptide; L-glu-L-trp), blocks production of VEGF and bFGF; increases production of the inhibitor IL-12, Cytran; PNU-145156E (7,7-(carbony-bis-[imino-N-methyl-4,2-pyrrole-carbonylimino[N-methyl-4,2-pyrrole]-carbonylimino)-bis (1,30-naphthaline disulfonate), blocks angiogenesis induced by Tat protein, Pharmacia and Upjohn.

When used in the treatment of hyperproliferative diseases, compounds of the present invention may be co-administered with chemotherapeutic agents such as, for example, alpha interferon, COMP (cyclophosphamide, vincristine, methotrexate and prednisone), etoposide, mBACOD (methortrexate, bleomycin, doxorubicin, cyclophosphamide, vincristine and dexamethasone), PRO-MACE/MOPP (prednisone, methotrexate (w/leucovin rescue), doxorubicin; cyclophosphamide, paclitaxol, docetaxol, etoposide/mechlorethamine, vincristine, prednisone and procarbazine), vincristine, vinblastine, angioinhibins, TNP-470, pentosan polysulfate, platelet factor 4, angiostatin, LM-609, SU-101, CM-101, Techgalan, thalidomide, SP-PG and the like.

Anticancer agents which may be co-administered with compounds of the present invention also suitably include antimetabolites (e.g., 5-fluoro-uracil, methotrexate, fludarabine), antimicrotubule agents (e.g., vincristine, vinblastine, taxanes such as paclitaxel, docetaxel), an alkylating agent (e.g., cyclophosphamide, melphalan, biochoroethylnitrosurea, hydroxyurea), nitrogen mustards, (e.g., mechloethamine, melphan, chlorambucil, cyclophosphamide and Ifosfamide); nitrosoureas (e.g., carmustine, lomustine, semustine and streptozocin;), platinum agents (e.g., cisplatin, carboplatin, oxaliplatin, JM-216, C 1-973), anthracyclines (e.g., doxrubicin, daunorubicin), antibiotics (e.g., mitomycin, idarubicin, adriamycin, daunomycin), topoisomerase inhibitors (e.g., etoposide, camptothecins), alkyl sulfonates including busulfan; triazines (e.g., dacarbazine); ethyenimines (e.g., thiotepa and hexamethylmelamine); folic acid analogs (e.g., methotrexate); pyrimidine analogues (e.g., 5 fluorouracil, cytosine arabinoside); purine analogs (e.g., 6-mercaptopurine, 6-thioguanine); antitumor antibiotics (e.g., actinomycin D; bleomycin, mitomycin C and methramycin); hormones and hormone antagonists (e.g., tamoxifen, cortiosteroids) and any other cytotoxic agents, (e.g., estramustine phosphate, prednimustine).

In addition to the co-administration of anti-VEGF agent with the compounds in accordance with the present invention, other chemotherapeutics, such as anti-microtubules, antimetabolites, and other tyrosine kinase inhibitors, may be combined with the compounds of the present invention. Tyrosine kinases are an especially important target because they play an important role in the modulation of growth factor signaling. Tyrosine kinase inhibitors compete with the ATP binding site of the catalytic domain of several oncogenic tyrosine kinases. Several tyrosine kinase inhibitors have been found to have effective antitumor activity; these include imatinib mesylate (STI571; Gleevec), gefitinib (Iressa), erlotinib (OSI-1774; Tarceva), lapatinib (GW-572016), canertinib (CI-1033), semaxinib (SU5416), vatalanib (PTK787/ZK222584), sorafenib (BAY 43-9006), sutent (SU11248), and leflunomide (SU101).

Figure 29:
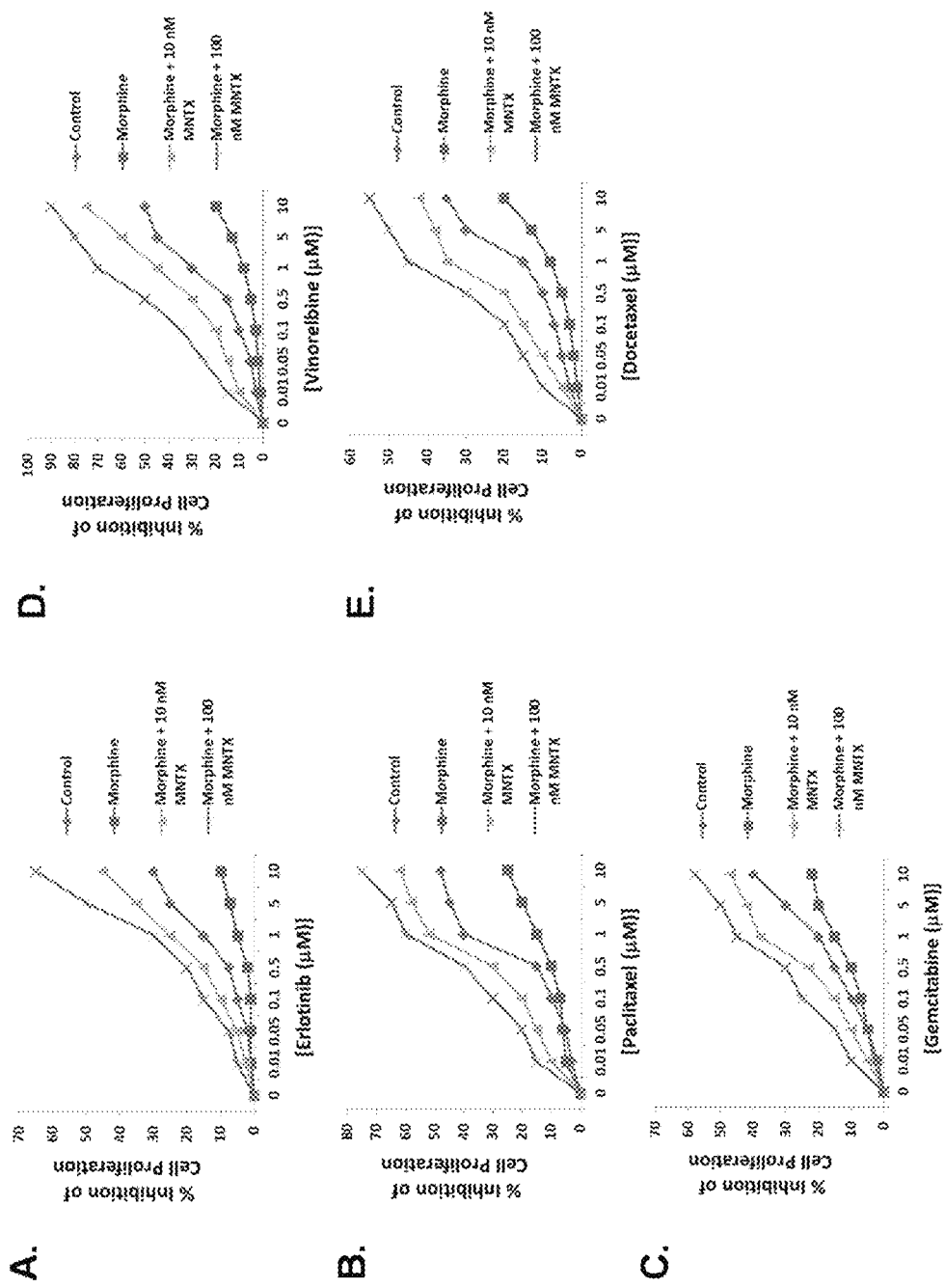
FIG. 29 is a graph of percent inhibition of NSCLC cells in the presence of (A) erlotinib, (B) paclitaxel, (C) gemcitabine, (D) vironrelbine, and (E) docetaxel with morphine and combinations of morphine and MNTX.

As demonstrated in the Examples below, methylnaltrexone enhances the ability of erlotinib (an EGF receptor inhibitor), gemcitabine (an antimetabolite), vironrelbine (an anti-microtubule), paclitaxel (an anti-microtubule), and docetaxel (an anti-microtubule) to inhibit NSCLC cell proliferation. Morphine on the other hand, leads to relative chemotherapeutic resistance (e.g., see FIG. 29). Thus, an opioid antagonist can enhance the efficacy of a chemotherapeutic agent.

It will be understood that agents which can be combined with the compounds of the present invention for the inhibition, treatment or prophylaxis of angiogenesis and/or cancers are not limited to those listed above, but include, in principle, any agents useful for the treatment opioid induced angiogenic diseases and tumor growth.

The present invention is further explained by the following examples, which should not be construed by way of limiting the scope of the present invention.

EXAMPLES

Example 1

Endothelial Cell Migration Assay

The antiangiogenic activity of the peripheral opioid antagonists in accordance with the present invention was evaluated in experiments testing the ability of the antagonist to inhibit or modulation capillary endothelial cell migration using a modified Boyden chamber.

The endothelial cell migration assay was performed as described by Lingen, M. W., Methods in Molecular Medicine, 78: 337-347 (2003), the disclosure of which is incorporated by reference. Briefly, Human Microvascular Endothelial Cells (HMVEC) (Cell Systems, Kirkland, W.A.) were starved overnight in Endothelial Growth Medium (EGM) containing 0.1% bovine serum albumin (BSA). Cells were then trypsinized and resuspended in Dulbecco's Modified Eagle Medium (DME) with 0.1% BSA at a concentration of $1\times10^6$ cells/mL. Cells were added to the bottom of a 48-well modified Boyden chamber (NeuroPore Corporation, Pleasanton, Calif.). The chamber was assembled and inverted, and cells were allowed to attach for 2 hours at 37° C. to polycarbonate chemotaxis membranes (5 µm pore size) (NeuroProbe) that had been soaked in 0.1% gelatin overnight and dried. The chamber was then reinverted and the compound to be tested at varying concentrations in quadruple, vascular endothelial growth factor (VEGF) (as a positive control) or vehicle were added to the wells of the upper chamber (to a total volume of 50 mL); the apparatus was then incubated for 4 hours at 37° C. Membranes were recovered, fixed and stained (DiffQuick, Fisher Scientific, Pittsburgh, Pa.) and the number of cells that had migrated to the upper chamber per 10 high power fields were counted. Background migration to DME+O.I % BSA was subtracted and the data reported as the number of cells migrated per 10 high power fields (400 times). Each substance was tested in quadruplicate in each experiment, and all experiments were repeated to least twice. VEGF (R&D System, Minneapolis, Minn.) was used as a positive control at a concentration of 200 pg/mL. The optimal concentration for VEGF was determined previously by dose-response experiments (data not shown). The compounds tested as described above were morphine, naloxone, methylnaltrexone, and the combination of methylnaltrexone and morphine. The concentrations of each tested substance ranged for 0.001 to 10.0 µM. The concentration of the morphine was constant at 0.1 µM. The results are shown in FIG. 1.

FIG. 1 shows that morphine increased migration in a concentration-dependent manner. The co-addition of methylnaltrexone and morphine, however, decreased migration in a concentration-dependent manner. Neither methylnaltrexone or naloxone alone affected migration.

Example 2

Endothelial Cell Migration Assay

Another set of experiments was conducted in accordance with the procedure described in Example 1. In this set of experiments, methylnaltrexone and the combination of methylnaltrexone and morphine was again tested for ability to inhibit endothelial cell migration. The methylnaltrexone concentrations when tested alone varied from 0.001 to 10.0 µM. In combination, the concentrations of methylnaltrexone varied from 0.001 to 10.0 µM, while the morphine concentration remained constant at 0.1 µM as described in Example 1. The results are shown in FIG. 2.

FIG. 2 shows the combination of methylnaltrexone and morphine decreased migration in a concentration-dependent manner, while methylnaltrexone alone did not affect migration.

Example 3

Endothelial Cell Migration Induced by DAMGO

The drugs used in this study were [D-Ala 2, N-McPhe4, Gly5-ol]enkephalin or DAMGO (Sigma, St. Louis, Mo.); naloxone (Sigma, St. Louis, Mo.); N-methylnaltrexone bromide or methylnaltrexone (Mallinckrodt Specialty Chemicals, Phillipsburg, N.J.). The endothelial cell migration assay was performed as previously described (9). Human dermal microvascular endothelial cells (Cell Systems, Kirkland, WA) were starved overnight in media containing 0.1% bovine serum albumin (BSA), harvested, resuspended into Dulbecco's Modified Eagle's media (DME) with 0.1% BSA, and plated on a semi-porous gelatinized membrane in a modified Boyden chamber (Nucleopore Corporation, Pleasanton, Calif.). Test substances were then added to the wells of the upper chamber and cells were allowed to migrate for four hours at 37° C.

Membranes were recovered, fixed, and stained and the number of cells that had migrated to the upper chamber per ten high power fields counted by a blinded observer. Background migration to DME+0.1% BSA was subtracted and the data reported as the number of cells migrated per 10 high power fields (400×). Each substance was tested in quadruplicate in each experiment and all experiments were repeated at least twice. The concentration of DAM GO was 1 µM, VEGF (R&D Systems, Minneapolis, Minn.) was used as a positive control at a concentration of 200 pg/mL. The optimal concentration for VEGF was determined previously by dose-response experiments (data not shown).

Figure 4:
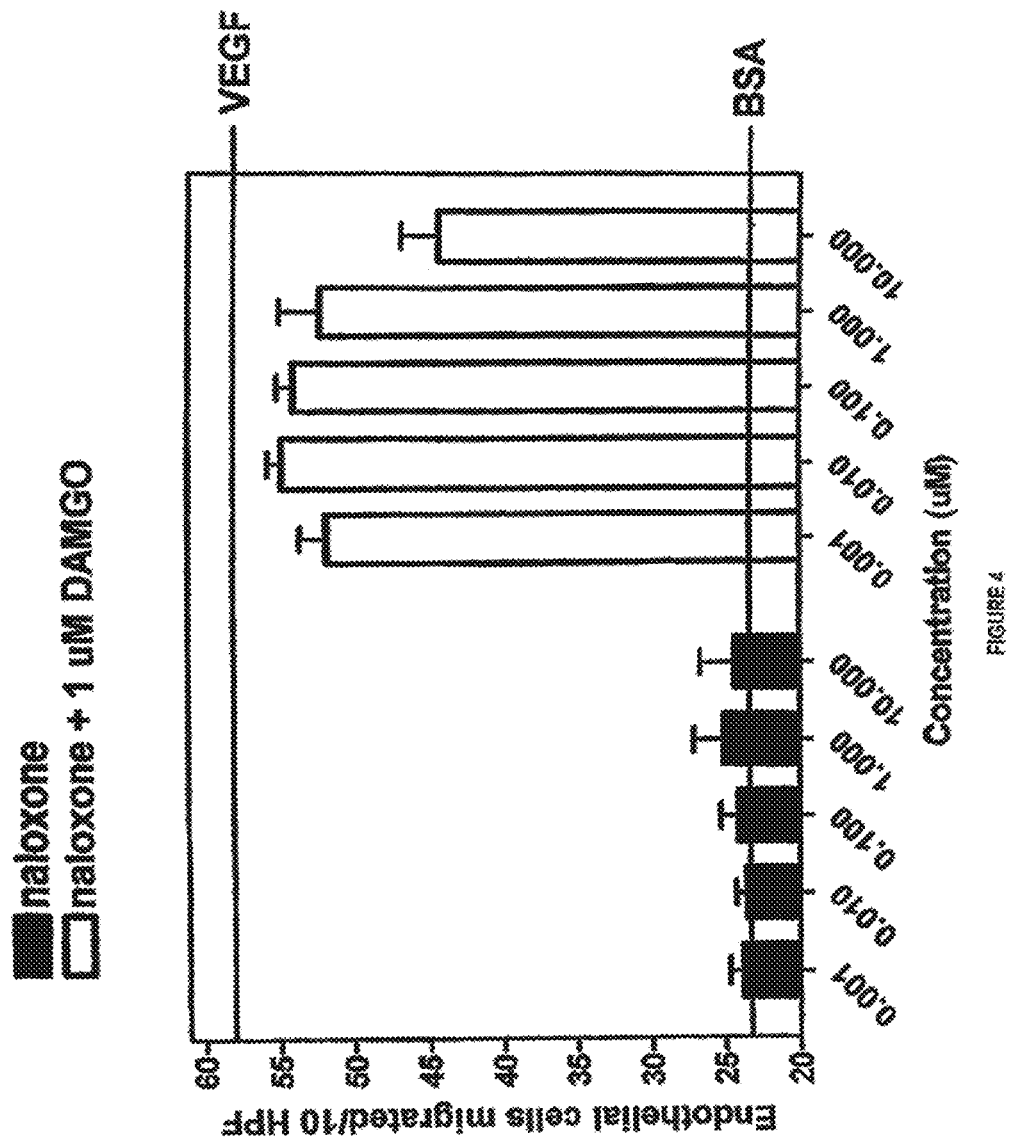
FIG. 4 is a bar graph of dose-dependent inhibition of HMVEC migration 15 using naloxone and naloxone+ DAMGO.
Figure 5:
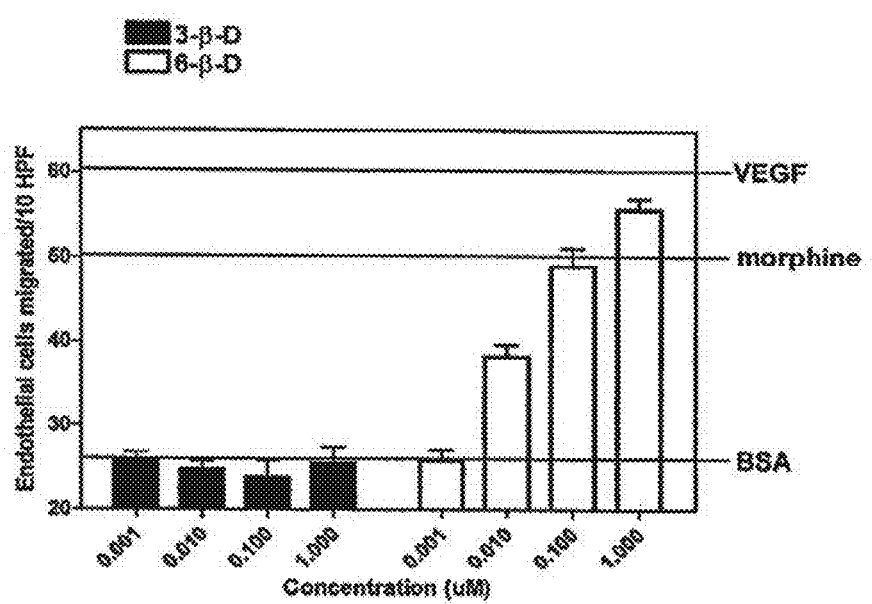
FIG. 5 is a bar graph of dose-dependent effect of M3G and M6G on HMVEC migration.

The results are shown in FIG. 3 which shows that methylnaltrexone and DAMGO decreased migration in a concentration-dependent manner. FIG. 4 illustrates similar results with naloxone and DAMGO. The inactive morphine metabolite M3G exerts no angiogenic activity while M6G known to act at the mu receptor exhibited a concentration dependent effect on angiogenesis (FIG. 5).

Example 4

Treatment of Human and Mammalian Subjects with Methylnaltrexone

In a first set of experiments, mice are induced to develop tumors by transformation, inbreeding or transplantation of tumor cells. Thirty-six mice, each bearing tumors having a volume of at least 60 mm3, are randomly divided into three groups. The first group receives a control substance comprising neither an opioid nor an opioid antagonist. The second group receives an opioid, e.g. morphine administered orally at a dose of 0.5 mg/kg/day. The third group receives an opioid, e.g. morphine administered orally at a dose of 0.5 mg/kg/day, and the peripheral opioid antagonist methylnaltrexone, administered orally at a dose of 5 mg/kg/day.

The compounds are administered daily for a period of eight weeks. Differences in the rate of tumor growth, tumor size, a reduction in angiogenesis in the tumor and mortality of the mice between each of the groups are recorded. The results demonstrate a reduction in tumor growth and angiogenesis compared to controls or morphine alone.

In a second set of experiments, human cancer patients are enrolled in a study. Enrollees in the study are controlled for age, stage of disease, treatment types and genetic and familial factors. Participants are divided into two groups according to whether they are receiving opioids, e.g. morphine. The group receiving opioids is further randomly divided into two subgroups. One of the two subgroups receiving opioids receives a peripheral opioid antagonist, e.g., methylnaltrexone administered orally at a dose of 5 mg/kg/day for a period of eight weeks. The other of the two subgroups receives placebo for the same period. Differences in the rate of tumor growth, tumor size, a reduction in angiogenesis in the tumor and mortality of the participants in each of the groups are recorded.

Example 5

Treatment of Human and Mammalian Subjects with Alvimopan

Mice that have been induced to develop tumors are subjected to the protocol as described in Example 3, except that the peripheral opioid antagonist is alvimopan. The results demonstrate a reduction in tumor growth and angiogenesis compared to controls or opioid alone.

Human cancer patients are enrolled in a study conducted as described in Example 4, except that the peripheral opioid antagonist is alvimopan.

Example 6

Therapies Comprising Co-Administration of the Peripheral Opioid Antagonist Methyl Naltrexone and Second Therapeutic Agent In a first set of experiments, mice are induced to develop tumors by transformation, inbreeding or transplantation of tumor cells. Forty-eight mice, each bearing tumors having a volume of at least 60 mm$^3$, are randomly divided into six groups. The first group receives a control substance which does not comprise an opioid, an opioid antagonist, or an anticancer agent. The second group receives an opioid, e.g. morphine administered orally at a dose of 0.5 mg/kg/day. The third group receives an opioid, e.g. morphine administered orally at a dose of 0.5 mg/kg/day, and the peripheral opioid antagonist methylnaltrexone, administered orally at a dose of 5 mg/kg/day. The fourth group receives an opioid, e.g. morphine administered orally at a dose of 0.5 mg/kg/day, and the peripheral opioid antagonist methylnaltrexone administered orally at a dose of 5 mg/kg/day with an anticancer therapeutic agent, e.g. bevacizumab (Avastin) at a dose of 5 mg/kg every 14 days. The sixth group receives an opioid, e.g. morphine, at a dose of 0.5 mg/kg/day and an anticancer therapeutic agent, e.g. bevacizumab (Avastin) at a dose of 5 mg/kg every 14 days.

The compounds are administered daily for a period of eight weeks. Differences in the rate of tumor growth, tumor size, a reduction in angiogenesis in the tumor and mortality of the mice in each of the groups are recorded. The results demonstrate an enhanced result (e.g., reduction in angiogenesis and tumor growth) for the groups administered the combination of opioid, opioid antagonist, and anticancer agent compared to the other groups.

In a second set of experiments, human cancer patients receiving an opioid, e.g. morphine, an anticancer therapeutic agent, e.g. bevacizumab (Avastin) or both are enrolled in a study. Enrollees in the study are controlled for age, stage and type of disease, treatment types and genetic and familial factors. Participants receiving an opioid are randomly divided into first and second groups; participants receiving an anticancer therapeutic agent, e.g. bevacizumab (Avastin) are randomly divided into third and fourth groups; participants receiving an opioid plus an anticancer agent, e.g. bevacizumab (Avastin) are randomly divided into fifth and sixth groups. The first, third and fifth groups each receive a peripheral opioid antagonist, e.g., methylnaltrexone administered orally at a dose of 5 mg/kg/day for a period of eight weeks. The second, fourth and sixth groups receive placebo for the same period. Differences in the rate of tumor growth, tumor size, a reduction in angiogenesis in the tumor and mortality of the participants in each of the groups are recorded. The results demonstrate an enhanced result (e.g., reduction in angiogenesis and tumor growth) for the groups administered the combination of opioid, opioid antagonist, and anticancer agent compared to the other groups.

Example 7

Therapies Comprising Co-Administration of the Peripheral Opioid Antagonist Alvimopan and Second Therapeutic Agent Mice that have been induced to develop tumors are subjected to the protocol as described in Example 5, except that the peripheral opioid antagonist is alvimopan. The results demonstrate an enhanced result (e.g., reduction in angiogenesis and tumor growth) for the groups administered the combination of opioid, opioid antagonist, and anticancer agent compared to the other groups.

Human cancer patients are enrolled in a study conducted as described in Example 6, except that the peripheral opioid antagonist is alvimopan. The results demonstrate an enhanced result (e.g., reduction in angiogenesis and tumor growth) for the groups administered the combination of opioid, opioid antagonist, and anticancer agent compared to the other groups.

Example 8

Effect of Opioid Antagonists on Endothelial Cell Migration/Proliferation

Cell culture and reagents-Human dermal microvascular endothelial cells (Cell Systems, Kirkland, WA) and human pulmonary microvascular endothelial cells (Clonetics, Walkersville, Md.) were cultured as previously described in EBM-2 complete medium (Clonetics) at 37° C. in a humidified atmosphere of 5% $CO_2$, 95% air, with passages 6-10 used for experimentation (Garcia et al. 2001). Unless otherwise specified, reagents were obtained from Sigma (St. Louis, Mo.). Reagents for SDS-PAGE electrophoresis were purchased from Bio-Rad (Richmond, Calif.), Immobilon-P transfer membrane from Millipore (Millipore Corp., Bedford, Mass.). The drugs used in this study were [D-Ala$^2$, N-MePhe$^4$, Gly$^5$-ol]enkephalin or DAMGO (Sigma, St. Louis, Mo.); naloxone, morphine-3-glucuronide (M3G) and morphine-6-glucuronide (M6G) (Sigma, St. Louis, Mo.); N-methylnaltrexone bromide or methylnaltrexone (Mallinckrodt Specialty Chemicals, Phillipsburg, N.J.), morphine (Baxter, Deerfield, Ill.). VEGF Receptor Tyrosine Kinase Inhibitor was purchased from Calbiochem (San Diego, Calif.). Mouse anti-RhoA antibody, mouse anti-phosphotyrosine antibody and rho binding domain (RBD)-conjugated beads were purchased from Upstate Biotechnology (Lake Placid, N.Y.). Rabbit anti-VEGF receptor 1 (Flt-I) and anti¬VEGF receptor 2 (Flk-I) antibodies were purchased from Santa Cruz Biotechnology (Santa Cruz, Calif.). Mouse anti-~-actin antibody was purchased from Sigma (St. Louis, Mo.). Secondary horseradish peroxidase (HRP)-labeled antibodies were purchased from Amersham Biosciences (Piscataway, N.J.).

Immunoprecipitation and immunoblotting—Cellular materials were incubated with IP buffer (50 mM HEPES (pH 7.5), 150 mM NaCl, 20 mM MgCl2, 1% TritonX-100, 0.1% SDS, 0.4 mM Na3V04, 40 mM NaF, 50/IM okadaic acid, 0.2 mM phenylmethylsulfonyl fluoride, 1:250 dilution of Calbiochem protease inhibitor mixture 3). The samples were then immunoprecipitated with anti-VEGF receptor 1 or anti-VEGF receptor 2 IgG followed by SDS-PAGE in 4-15% polyacrylamide gels, transfer onto Immobilon™ membranes, and developed with specific primary and secondary antibodies. Visualization of immunoreactive bands was achieved using enhanced chemiluminescence (Amersham Biosciences).

Determination of tyrosine phosphorylation of VEGF Receptors 1 and 2-Solubilized proteins in IP buffer (see above) were immunoprecipitated with either rabbit anti-VEGF receptor 1 or rabbit anti-VEGF receptor 2 antibody followed by SDS-PAGE in 4-15% polyacrylamide gels and transfer onto Immobilon™ membranes (Millipore Corp., Bedford, Mass.). After blocking nonspecific sites with 5% bovine serum albumin, the blots were incubated with either rabbit anti-VEGF receptor 1 antibody, rabbit anti-VEGF receptor 2 antibody or mouse anti-phosphotyrosine antibody followed by incubation with horseradish peroxidase (HRP)-labeled goat anti-rabbit or goat anti-mouse IgG. Visualization of immunoreactive bands was achieved using enhanced chemiluminescence (Amersham Biosciences).

Construction and transfection of siRNA against RhoA—The siRNA sequence targeting human against RhoA was generated using mRNA sequences from Genbank™ (gi: 33876092). For each mRNA (or scramble), two targets were identified. Specifically, RhoA target sequence 1 (5'-AAGAAACTGGTGATTGTTGGT-3') (SEQ ID NO:I), RhoA target sequence 2 (5'-AAAGACATGCTTGCT-CATAGT-3') (SEQ ID NO:2), scrambled sequence I (5'-AAGAGAAA TCGAAACCGAAAA-3') (SEQ ID NO:3), and scramble sequence 2 (5'-AAGAACCCAATTAAGCG-CAAG-3') (SEQ ID NO:4), were utilized. Sense and antisense oligonucleotides were purchased from Integrated DNA Technologies (Coralville, Iowa). For construction of the siRNA, a transcription-based kit from Ambion was used (Silencer™ siRNA construction kit). Human lung microvascular EC were then transfected with siRNA using siPORTamine™ as the transfection reagent (Ambion, Tex.) according to the protocol provided by Ambion. Cells (~40% confluent) were serum-starved for 1 hour followed by incubated with 3 µM (1.5 µM of each siRNA) of target siRNA (or scramble siRNA or no siRNA) for 6 hours in serum-free media. The serum-containing media was then added (1% serum final concentration) for 42 h before biochemical experiments and/or functional assays were conducted.

RhoA activation assay—After agonist and/or inhibitor treatment, EC are solubilized in solubilization buffer and incubated with rho bonding domain (RBD)-conjugated beads for 30 minutes at 4° C. The supernatant is removed and the RBD-beads with the GTP-bound form of Rho A bound are washed extensively. The RBD beads are boiled in SDS-P AGE sample buffer and the bound RhoA material is run on SDS-P AGE, transferred to Immobilon™ and immunoblotted with anti-RhoA antibody (Garcia et al 2001).

Human dermal microvascular EC migration assay—The endothelial cell migration assay was performed as previously described (Lingen 2002). Human dermal microvascular endothelial cells (Cell Systems, Kirkland, W A) were starved overnight in media containing 0.1% bovine serum albumin (BSA), harvested, resuspended into Dulbecco's Modified Eagle's media (DME) with 0.1% BSA, and plated on a semi-porous gelatinized membrane in a modified Boyden chamber (Nucleopore Corporation, Pleasanton, Calif.). Test substances were then added to the wells of the upper chamber, and cells were allowed to migrate for 4 hr at 37° C. Membranes were recovered, fixed, and stained and the number of cells that had migrated to the upper chamber per 10 high-power fields was counted by a blinded observer. Background migration to DME+0.1% BSA was subtracted, and the data were reported as the number of cells migrated per 10 high-power fields (400×). Each substance was tested in quadruplicate in each experiment and all experiments were repeated at least twice. Vascular endothelial growth factor (VEGF, R&D Systems, Minneapolis, Minn.) was used as a positive control at a concentration of 200 pg/mL. The optimal concentration for VEGF was determined previously by dose-response experiments (data not shown).

Human pulmonary microvascular EC migration assay—Twenty-four TranswelfM units with 8 M pore size were used for monitoring in vitro cell migration. HPMVEC ($\sim 1 \times 10^4$ cells/well) were plated with various treatments 30 (100 nM MNTX, 10 µM VEGF Receptor Tyrosine Kinase Inhibitor or siRNA) to the upper chamber and various agonists were added to the lower chamber (100 nM MS, DAMGO or VEGF). Cells were allowed to migrate for 18 hours. Cells from the upper and lower chamber were quantitated using the CellTiter96™ MTS assay (Promega, San Luis Obispo, Calif.) and read at 492 nm. % migration was defined as the # of cells in the lower chamber % the number of cells in both the upper and lower chamber. Each assay was set up in triplicate, repeated at least five times and analyzed statistically by Student's t test (with statistical significance set at $P<0.05$).

Human pulmonary microvascular EC proliferation assay—For measuring cell growth, HPMVEC [$5 \times 10^3$ cells/well pretreated with various agents (100 nM MNTX, 10 µM VEGF Receptor Tyrosine Kinase Inhibitor or siRNA) were incubated with 0.2 mL of serum-free media containing various agonists (100 nM MS, DAMGO or VEGF) for 24 h at 37° C. in 5% C02/95% air in 96-well culture plates. The in vitro cell proliferation assay was analyzed by measuring increases in cell number using the CellTiter96™ MTS assay (Promega, San Luis Obispo, Calif.) and read at 492 nm. Each assay was set up in triplicate, repeated at least five times and analyzed statistically by Student's t test (with statistical significance set at $P<0.05$).

Figure 6:
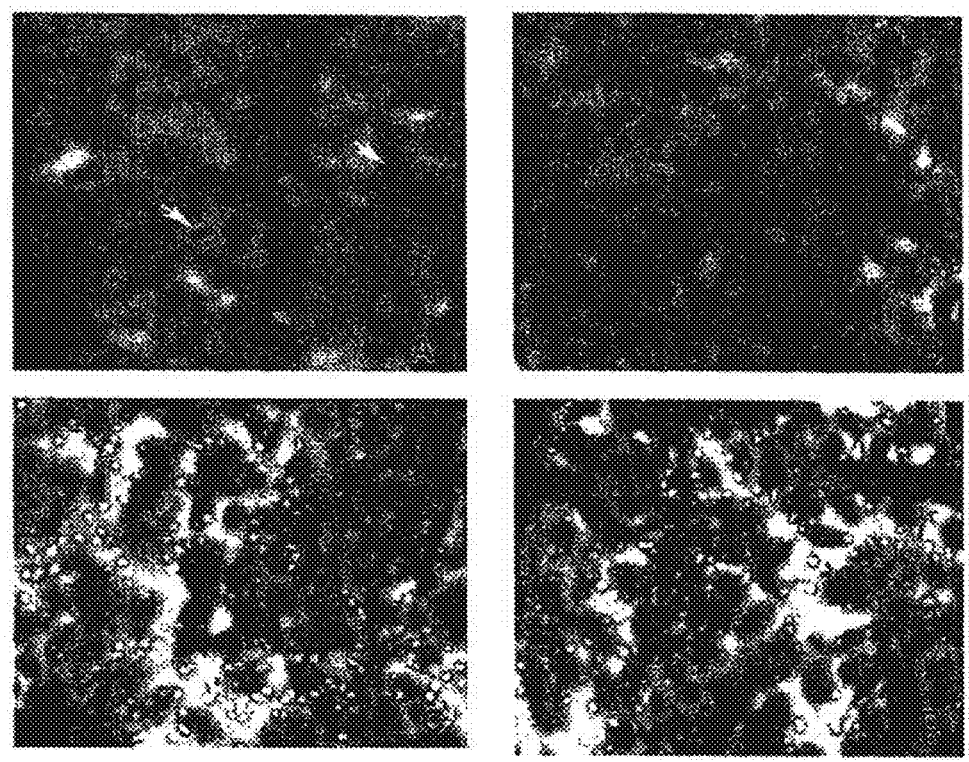
FIG. 6 is a photomicrograph that shows morphine induced endothelial cell migration in the presence and absence of MNTX. Panel A=Control, Panel B=20 MS (morphine sulfate), Panel C=MNTX, and Panel D=MS+MNTX. Arrows are shown in Panel A to highlight several cells that have successfully migrated across the membrane.

Using the endothelial cell migration assay, it was found that MS caused a concentration-dependent increase in endothelial migration. Naloxone and MNTX alone had no effect on endothelial cell migration over a wide range of concentrations. This is demonstrated in representative photomicrographs and quantitatively (FIGS. 6 and 1, respectively). At clinically relevant concentrations of morphine, the magnitude of the effect was approximately 70% of that achieved by VEGF. Endothelial cell migration induced by morphine in concentrations as low as $10^{-7}$M (FIG. 2). Morphine-based endothelial cell migration was attenuated by the mu opioid antagonists naloxone and MNTX (in doses as low as $10^{-8}$ µM) in a concentration-dependent fasmon, strongly suggesting that endothelial cell migration is mediated by morphine's action on the mu opioid receptor (MOR). That the effect is via the MOR rather than other opioid receptors was confirmed by our observations that the highly selective synthetic enkephalin mu agonist DAMGO also induced migration in a concentration dependent fashion. The effect of DAMGO was also blocked by MNTX (FIG. 3). That the inactive morphine metabolite M6G exerts no angiogenic activity, while M6G, known to act at the mu receptor, exhibits a concentration-dependent effect on angiogenesis, confirms our hypothesis that morphine's effect on the endothelium is mediated by mu receptors (McQuay et al. 1997) (FIG. 5).

Figure 7:
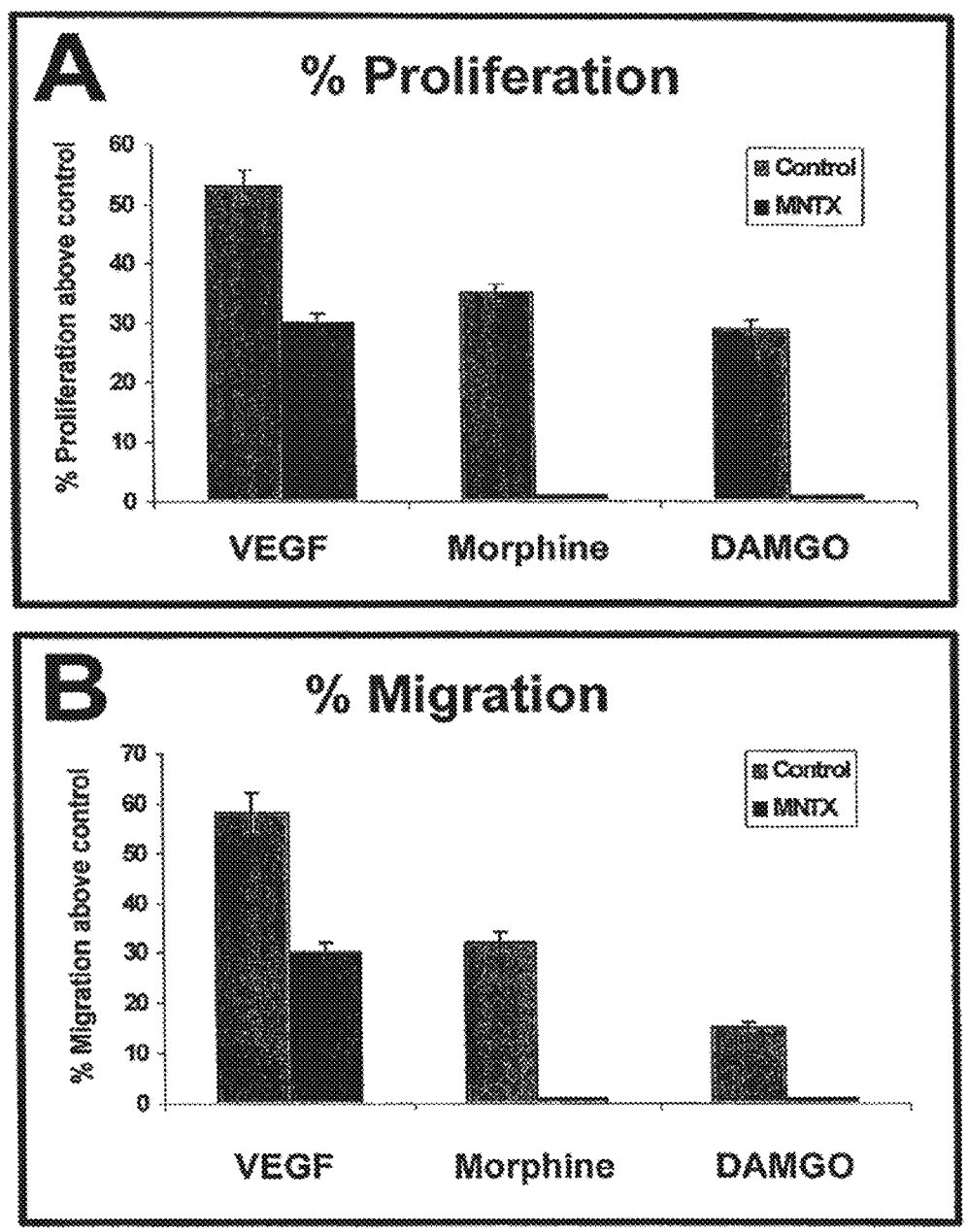
FIG. 7 is a bar graph of percent proliferation (A) and migration (B) of human pulmonary microvascular endothelial cells in the presence of VEGF, 25 morphine and DAMGO with or without MNTX.

In order to assess the mechanisms of opioid and MNTX-induced effects on angiogenesis, a well-characterized EC line was used, human pulmonary microvascular endothelial cells (HPMVEC). In agreement with the effects on human dermal microvascular EC, it was observed that MS, DAMGO and VEGF induce HPMVEC migration which is inhibited by MNTX (FIG. 7B). It was shown that MS, DAMGO and VEGF also stimulate HPMVEC proliferation which is attenuated by MNTX (FIG. 7A).

Considering the inhibitory effects of MNTX, a mu opioid receptor antagonist, on VEGF-induced EC proliferation and migration, the role of opioids on VEGF receptor transactivation was examined. FIG. 8A shows that MS and DAMGO induce tyrosine phosphorylation of both VEGF receptor 1 (Flt-1) and 2 (Flk-1) which is blocked by MNTX. Further, MNTX attenuates the tyrosine phosphorylation of VEGF receptors 1 and 2 induced by VEGF. These results indicate that opioids induce VEGF receptor transactivation.

In order to address if VEGF receptor tyrosine kinase activity is required for opioid-induced angiogenesis, EC were pre-treated with a VEGF receptor 1 and 2 tyrosine kinase inhibitor and measured opioid-induced EC proliferation and migration (FIG. 8B). The results indicate that the tyrosine kinase activity of VEGF receptors is important in opioid-induced EC angiogenic functions.

One important signaling molecule involved in angiogenesis is the small G-protein, RhoA (Aepfelbacher et al. 1997; Cascone et al. 2003; Hoang et al. 2004; Liu and Senger 2004). It was observed that MS, DAMGO and VEGF stimulate RhoA activation which is inhibited by MNTX (FIG. 9A). Further, VEGF receptor transactivation is important for opioid-induced RhoA activation (FIG. 9B). Silencing RhoA expression blocks opioid and VEGF-induced EC proliferation and migration (FIG. 10). These results indicate the pivotal role of RhoA activation on agonist-induced EC angiogenic activity.

Figure 11:
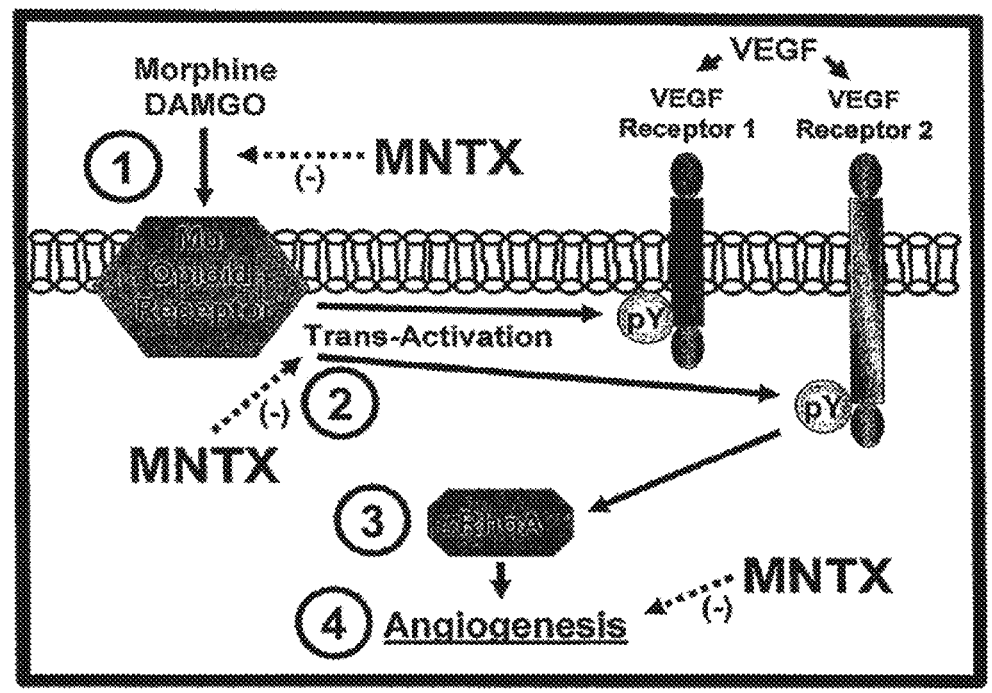
FIG. 11 is a schematic diagram summarizing the mechanism of MNTX effects on angiogenesis.

Taken as a whole these findings suggest a model in which the peripheral mu opioid receptor antagonist, MNTX, attenuates opioid and VEGF-induced VEGF receptor and RhoA activation. This attenuation is important for the inhibitory role of MNTX on opioid and VEGF-mediated angiogenesis (FIG. 11).

Example 9

Figure 12:
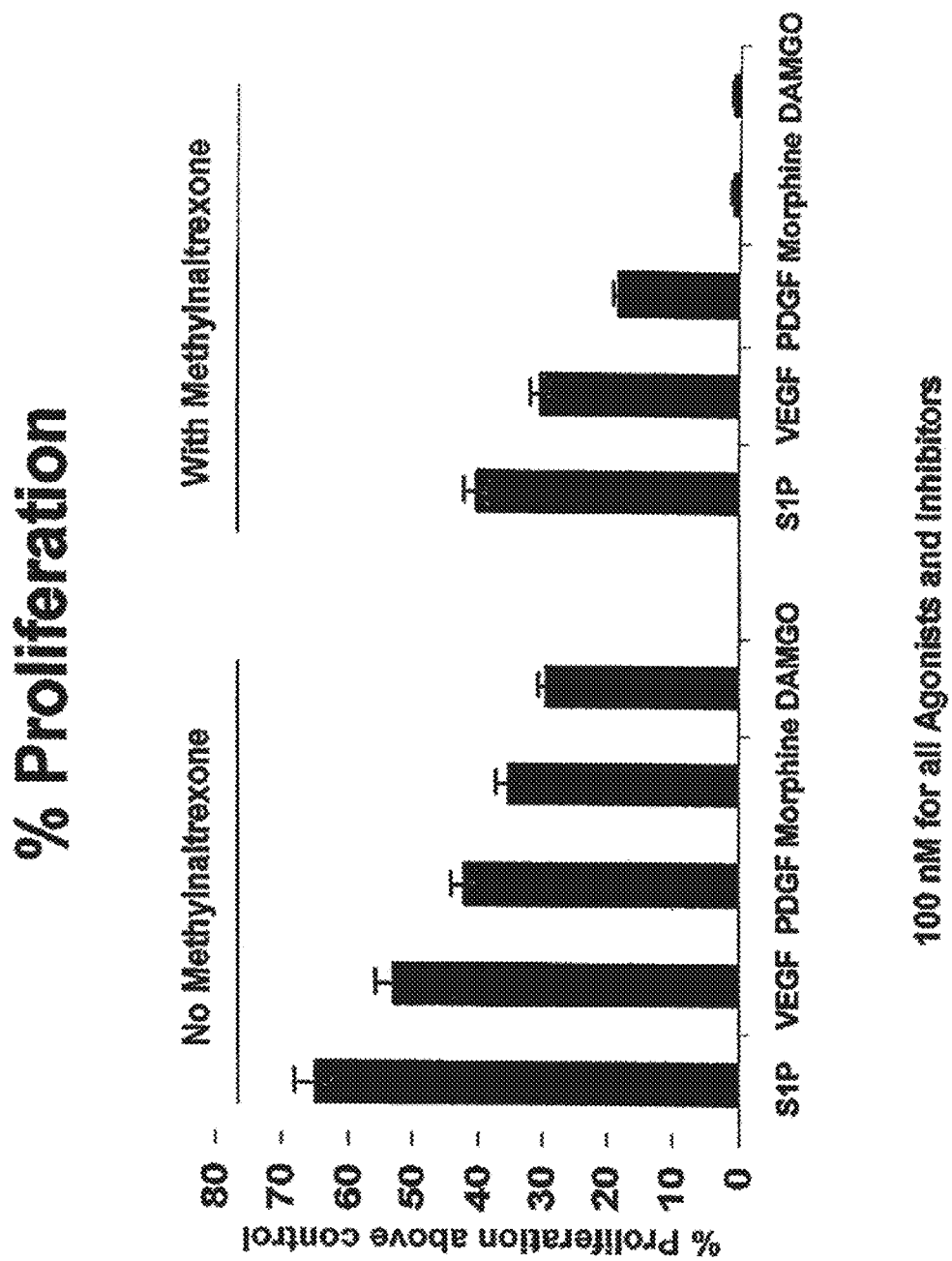
FIG. 12 is a bar graph of percent proliferation above control of pulmonary microvascular endothelial cells in the presence of SIP, VEGF, PDGF, morphine and DAMGO with or without MNTX.
Figure 13:
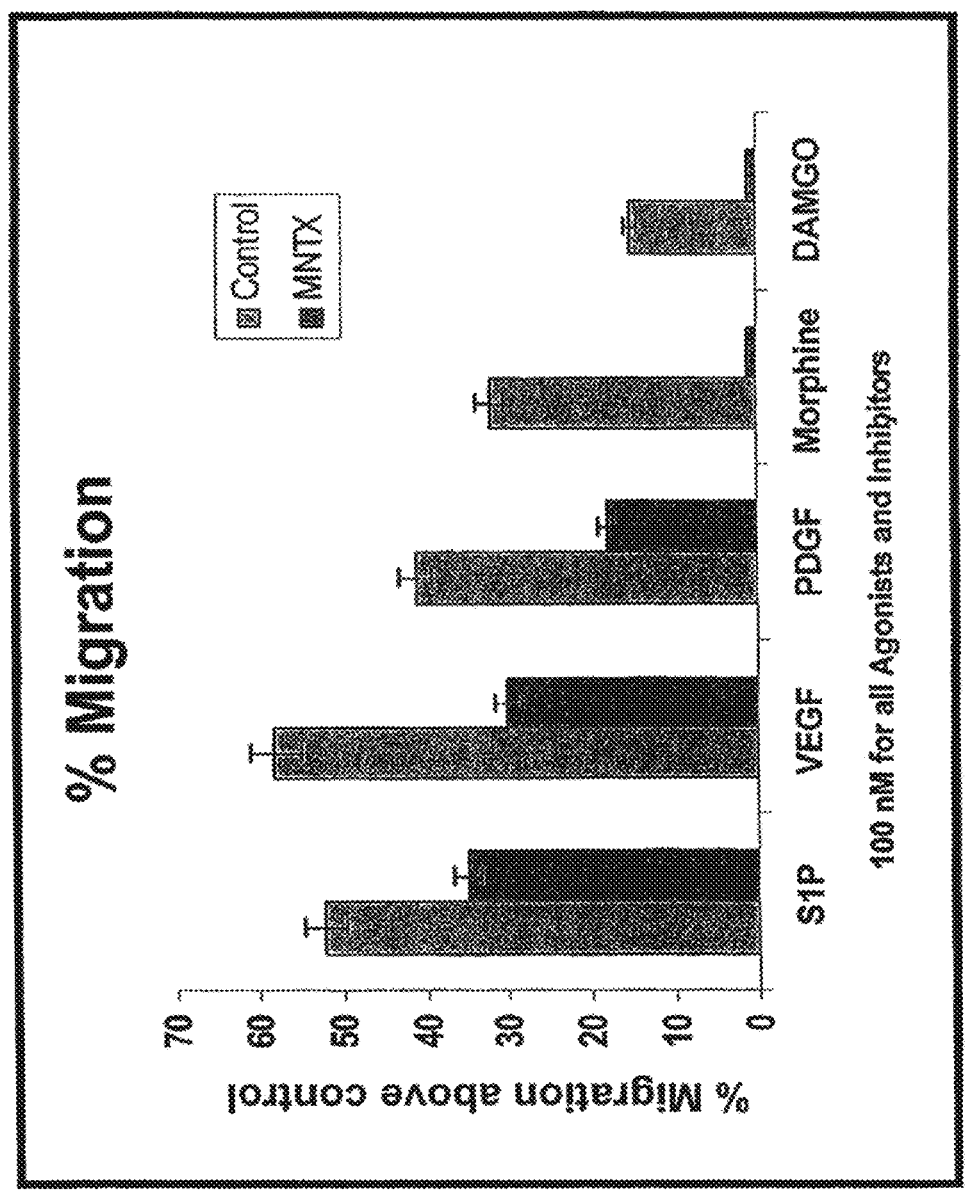
FIG. 13 is a bar graph of percent migration above control of pulmonary microvascular endothelial cells in the presence of SIP, VEGF, PDGF, morphine and DAMGO with or without MNTX.
Figure 14:
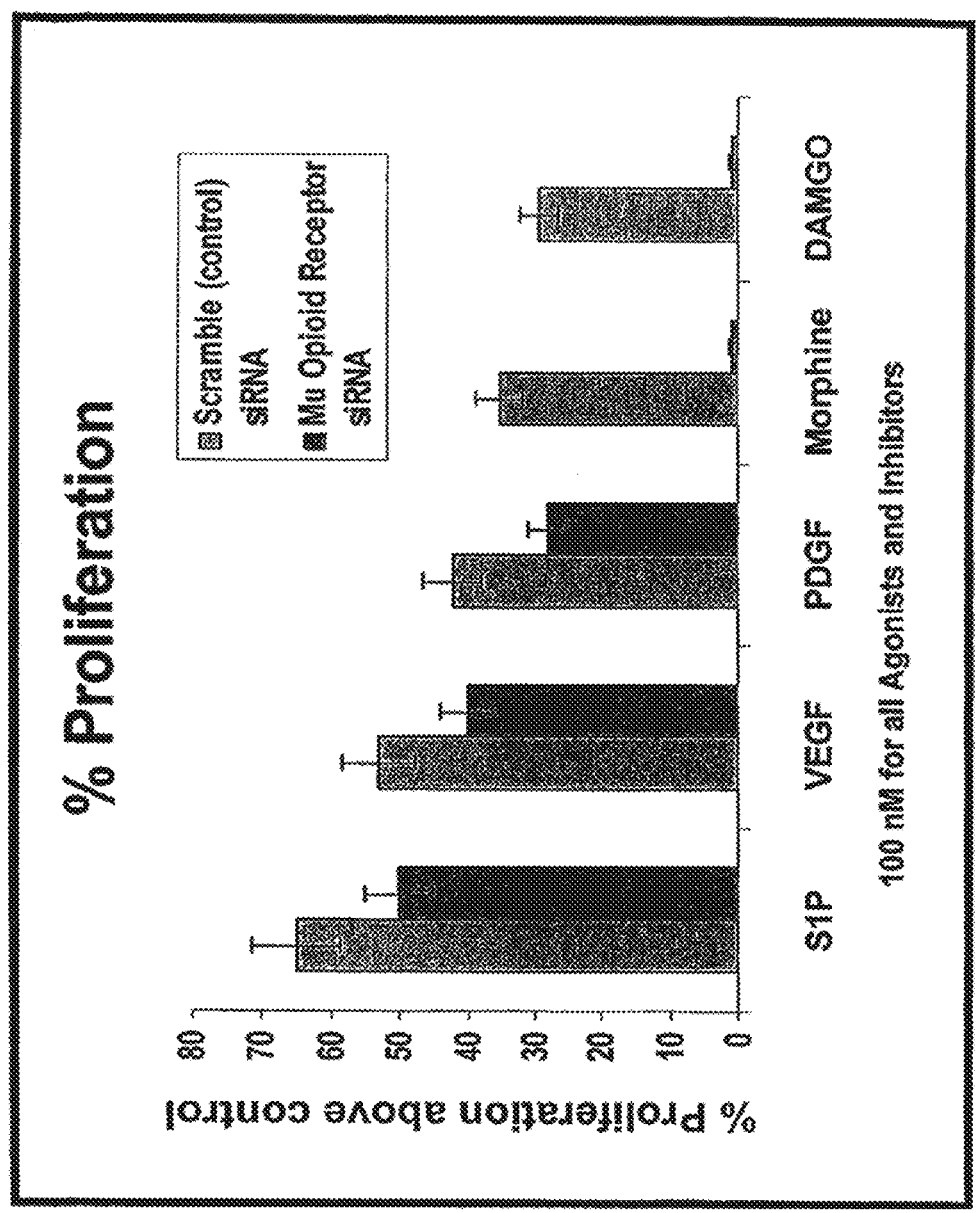
FIG. 14 is a bar graph of percent proliferation above control of pulmonary microvascular endothelial cells in the presence of SIP, VEGF, PDGF, morphine and DAMGO with scramble (control) siRNA or with mu opioid receptor siRNA.
Figure 15:
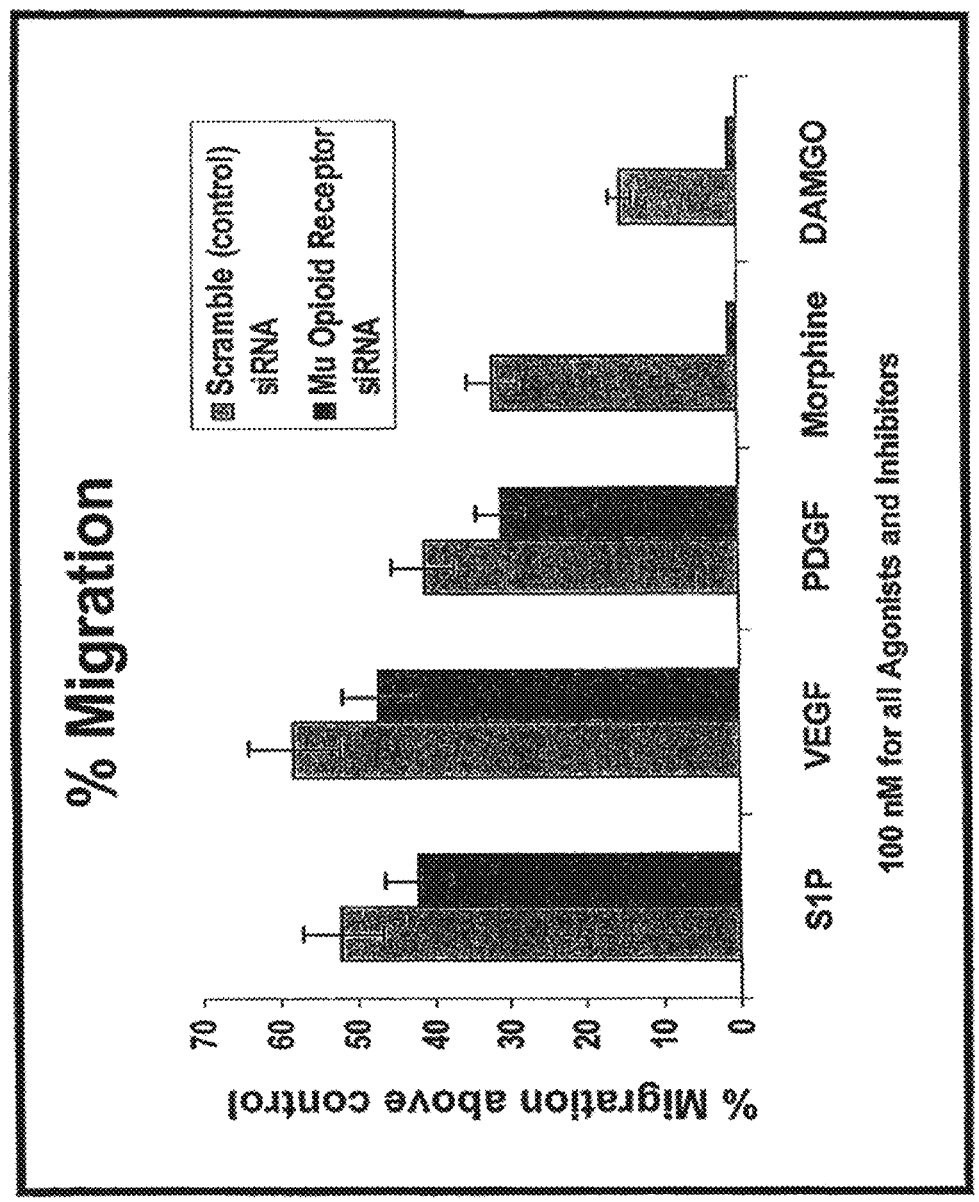
FIG. 15 is a bar graph of percent migration above control of pulmonary 25 microvascular endothelial cells in the presence of SIP, VEGF, PDGF, morphine and DAMGO with scramble (control) siRNA or with mu opioid receptor siRNA.
Figure 16:
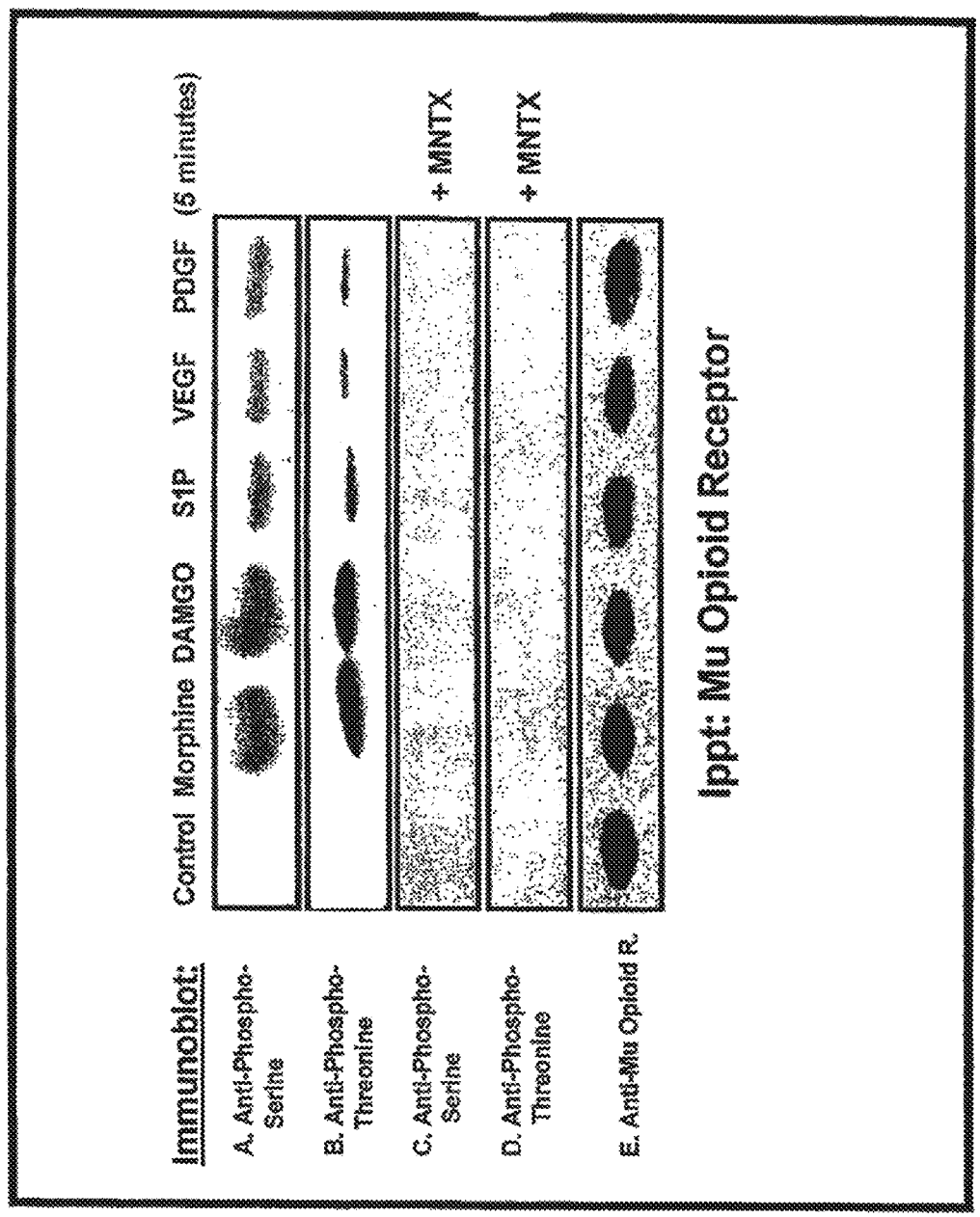
FIG. 16 is a panel of immunoblots indicating phosphorylation (activation) of the mu opioid receptor using immunoprecipitated mu opioid receptor and (A, C) anti-phospho-serine, (B, D) anti-phospho-threonine of human pulmonary microvascular endothelial cells in the presence of morphine, DAMGO, SIP, VEGF, PDGF with MNTX (C, D) or without MNTX (A, B); (E) is an immunoblot of anti-mu opioid receptor.
Figure 17:
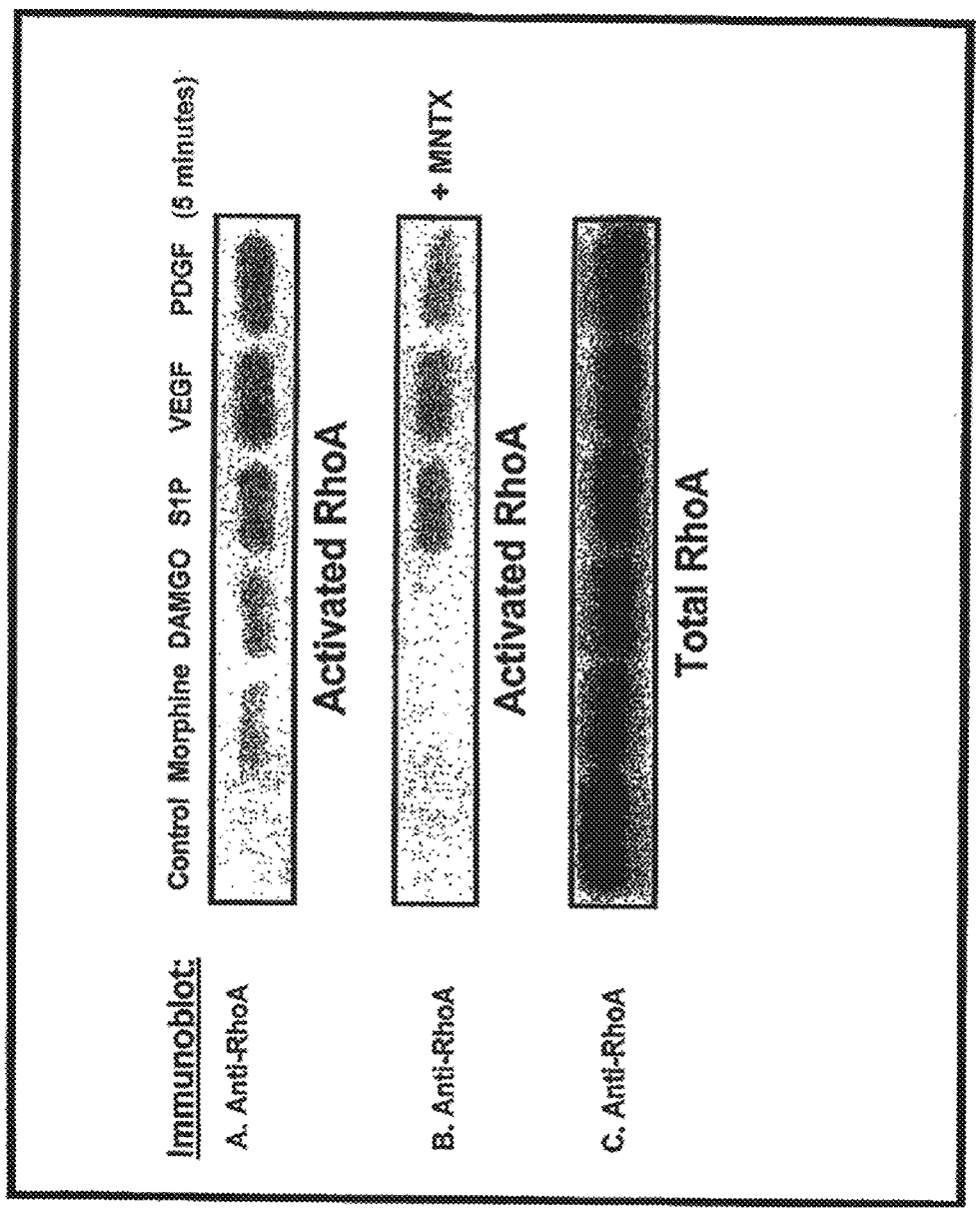
FIG. 17 is an anti-RhoA immunoblot of (A, B) activated RhoA and (C) total RhoA of human pulmonary microvascular endothelial cells in the presence of morphine, DAMGO, SIP, VEGF, PDGF with MNTX (B) and without MNTX (A).
Figure 18:
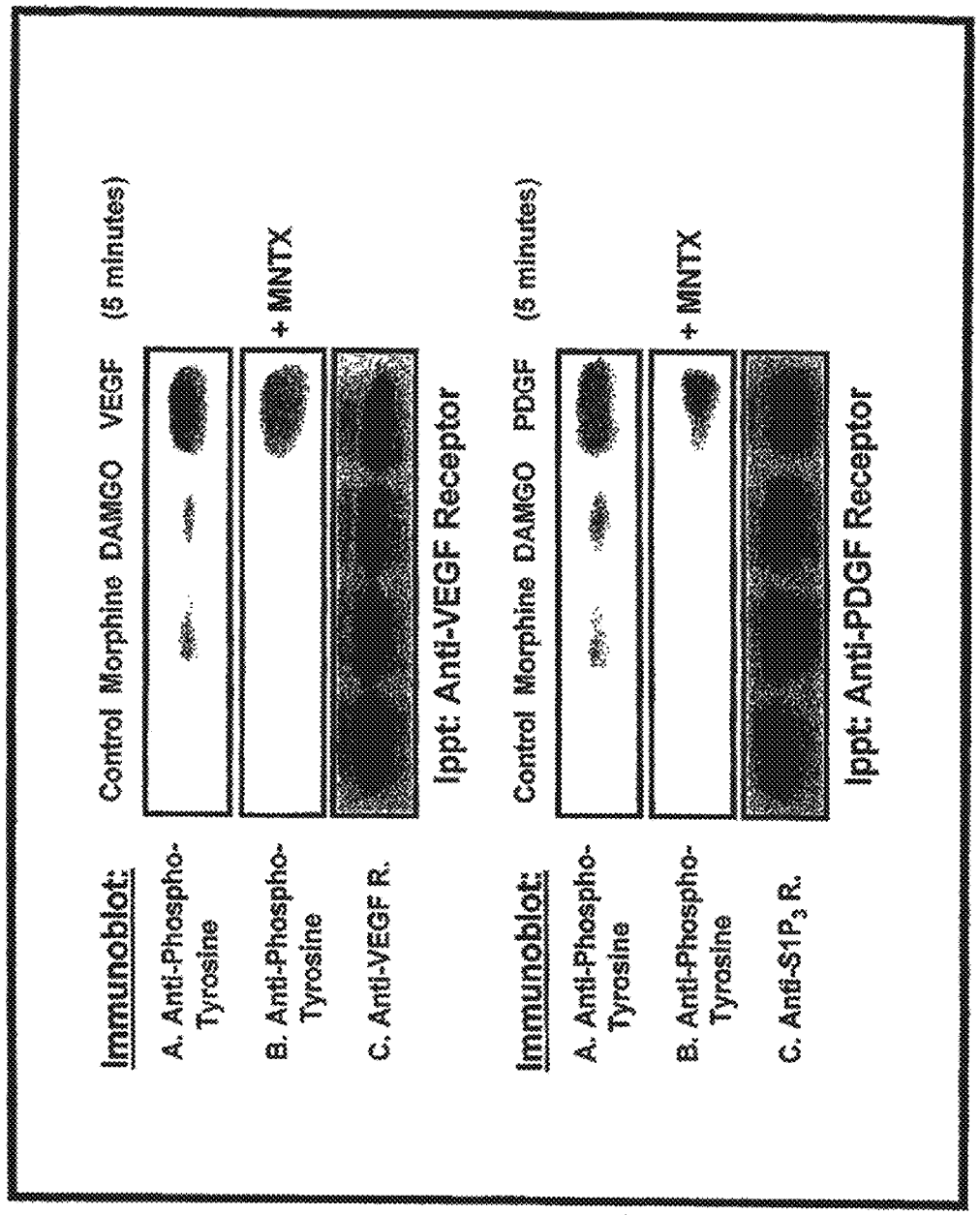
FIG. 18 is a panel of immunoblots of top panel: (A, B) anti-phospho-tyrosine, (C) anti-VEGF R and bottom panel: (A, B) anti-phospho-tyrosine, (C) anti-PDGF R, of human pulmonary microvascular endothelial cells in the presence of morphine, DAMGO, VEGF (top panel) or PDGF (bottom panel) with MNTX (B in each panel) or without MNTX (A in each panel).
Figure 19:
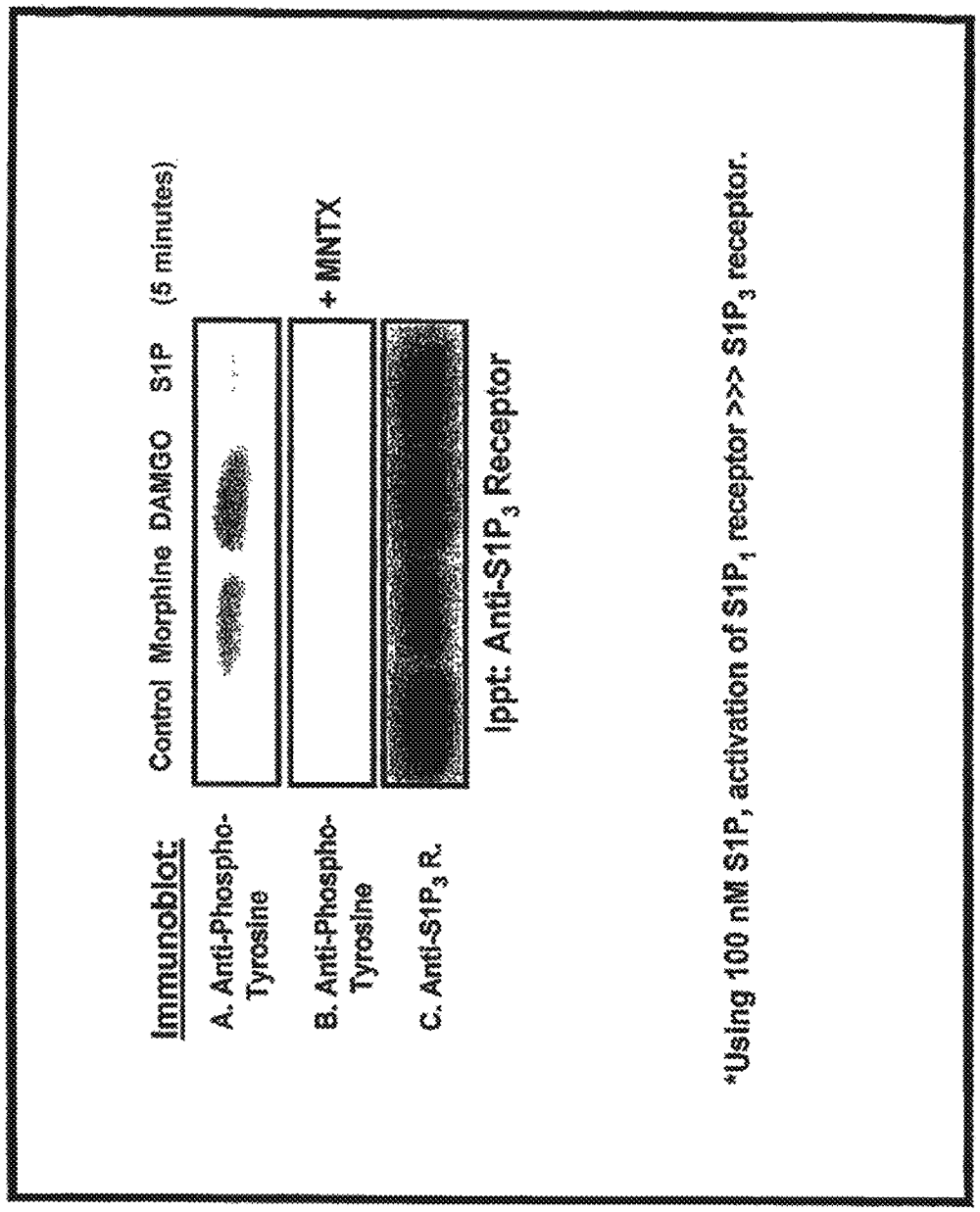
FIG. 19 is a panel of immunoblots indicating tyrosine phosphorylation (activation) of the $S1P_3$ receptor using immunoprecipitated $S1P_3$ receptor and (A, B) anti-phospho-tyrosine, (C) anti-$S1P_3$ R, of human pulmonary microvascular endothelial cells in the presence of morphine, DAMGO, and S1P with MNTX (B) or without MNTX (A).
Figure 20:
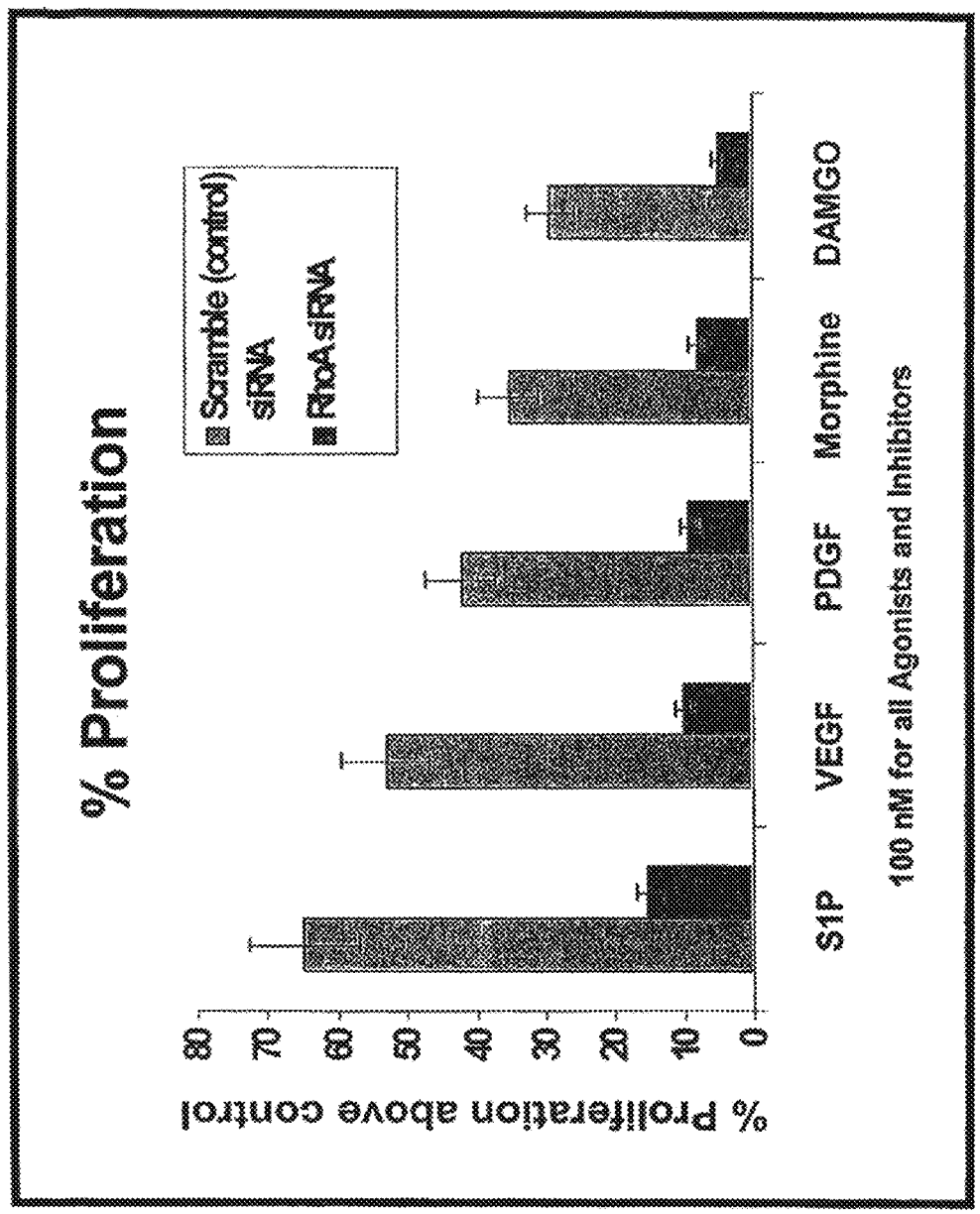
FIG. 20 is a bar graph of percent proliferation above control of pulmonary microvascular endothelial cells in the presence of S1P, VEGF, PDGF, morphine and DAMGO with scramble (control) siRNA or with RhoA siRNA.
Figure 21:
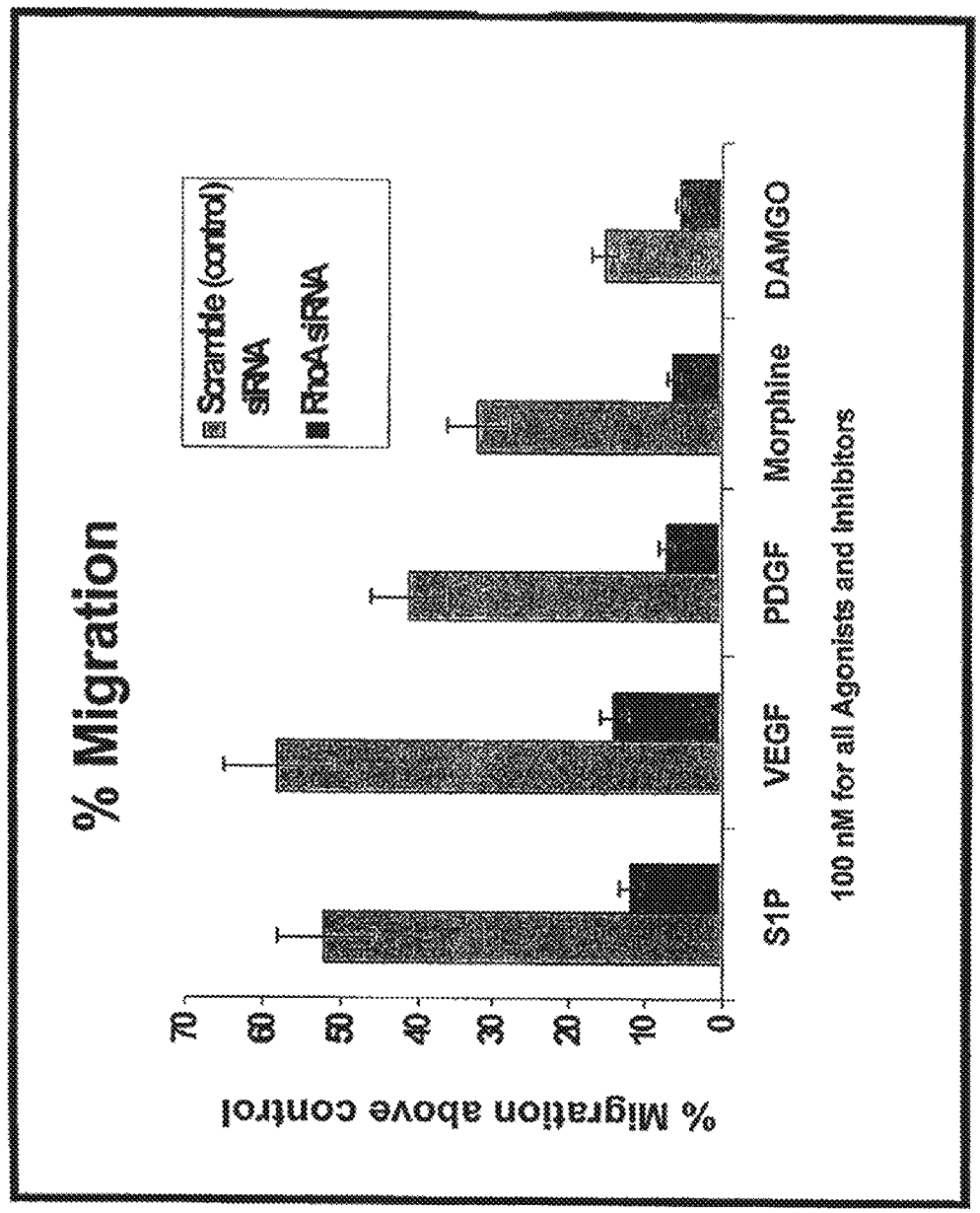
FIG. 21 is a bar graph of percent migration above control of pulmonary 20 microvascular endothelial cells in the presence of S1P, VEGF, PDGF, morphine and DAMGO with scramble (control) siRNA or with RhoA siRNA.
Figure 22:
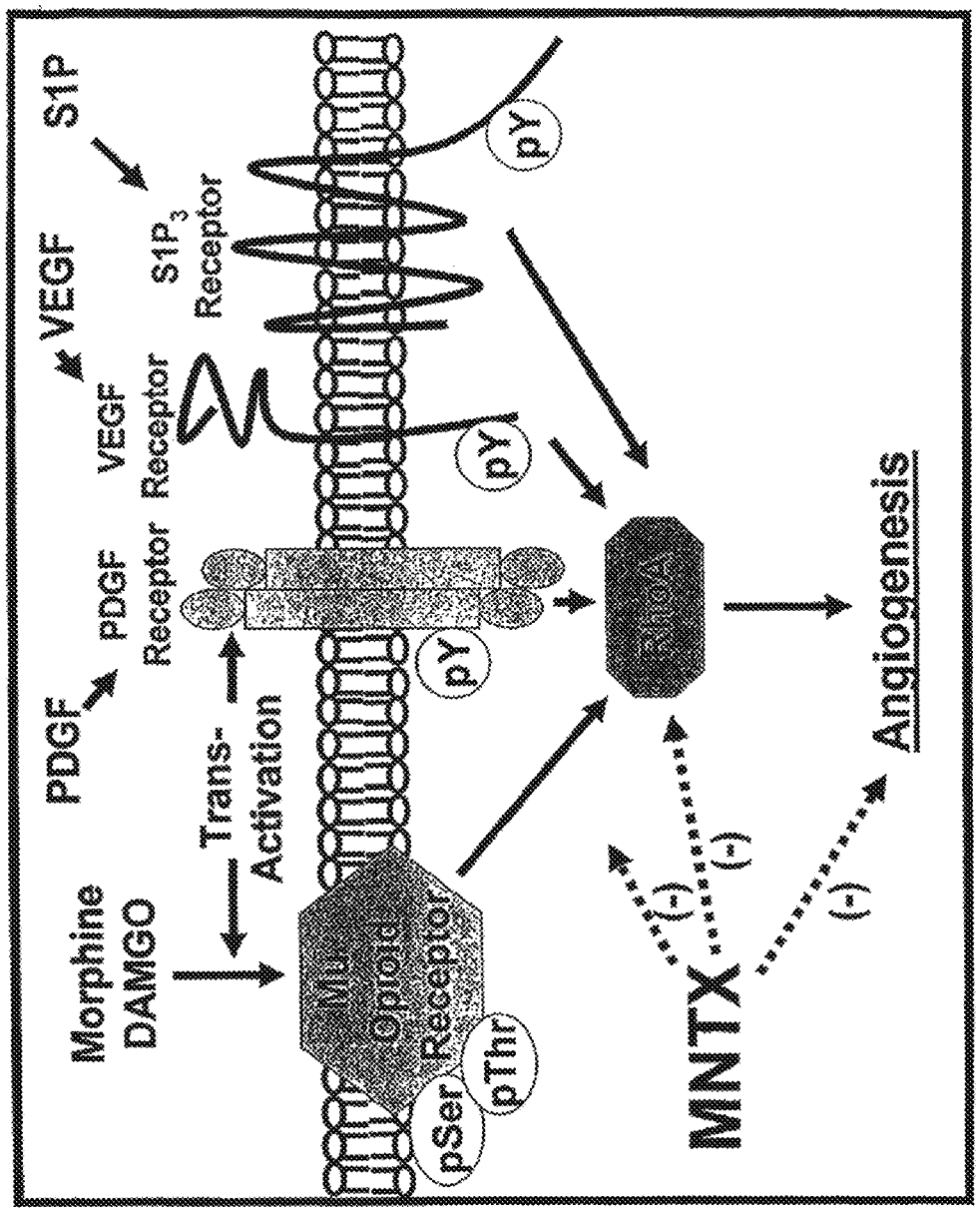
FIG. 22 is an schematic diagram summarizing the mechanism of MNTX effects on RhoA activation and angiogenesis.

Methylna ltrexone Inhibits SIP, VEGF and PDGF-Induced Angiogenesis: Role of Receptor Transactivation Assays were conducted according to the procedure similar to that described in Examples 1-3. It was observed that SIP, VEGF, PDGF, morphine and DAM GO induced proliferation (FIG. 12) (as measured by the colorimetric CellTiter™ (Promega) MTS assay) and migration (FIG. 13) (as measured by the Transwell™ (Costar) permeable membrane filter assay (8 J.Im pore diameter)) of EC which were inhibited by pretreatment with MNTX (0.1 µM, 1 hour). Silencing mu opioid receptor expression (siRNA) blocks morphine and DAMGO-induced EC proliferation (FIG. 14) and migration (FIG. 15) while also significantly inhibiting SIP, VEGF and PDGF-induced EC proliferation (FIG. 14) and migration (FIG. 15). Immunoprecipitation followed by immunoblot analyses indicate that SIP, VEGF and PDGF treatment of EC induced serine/threonine phosphorylation of the mu opioid receptor (FIG. 16) (indicating receptor transactivation) and activation of the cytoskeletal regulatory small G-protein, RhoA (FIG. 17). Further, morphine and DAMGO treatment of EC induced tyrosine phosphorylation of the VEGF receptor (FIG. 18), PDGF receptor (FIG. 18) and SIP 3 receptor (FIG. 19) along with RhoA activation. MNTX pretreatment of EC attenuated morphine, DAMGO, SIP, VEGF and PDGF induced receptor phosphorylation events and RhoA activation. Finally, silencing RhoA expression (siRNA) blocked agonist-induced EC proliferation (FIG. 20) and migration (FIG. 21). Taken together, these results indicate that MNTX inhibits agonist induced EC proliferation and migration via inhibition of receptor phosphorylation/transactivation and subsequent inhibition of Rho A activation (FIG. 22). These results suggest that MNTX inhibition of angiogenesis can be a useful therapeutic intervention for cancer treatment.

Example 10

Figure 23:
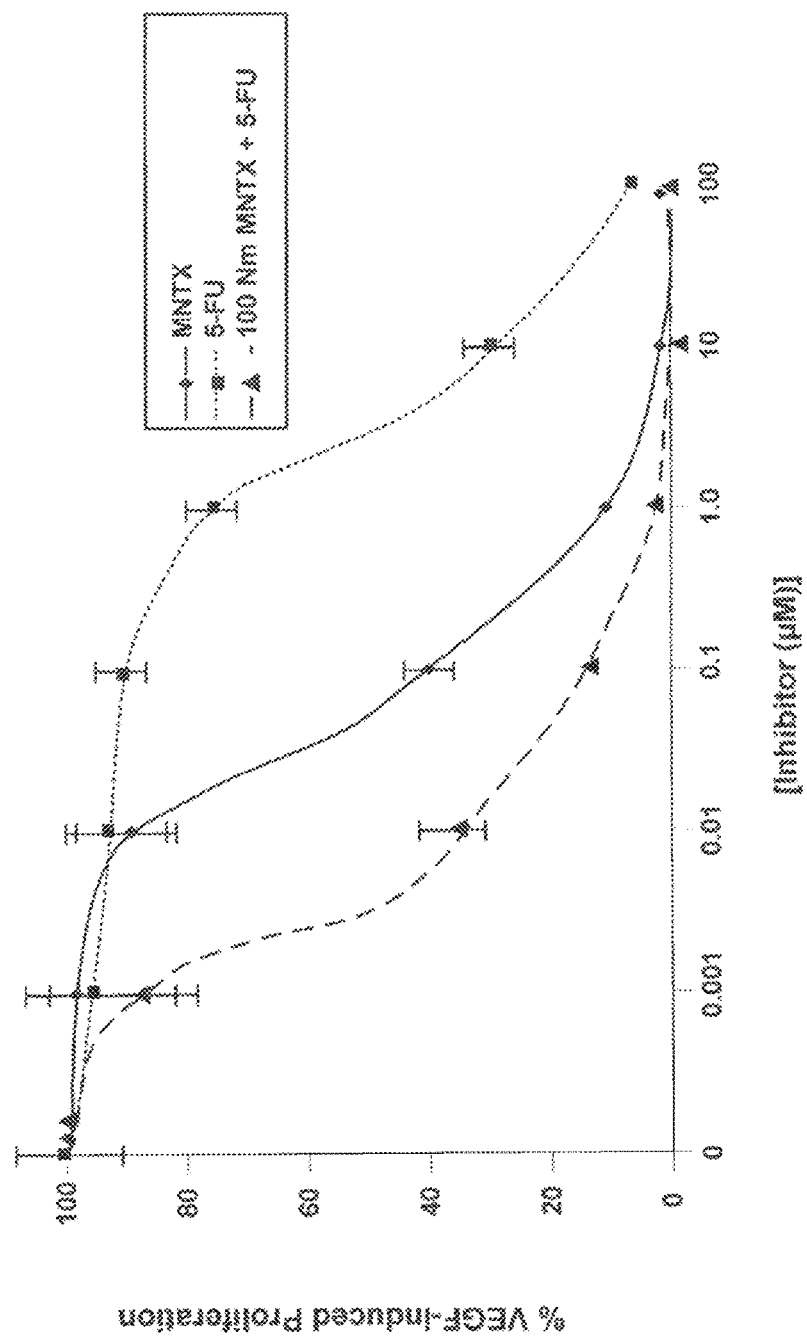
FIG. 23 is a graph of percent proliferation above control of microvascular 25 endothelial cells in the presence of VEGF with MNTX, with 5-FU and with a combination of MNTX and 5-FU.
Figure 24:
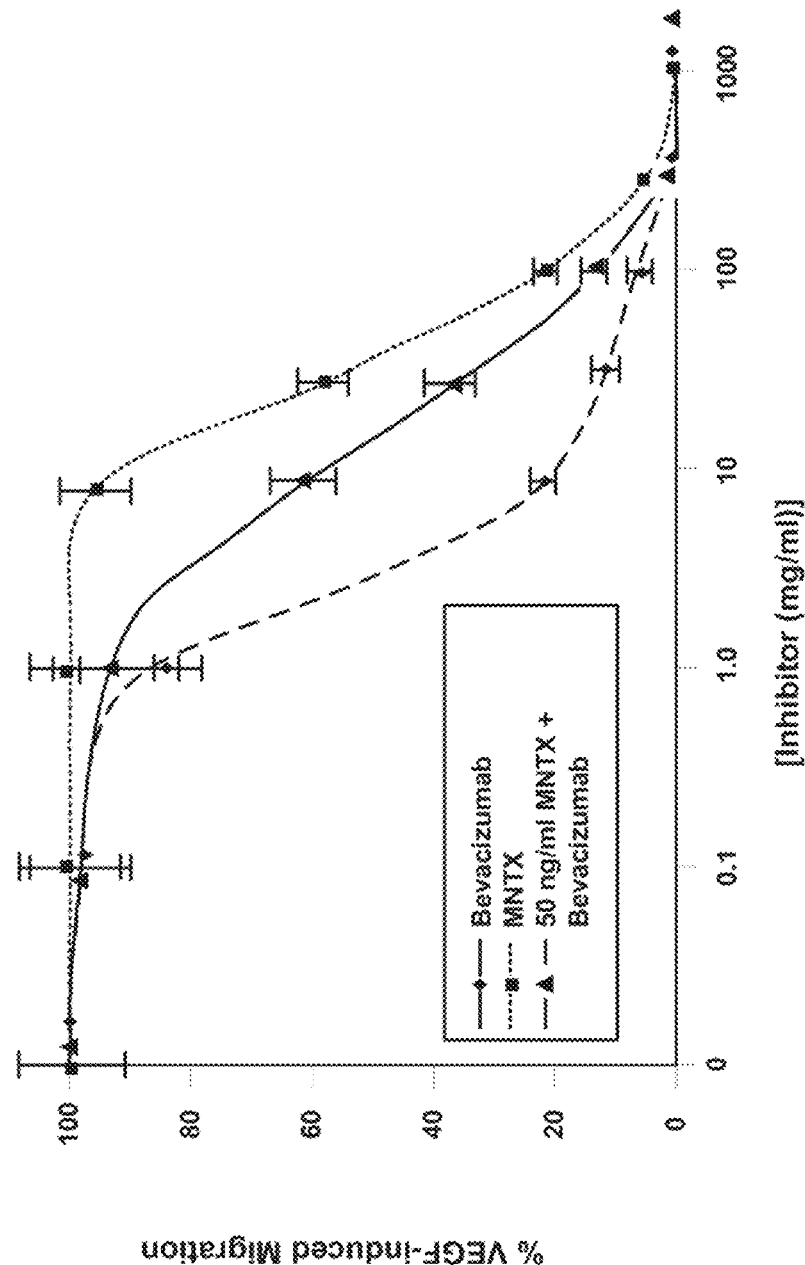
FIG. 24 is a graph of percent migration above control of microvascular endothelial cells in the presence of VEGF with MNTX, with Bevacizumab and with a combination of MNTX and Bevacizumab.

Methylnaltrexone and Antiproliferative Compounds Synergistically Inhibit VEGF-Induced Proliferation and Migration Assays were conducted according to the procedure similar to that described in Examples 1-3. It was observed that methylnaltrexone and 5-FU synergistically inhibit VEGF induced proliferation of endothelial cells. (FIG. 23). It was likewise observed that methylnaltrexone and Bevacizumab synergistically inhibit VEGF induced migration of endothelial cells. (FIG. 24).

Example 11

Effects of MNTX on Various Cancer Cell Lines

Figure 25:
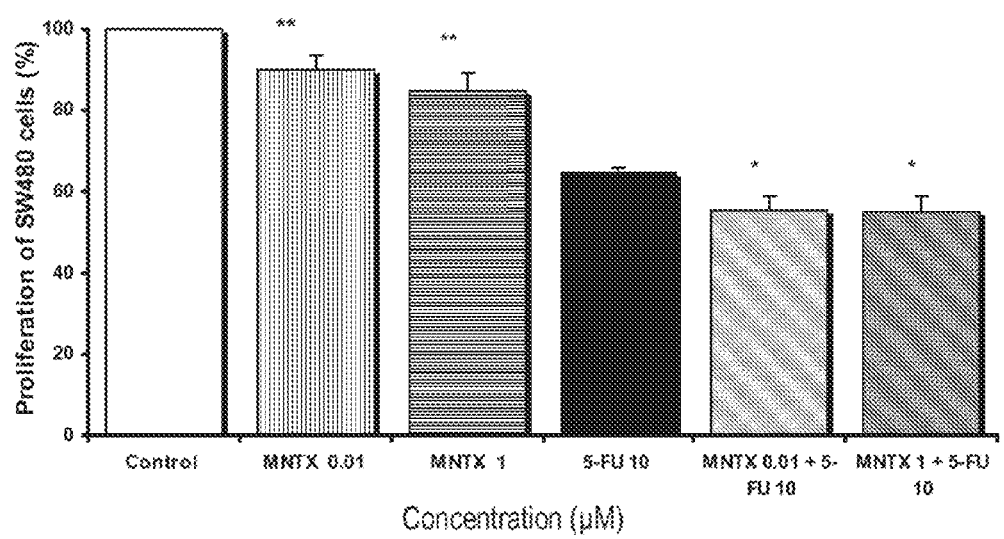
FIG. 25 is a bar graph of the effects of MNTX, 5-FU, and a combination of both on SW480 human colorectal cancer cell line.
Figure 26:
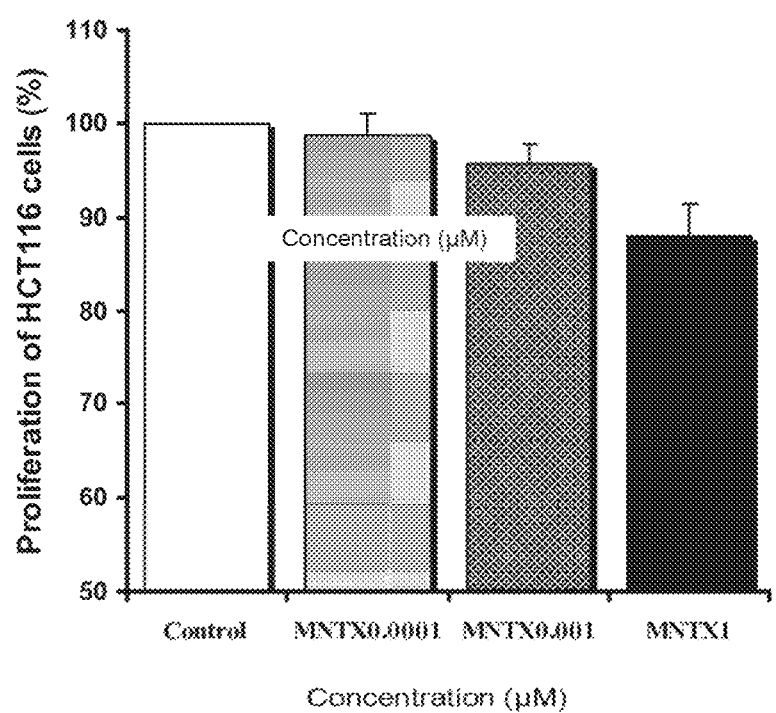
FIG. 26 is a bar graph of the effects of MNTX, 5-FU, and a combination of both on HCT116 human colorectal cancer cell line.
Figure 27:
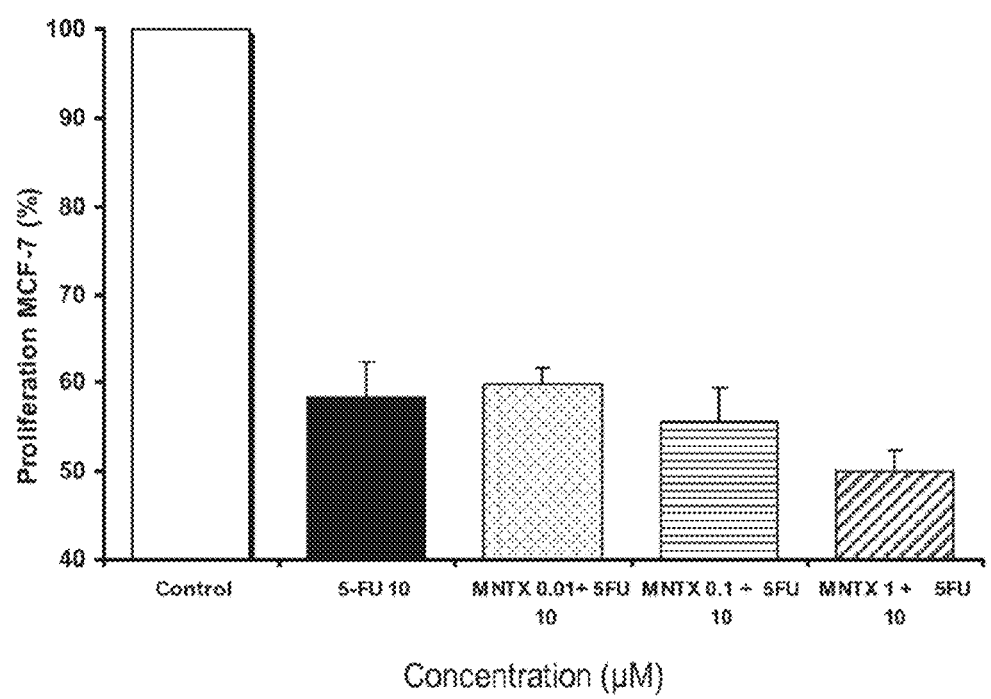
FIG. 27 is a bar graph of the effects of MNTX, 5-FU, and a combination of both on MCF-7 human breast cancer cell line.
Figure 28:
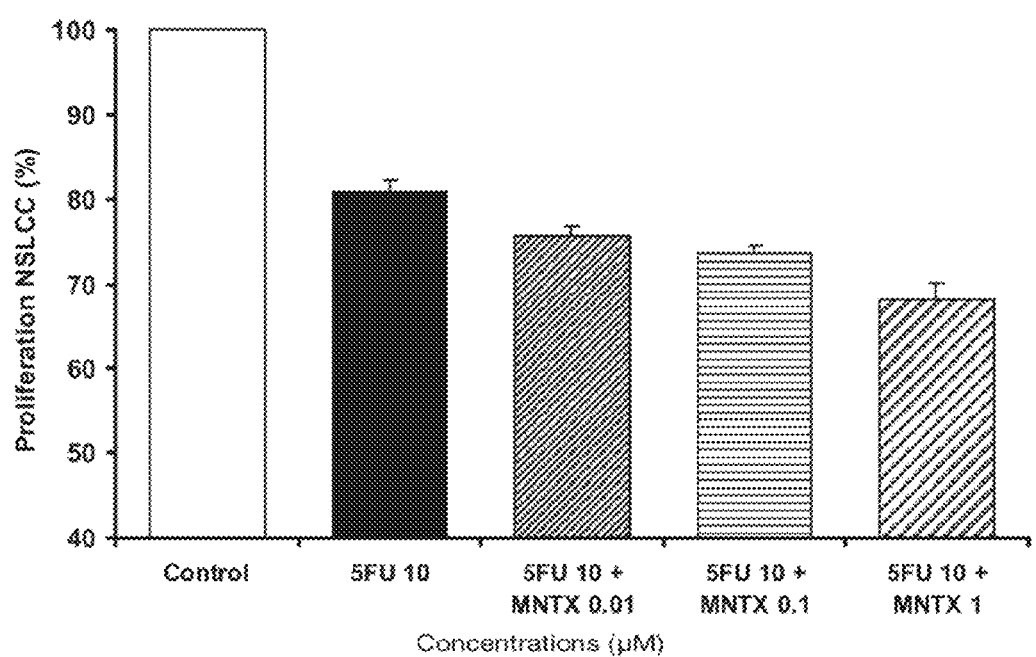
FIG. 28 is a bar graph of the effects of MNTX, 5-FU, and a combination of both on non-small lung cancer cell (NSLCC) line.

The effects of MNTX on SW 480 human colorectal cancer cell line were evaluated. As shown in FIG. 25, it was observed that MNTX itself possesses antiproliferation activity in SW 480 cells (**, $P<0.01$ compared to control). In addition, MNTX enhanced 5-FU's tumoricidal effect (*, $P<0.05$ compared to 5-FU 10 uM only, approx. IC50 for this cell line). As shown in FIGS 26, 27, and 28, respectively, similar results were obtained in HCT116 human colorectal cancer cell line, MCF-7 human breast cancer cell line, and non-small lung cancer cell (NSLCC) line.

In summary, the present invention provides methods of attenuating endothelial cell migration and/or proliferation associated with angiogenesis and/or enhancing endothelial cell barrier function in tissue or an organ of a subject in need therefor by administering one or more opioid antagonists, especially peripheral opioid antagonists, in an effective amount to the patient to inhibit the migration and/or proliferation and angiogenesis, and/or improve barrier function. The methods of the present invention may also involve administering a peripheral opioid antagonist to a patent receiving opioid treatment. Especially suitable may be a mu peripheral opioid antagonist. The present invention also provides methods of co-administering an opioid and a peripheral opioid antagonist to a subject in need therefore. The peripheral opioid antagonist may also be co-administered with an anticancer agent, as may the combination of the opioid and peripheral opioid antagonist be co-administered with an anticancer agent.

Example 12

MNTX Enhances the Ability of Chemotherapeutics to Inhibit Cell Proliferation in Human Lung Cancer Cells Cell Culture and Reagents—

The human Non-Small Cell Lung Cancer (NSCLC) cell line H1993 was obtained from ATCC (Walkersville, Md.) and cultured in Roswell Park Memorial Institute complete medium (Cambrex, East Rutherford, N.J.) at 37° C. in a humidified atmosphere of 5% $CO_2$, 95% air, with passages 6-10 used for experimentation. Unless otherwise specified, reagents were obtained from Sigma (St. Louis, Mo.). Morphine was purchased from Baxter (Deerfield, Ill.). N-methylnaltrexone bromide or methylnaltrexone (MNTX) was purchased from Mallinckrodt Specialty Chemicals (Phillipsburg, N.J.). Erlotinib (epidermal growth factor receptor tyrosine kinase inhibitor), Vinorelbine Tartrate (inhibits mitosis through interaction with tubulin), Paclitaxel (microtubule polymer stabilizer), Docetaxel (inhibitor of depolymerisation of microtubules) and Gemcitabine HCl (DNA synthesis inhibitor) were purchased from Selleck Chemicals (Houston, Tex.).

Human NSCLC Cell Proliferation Assay—

H1993 cells ($5 \times 10^3$ cells/well) were incubated with 0.2 ml of serum-free media containing 0, 0.01, 0.1, 0.5, 1, 5 or 10 uM of either Erlotinib (epidermal growth factor receptor tyrosine kinase inhibitor), Vinorelbine Tartrate (inhibits mitosis through interaction with tubulin), Paclitaxel (microtubule polymer stabilizer), Docetaxel (inhibitor of depolymerisation of microtubules) or Gemcitabine HCl (DNA synthesis inhibitor). These are indicated as Control. In some cases, morphine (100 nM) or morphine (100 uM) plus methylnaltrexone (MNTX, 10 nM or 100 nM) were added in addition to the chemotherapeutic agents. Treated cells were grown for 24 h at 37° C. in 5% $CO_2$/95% air in 96-well culture plates. The in vitro cell proliferation assay was analyzed by measuring the change in cell number using the CellTiter96™ MTS assay (Promega, Madison, Wis.) and read at 492 nm.

Results are represented graphically (FIG. 29) with the y-axis indicating Percent Inhibition of Cell Proliferation and the x-axis indicating drug concentration. The results shown in FIG. 29 indicate that Erlotinib, Paclitaxel, Gemcitabine HCl, Vinorelbine Tartrate and Docetaxel inhibit human NSCLC proliferation in a dose-dependent manner. Morphine decreases the ability of these chemotherapeutic agents to inhibit H1993 cell proliferation thus promoting multidrug resistance. In contrast, MNTX reversed the effects of morphine on multidrug resistance in a dose-dependent manner and enhanced the effects of the chemotherapeutic agents.

While the present invention has now been described and exemplified with some specificity, those skilled in the art will appreciate the various modifications, including variations, additions, and omissions that may be made in what has been described. Accordingly, it is intended that these modifications also be encompassed by the present invention and that the scope of the present invention be limited solely by the broadest interpretation that lawfully can be accorded the appended claims.

All patents, publications and references cited herein are hereby fully incorporated by reference. In case of conflict between the present disclosure and incorporated patents, publications and references, the present disclosure should control.

The invention claimed is:

1. A method of enhancing the efficacy of a cancer chemotherapeutic agent in a subject, the method comprising administering the cancer chemotherapeutic agent and wherein the chemotherapeutic agent is a tyrosine kinase inhibitor, an anti-microtubule, or an anti metabolite, and wherein the subject is taking concurrent opioid therapy to a subject having a cancer.

2. The method of claim 1, wherein the chemotherapeutic agent is a tyrosine kinase inhibitor.

3. The method of claim 2, wherein the tyrosine kinase inhibitor is an EGFR inhibitor.

4. The method of claim 3, wherein the tyrosine kinase inhibitor is erlotinib.

5. The method of claim 1, wherein the chemotherapeutic agent is an anti-microtubule.

6. The method of claim 5, wherein the anti-microtubule is selected from the group consisting of vinorelbine, paclitaxel and docetaxel, and a combination thereof.

7. The method of claim 1, wherein the chemotherapeutic agent is an antimetabolite.

8. The method of claim 7, wherein the antimetabolite is gemcitabine.

9. A method of treating non-small cell lung cancer in a subject in need thereof, the method comprising administer-

---

SEQUENCE LISTING

<160> NUMBER OF SEQ ID NOS: 4

<210> SEQ ID NO 1
<211> LENGTH: 21
<212> TYPE: DNA
<213> ORGANISM: Homo sapiens

<400> SEQUENCE: 1
aagaaactgg tgattgttgg t                                              21

<210> SEQ ID NO 2
<211> LENGTH: 21
<212> TYPE: DNA
<213> ORGANISM: Homo sapiens

<400> SEQUENCE: 2
aaagacatgc ttgctcatag t                                              21

<210> SEQ ID NO 3
<211> LENGTH: 21
<212> TYPE: DNA
<213> ORGANISM: Homo sapiens

<400> SEQUENCE: 3
aagagaaatc gaaaccgaaa a                                              21

<210> SEQ ID NO 4
<211> LENGTH: 21
<212> TYPE: DNA
<213> ORGANISM: Homo sapiens

<400> SEQUENCE: 4
aagaacccaa ttaagcgcaa g                                              21 ing to the subject a therapeutically effective amount of a composition comprising a chemotherapeutic agent in combination with a therapeutically effective amount of a composition comprising methylnaltrexone, wherein the chemotherapeutic agent is a tyrosine kinase inhibitor, an antimicrotubule, or an antimetabolite, and wherein the subject is taking concurrent opioid therapy.

\* \* \* \* \*

UNITED STATES PATENT AND TRADEMARK OFFICE
CERTIFICATE OF CORRECTION

PATENT NO. : 9,662,325 B2
APPLICATION NO. : 14/292816
DATED : May 30, 2017
INVENTOR(S) : Jonathan Moss et al.

Page 1 of 1

It is certified that error appears in the above-identified patent and that said Letters Patent is hereby corrected as shown below:

In the Claims

In Claim 1, Column 40, Line 4:
After the word "and", insert the word --methylnaltrexone to a subject having a cancer--.

In Claim 1, Column 40, Lines 7-8:
Delete the words "to a subject having a cancer".

Signed and Sealed this
Eleventh Day of June, 2019

Andrei Iancu
*Director of the United States Patent and Trademark Office*